(12) United States Patent
Bonfanti et al.

(10) Patent No.: US 8,044,073 B2
(45) Date of Patent: *Oct. 25, 2011

(54) AMINOBENZIMIDAZOLES AND BENZIMIDAZOLES AS INHIBITORS OF RESPIRATORY SYNCYTIAL VIRUS REPLICATION

(75) Inventors: Jean-François Bonfanti, Andé (FR); Koenraad Jozef Lodewijk Andries, Beerse (BE); Jérôme Michel Claude Fortin, Igoville (FR); Philippe Muller, Andé (FR); Frédéric Marc Maurice Doublet, Isneauville (FR); Christophe Meyer, Port St Ouen (FR); Rudy Edmond Willebrords, Merksplas (BE); Tom Valerius Josepha Gevers, Vosselaar (BE); Philip Maria Martha Bern Timmerman, Hasselt (BE)

(73) Assignee: Tibotec Pharmaceuticals (IE)

( * ) Notice: Subject to any disclaimer, the term of this patent is extended or adjusted under 35 U.S.C. 154(b) by 967 days.

This patent is subject to a terminal disclaimer.

(21) Appl. No.: 10/596,514

(22) PCT Filed: Dec. 20, 2004

(86) PCT No.: PCT/EP2004/053613
§ 371 (c)(1),
(2), (4) Date: Jun. 15, 2006

(87) PCT Pub. No.: WO2005/058869
PCT Pub. Date: Jun. 30, 2005

(65) Prior Publication Data
US 2007/0099924 A1 May 3, 2007

Related U.S. Application Data

(60) Provisional application No. 60/566,834, filed on Apr. 30, 2004.

(30) Foreign Application Priority Data

Dec. 18, 2003 (EP) .................................... 03104797

(51) Int. Cl.
*A61K 31/4439* (2006.01)
*C07D 401/04* (2006.01)
*C07D 401/06* (2006.01)

(52) U.S. Cl. ..................................... 514/338; 546/273.4
(58) Field of Classification Search ............... 546/273.4; 514/338
See application file for complete search history.

(56) References Cited

U.S. PATENT DOCUMENTS 6,274,611 B1 8/2001 Critchfield et al.
2005/0049290 A1 3/2005 Poitout et al.

FOREIGN PATENT DOCUMENTS

| DE | 2813523 | 10/1978 |
|---|---|---|
| EP | 0005318 | 3/1979 |
| EP | 0111993 A2 | 6/1984 |
| WO | 92/01687 | 2/1992 |
| WO | WO 92/01687 A1 | 2/1992 |
| WO | WO 95/03298 A1 | 2/1995 |
| WO | WO 01/00611 A1 | 1/2001 |
| WO | WO 01/00612 A1 | 1/2001 |
| WO | WO 01/00615 A1 | 1/2001 |
| WO | WO 02/090347 A1 | 11/2002 |
| WO | WO 02/092575 A1 | 11/2002 |
| WO | 03/053939 | 7/2003 |

OTHER PUBLICATIONS

Balant et al., "Metabolic Considerations, etc.," in Manfred ed. Burgers Medicinal Chemistry and Drug Discovery, 5th ed., vol. 1: Principles and Practice, John Wiley & Sons, Inc., 1995.*
Wyde et al., "CL387626 Exhibits Marked and Unusual Antiviral Activity Against Respiratory Syncytial Virus in Tissue Culture and in Cotton Rats.", *Antiviral Research*, 1998, vol. 38, pp. 31-42.

(Continued)

*Primary Examiner* — Patricia L Morris
(74) *Attorney, Agent, or Firm* — Mary A. Appollina

(57) ABSTRACT

Aminobenzimidazoles and benzimidazoles having inhibitory activity on RSV replication and having the formula

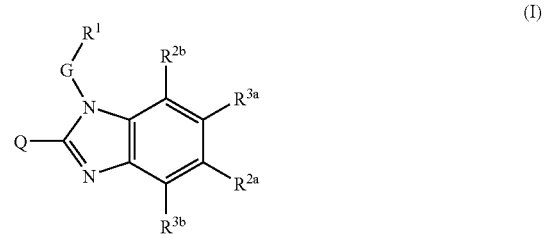

(I)

the prodrugs, N-oxides, addition salts, quaternary amines, metal complexes and stereochemically isomeric forms thereof; wherein G is a direct bond or $C_{1-10}$alkanediyl optionally substituted with one or more hydroxy, $C_{1-6}$alkyloxy, $Ar^1C_{1-6}$alkyloxy, $C_{1-6}$alkylthio, $Ar^1C_{1-6}$alkylthio, HO(—$CH_2$—$CH_2$—O$)_n$—, $C_{1-6}$alkyloxy(—$CH_2$—$CH_2$—O$)_n$— or $Ar^1C_{1-6}$alkyloxy(—$CH_2$—$CH_2$—O$)_n$—; $R^1$ is $Ar^1$ or a monocyclic or bicyclic heterocycle; Q is hydrogen, amino or mono- or di($C_{1-4}$alkyl)amino; one of $R^{2a}$ and $R^{3a}$ is selected from halo, optionally mono- or polysubstituted $C_{1-6}$alkyl, optionally mono- or polysubstituted $C_{2-6}$alkenyl, nitro, hydroxy, $Ar^2$, $N(R^{4a}R^{4b})$, $N(R^{4a}R^{4b})$sulfonyl, $N(R^{4a}R^{4b})$carbonyl, $C_{1-6}$alkyloxy, $Ar^2$oxy, $Ar^2C_{1-6}$alkyloxy, carboxyl, $C_{1-6}$alkyloxycarbonyl, or —C(=Z)$Ar^2$; and the other one of $R^{2a}$ and $R^{3a}$ is hydrogen; in case $R^{2a}$ is different from hydrogen then $R^{2b}$ is hydrogen, $C_{1-6}$alkyl or halogen and $R^{3b}$ is hydrogen; in case $R^{3a}$ is different from hydrogen then $R^{3b}$ is hydrogen, $C_{1-6}$alkyl or halogen and $R^{2b}$ is hydrogen. Compositions containing these compounds as active ingredient and processes for preparing these compounds and compositions.

29 Claims, No Drawings

OTHER PUBLICATIONS

Xue, C.B. et al., "Design, Synthesis and In vitro Activities of a Series of Benzimidazole/Benzoxazole Glycoprotein IIB/IIA Inhibitors.", *Bioorganic & Medicinal Chemistry Letters*, 1996, vol. 6, No. 3, pp. 339-344, Oxford, GB, XP000576489.

International Search Report, International Application No. PCT/EP2004/053613, Date of Mailing of International Search Report, May 15, 2005.

U.S. Appl. No. 12/253,450, filed Oct. 17, 2008.

Janssens, "New Antihistaminic N-Heterocyclic 4-Piperidinamines. 2. Synthesis and Antihistaminic activity of 1-[(4-Fluorophenyl)methyl]-N-(4-piperidinyl)-1H-benzimidazol-2-amines", J. Med. Chem., 1985, pp. 1934-1943, vol. 28.

Molina, "Preparation of [5+6]-, [6+6]-, and [6+7]-Bicyclic Guanidines from C,C-Bis(iminophosphoranes)", Chem. Berichte, 1994, pp. 1641-1652, vol. 127(9).

Da Settimo, "Synthesis of 2-Methylaminobenzimidazole Derivatives Tested for Antinflammatory Activity" Il Farmaco, 1994, pp. 29-34, vol. 49 (12).

Kovalev, "Effects of Condensed Derivatives of Benzimidazole on Gastric Secretion", Khim. Farmatsevticheskii Zhurnal, 1990, pp. 127-130, vol. 24(2) XP-002321510.

Hunger, "Benzimidazole and Related Heterocycles. VII. New 2-Aminobenzimidazoles", 1961, pp. 1273-1282, vol. 44 XP-002321511.

Khim. Geterosikl. Soedin., "1-Benzyl-2-(2-methoxyethylamino)benzimidazole" 1987, pp. 59-63, vol. 23(1) XP-002321512.

Khim. Geterosikl. Soedin., (1-benzyl-1H-benzoimidazol-2-ylamino)-phenyl-acetic acid) 1969, pp. 184, vol. 5(1) XP-0022321513.

Khim. Geterotsikl. Soedin., "Benzyl-(1-benzyl-1H-benzoimidazol-2-yl)amine" 1970, pp. 419, vol. 6(1) XP-002321514.

\* cited by examiner

AMINOBENZIMIDAZOLES AND BENZIMIDAZOLES AS INHIBITORS OF RESPIRATORY SYNCYTIAL VIRUS REPLICATION

CROSS REFERENCE TO RELATED APPLICATIONS

This application is the national stage of PCT Application No. PCT/EP2004/053613, filed Dec. 20, 2004, which application claims priority from EP Patent Application No. 03104797.0, filed 18 Dec. 2003 and U.S. provisional Patent Application No. 60/566,834, filed 30 Apr. 2004, the entire disclosures of which are hereby incorporated in their entirely.

The present invention concerns aminobenzimidazoles and benzimidazoles having antiviral activity, in particular, having an inhibitory activity on the replication of the respiratory syncytial virus (RSV). It further concerns the preparation thereof and compositions comprising these compounds.

Human RSV or Respiratory Syncytial Virus is a large RNA virus, member of the family of Paramyxoviridae, subfamily pneumoviridae together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Re-infection with RSV is thus common, despite the existence of only two subtypes, A and B.

Today only three drugs have been approved for use against RSV infection. A first one is ribavirin, a nucleoside analogue, provides an aerosol treatment for serious RSV infection in hospitalized children. The aerosol route of administration, the toxicity (risk of teratogenicity), the cost and the highly variable efficacy limit its use. The other two drugs, RespiGam® and palivizumab, polyclonal and monoclonal antibody immunostimulants, are intended to be used in a preventive way.

Other attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drug against RSV replication.

Previously, benzimidazoles and imidazopyridines as inhibitors of RSV replication have been described in WO 01/00611, WO 01/00612 and WO 01/00615.

The present invention concerns inhibitors of RSV replication, which can be represented by formula (I)

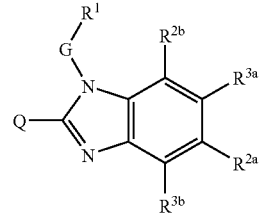

their prodrugs, N-oxides, addition salts, quaternary amines, metal complexes and stereochemically isomeric forms wherein G is a direct bond or $C_{1-10}$alkanediyl optionally substituted with one or more substituents independently selected from the group of substituents consisting of hydroxy, $C_{1-6}$alkyloxy, $Ar^1C_{1-6}$alkyloxy, $C_{1-6}$alkylthio, $Ar^1C_{1-6}$alkylthio, $HO(-CH_2-CH_2-O)_n-$, $C_{1-6}$alkyloxy$(-CH_2-CH_2-O)_n-$ or $Ar^1C_{1-6}$alkyloxy$(-CH_2-CH_2-O)_n-$;

each n independently is 1, 2, 3 or 4;

$R^1$ is $Ar^1$ or a monocyclic or bicyclic heterocycle being selected from piperidinyl, piperazinyl, pyridyl, pyrazinyl, pyridazinyl, pyrimidinyl, furanyl, tetrahydrofuranyl, thienyl, pyrrolyl, thiazolyl, oxazolyl, imidazolyl, isothiazolyl, pyrazolyl, isoxazolyl, oxadiazolyl, quinolinyl, quinoxalinyl, benzofuranyl, benzothienyl, benzimidazolyl, benzoxazolyl, benzthiazolyl, pyridopyridyl, naphthiridinyl, 1H-imidazo[4,5-b]pyridinyl, 3H-imidazo[4,5-b]pyridinyl, imidazo[1,2-a]-pyridinyl, 2,3-dihydro-1,4-dioxino[2,3-b]pyridyl or a radical of formula

(c-1)

(c-2)

(c-3)

(c-4)

(c-5)

(c-6)

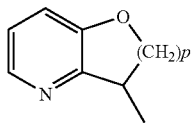

(c-7)

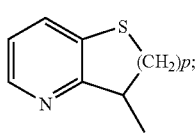

(c-8)

wherein each of said monocyclic or bicyclic heterocycles may optionally be substituted with 1 or where possible more, such as 2, 3, 4 or 5, substituents independently selected from the group of substituents consisting of halo, hydroxy, amino, cyano, carboxyl, $C_{1-6}$alkyl, $C_{1-6}$alkyloxy, $C_{1-6}$alkylthio, $C_{1-6}$alkyloxy$C_{1-6}$alkyl, $Ar^1$, $Ar^1C_{1-6}$alkyl, $Ar^1C_{1-6}$alkyloxy, hydroxy$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkylcarbonylamino, $C_{1-6}$alkyl-$SO_2$—$NR^{5c}$—, $Ar^1$—$SO_2$—$NR^{5c}$—, $C_{1-6}$alkyloxycarbonyl, —C(=O)—$NR^{5c}R^{5d}$, HO(—$CH_2$—$CH_2$—O)$_n$—, halo (—$CH_2$—$CH_2$—O)$_n$—, $C_{1-6}$alkyloxy(—$CH_2$—$CH_2$—O)$_n$—, $Ar^1C_{1-6}$alkyloxy(—$CH_2$—$CH_2$—O)$_n$— and mono- or di($C_{1-6}$alkyl)amino(—$CH_2$—$CH_2$—O)$_n$—;

each m independently is 1 or 2;
each p independently is 1 or 2;
each t independently is 0, 1 or 2;
Q is hydrogen, amino or mono- or di($C_{1-4}$alkyl)amino;
one of $R^{2a}$ and $R^{3a}$ is selected from halo, optionally mono- or polysubstituted optionally mono- or polysubstituted $C_{2-6}$alkenyl, nitro, hydroxy, $Ar^2$, $N(R^{4a}R^{4b})$, $N(R^{4a}R^{4b})$sulfonyl, $N(R^{4a}R^{4b})$carbonyl, $C_{1-6}$alkyloxy, $Ar^2$oxy, $Ar^2C_{1-6}$alkyloxy, carboxyl, $C_{1-6}$alkyloxycarbonyl, or —C(=Z)$Ar^2$; and the other one of $R^{2a}$ and $R^{3a}$ is hydrogen;
wherein
=Z is =O, =CH—C(=O)—$NR^{5a}R^{5b}$, =$CH_2$, =CH—$C_{1-6}$alkyl, =N—OH or =N—O—$C_{1-6}$alkyl; and
the optional substituents on $C_{1-6}$alkyl and $C_{2-6}$alkenyl can be the same or can be different relative to one another, and are each independently selected from the group of substituents consisting of hydroxy, cyano, halo, nitro, $N(R^{4a}R^{4b})$, $N(R^{4a}R^{4b})$sulfonyl, Het, $Ar^2$, $C_{1-6}$alkyloxy, $C_{1-6}$alkyl-S(=O)$_t$, $Ar^2$oxy, $Ar^2$—S(=O)$_t$, $Ar^2C_{1-6}$alkyloxy, $Ar^2C_{1-6}$alkyl-S(=O)$_t$, Het-oxy, Het-S(=O)$_t$, Het$C_{1-6}$alkyloxy, Het$C_{1-6}$alkyl-S(=O)$_t$, carboxyl, $C_{1-6}$alkyloxycarbonyl and —C(=Z)$Ar^2$;
in case $R^{2a}$ is different from hydrogen then $R^{2b}$ is hydrogen, $C_{1-6}$alkyl or halogen and $R^{3b}$ is hydrogen;
in case $R^{3a}$ is different from hydrogen then $R^{3b}$ is hydrogen, $C_{1-6}$alkyl or halogen and $R^{2b}$ is hydrogen;
$R^{4a}$ and $R^{4b}$ can be the same or can be different relative to one another, and are each independently selected from the group of substituents consisting of hydrogen, $C_{1-6}$alkyl, $Ar^2C_{1-6}$alkyl, ($Ar^2$)(hydroxy)$C_{1-6}$alkyl, Het-$C_{1-6}$alkyl, hydroxy$C_{1-6}$alkyl, mono- and di-($C_{1-6}$alkyloxy)$C_{1-6}$alkyl, (hydroxy$C_{1-6}$alkyl)oxy$C_{1-6}$alkyl, $Ar^1C_{1-6}$alkyloxy-$C_{1-6}$alkyl, dihydroxy$C_{1-6}$alkyl, ($C_{1-6}$alkyloxy)(hydroxy)$C_{1-6}$alkyl, ($Ar^1C_{1-6}$alkyloxy)(hydroxy)$C_{1-6}$alkyl, $Ar^1$oxy-$C_{1-6}$alkyl, ($Ar^1$oxy)(hydroxy)-$C_{1-6}$alkyl, amino$C_{1-6}$alkyl, mono- and di-($C_{1-6}$alkyl)amino-$C_{1-6}$alkyl, carboxyl-$C_{1-6}$alkyl, $C_{1-6}$alkyloxycarbonyl$C_{1-6}$alkyl, aminocarbonyl$C_{1-6}$alkyl, mono- and di($C_{1-6}$alkyl)aminocarbonyl$C_{1-6}$alkyl, $C_{1-6}$alkylcarbonyl$C_{1-6}$alkyl, ($C_{1-4}$alkyloxy)$_2$-P(=O)—$C_{1-4}$alkyl, ($C_{1-4}$alkyloxy)$_2$P(=O)—O—$C_{1-4}$alkyl, aminosulfonyl-$C_{1-6}$alkyl, mono- and di($C_{1-6}$alkyl)aminosulfonyl-$C_{1-6}$alkyl, $C_{1-6}$alkylcarbonyl, $Ar^2$carbonyl, Het-carbonyl, $Ar^2C_{1-6}$alkylcarbonyl, Het-$C_{1-6}$alkylcarbonyl, $C_{1-6}$alkylsulfonyl, aminosulfonyl, mono- and di($C_{1-6}$alkyl)aminosulfonyl, $Ar^2$sulfonyl, $Ar^2C_{1-6}$alkylsulfonyl, $Ar^2$, Het, Het-sulfonyl, Het$C_{1-6}$alkylsulfonyl;

$R^{5a}$ and $R^{5b}$ can be the same or can be different relative to one another, and are each independently hydrogen or $C_{1-6}$alkyl; or
$R^{5a}$ and $R^{5b}$ taken together may form a bivalent radical of formula —($CH_2$)$_s$— wherein s is 4 or 5;
$R^{5c}$ and $R^{5d}$ can be the same or can be different relative to one another, and are each independently hydrogen or $C_{1-6}$alkyl; or
$R^{5c}$ and $R^{5d}$ taken together may form a bivalent radical of formula —($CH_2$)$_s$— wherein s is 4 or 5;
$R^{6a}$ is hydrogen, $C_{1-6}$alkyl, $Ar^1$, $Ar^1C_{1-6}$alkyl, $C_{1-6}$alkylcarbonyl, $Ar^1$carbonyl, $Ar^1C_{1-6}$alkylcarbonyl, $C_{1-6}$alkylsulfonyl, $Ar^1$sulfonyl, $Ar^1C_{1-6}$alkylsulfonyl, $C_{1-6}$alkyloxy$C_{1-6}$alkyl, amino$C_{1-6}$alkyl, mono- or di($C_{1-6}$alkyl)amino$C_{1-6}$alkyl, hydroxy$C_{1-6}$alkyl, (carboxyl)-$C_{1-6}$alkyl, ($C_{1-6}$alkyloxycarbonyl)-$C_{1-6}$alkyl, aminocarbonyl$C_{1-6}$alkyl, mono- and di($C_{1-6}$alkyl)aminocarbonyl$C_{1-6}$alkyl, aminosulfonyl-$C_{1-6}$alkyl, mono- and di($C_{1-6}$alkyl)aminosulfonyl-$C_{1-6}$alkyl, Het, Het-$C_{1-6}$alkyl, Het-carbonyl, Het-sulfonyl, Het-$C_{1-6}$alkylcarbonyl;
$R^{6b}$ is hydrogen, $C_{1-6}$alkyl, $Ar^1$ or $Ar^1C_{1-6}$alkyl;
$R^{6c}$ is $C_{1-6}$alkyl, $Ar^1$ or $Ar^1C_{1-6}$alkyl;
$Ar^1$ is phenyl or phenyl substituted with 1 or more, such as 2, 3 or 4, substituents selected from halo, hydroxy, $C_{1-6}$alkyl, hydroxy$C_{1-6}$alkyl, polyhalo$C_{1-6}$alkyl, and $C_{1-6}$alkyloxy;
$Ar^2$ is phenyl, phenyl annelated with $C_{5-7}$cycloalkyl, or phenyl substituted with 1 or more, such as 2, 3, 4 or 5, substituents selected from halo, cyano, $C_{1-6}$alkyl, Het-$C_{1-6}$alkyl, $Ar^1$—$C_{1-6}$alkyl, cyano$C_{1-6}$alkyl, $C_{2-6}$alkenyl, cyano$C_{2-6}$alkenyl, $R^{6b}$—O—$C_{3-6}$alkenyl, $C_{2-6}$alkynyl, cyano$C_{2-6}$alkynyl, $R^{6b}$—O—$C_{3-6}$alkynyl, $Ar^1$, Het, $R^{6b}$—O—, $R^{6b}$—S—, $R^{6c}$—SO—, $R^{6c}$—SO$_2$—, $R^{6b}$—O—$C_{1-6}$alkyl-SO$_2$—, —N($R^{6a}R^{6b}$), polyhalo-$C_{1-6}$alkyl, polyhalo$C_{1-6}$alkyloxy, polyhalo$C_{1-6}$alkylthio, $R^{6c}$—C(=O)—, $R^{6b}$—O—C(O)—, N($R^{6a}R^{6b}$)—C(=O)—, $R^{6b}$—O—$C_{1-10}$alkyl, $R^{6b}$—S—$C_{1-6}$alkyl, $R^{6c}$—S(=O)$_2$—$C_{1-6}$alkyl, N($R^{6a}R^{6b}$)—$C_{1-6}$alkyl, $R^{6c}$—C(=O)—$C_{1-6}$alkyl, $R^{6b}$—O—C(=O)—$C_{1-6}$alkyl, N($R^{6a}R^{6b}$)—C(=O)—$C_{1-6}$ alkyl, $R^{6c}$—C(=O)—$NR^{6b}$—, $R^{6c}$—C(=O)—O—, $R^{6c}$—C(=O)—$NR^{6b}$—$C_{1-6}$alkyl, $R^{6c}$—C(=O)—O—$C_{1-6}$alkyl, N($R^{6a}R^{6b}$)—S(=O)$_2$—, $H_2$N—C(=NH)—;
Het is a heterocycle being selected from tetrahydrofuranyl, tetrahydrothienyl, pyrrolidinyl, pyrrolidinonyl, furanyl, thienyl, pyrrolyl, thiazolyl, oxazolyl, imidazolyl, isothiazolyl, pyrazolyl, isoxazolyl, oxadiazolyl, thiadiazolyl, piperidinyl, homopiperidinyl, piperazinyl, morpholinyl, pyridyl, pyrazinyl, pyridazinyl, pyrimidinyl, tetrahydroquinolinyl, quinolinyl, isoquinolinyl, benzodioxanyl, benzodioxolyl, indolinyl, indolyl, each of said heterocycle may optionally be substituted with oxo, amino, $Ar^1$, $C_{1-4}$alkyl, $Ar^1C_{1-4}$alkyl, mono- or di($C_{1-6}$alkyl)amino$C_{1-6}$alkyl, mono- or di($C_{1-6}$alkyl)amino, (hydroxy$C_{1-6}$alkyl) amino, and optionally further with one or two $C_{1-4}$alkyl radicals.

The invention further relates to the use of a compound of formula (I), or a prodrug, N-oxide, addition salt, quaternary amine, metal complex and stereochemically isomeric form thereof, for the manufacture of a medicament for inhibiting RSV replication. Or the invention relates to a method of inhibiting RSV replication in a warm-blooded animal said method comprising the administration of an effective amount of a compound of formula (I), or a prodrug, N-oxide, addition salt, quaternary amine, metal complex and stereochemically isomeric form thereof.

In a further aspect, this invention relates to novel compounds of formula (I) as well as methods for preparing these compounds.

The term 'prodrug' as used throughout this text means the pharmacologically acceptable derivatives, e.g. esters and amides, such that the resulting biotransformation product of the derivative is the active drug as defined in the compounds of formula (I). The reference by Goodman and Gilman (The Pharmacological Basis of Therapeutics, 8$^{th}$ ed., McGraw-Hill, Int. Ed. 1992, "Biotransformation of Drugs", p. 13-15) describing prodrugs generally, is hereby incorporated. Prodrugs are characterized by a good aqueous solubility and bioavailability, and are readily metabolized into the active inhibitors in vivo.

The terms 'polysubstituted $C_{1-6}$alkyl' and 'polysubstituted $C_{2-6}$alkenyl' such as used in the definition of $R^{2a}$ and $R^{3a}$ meant to comprise $C_{1-6}$alkyl radicals having two or more substituents, for example two, three, four, five or six substituents, in particular two or three substituents, further in particular two substituents. The upper limit of the number of substituents is determined by the number of hydrogen atoms that can be replaced as well as by the general properties of the substituents such as their bulkiness, these properties allowing the skilled person to determine said upper limit.

The term '$C_{1-10}$alkanediyl optionally substituted with one or more substituents' as used in the definition of G is meant to comprise $C_{1-10}$alkanediyl radicals having no, one, two or more substituents, for example no, one, two, three, four, five or six substituents, in particular no, one, two or three substituents, further in particular no, one or two substituents. Also here, the upper limit of the number of substituents is determined by the factors mentioned above.

As used in the foregoing and hereinafter, 'polyhalo$C_{1-6}$ alkyl' as a group or part of a group, e.g. in polyhalo$C_{1-6}$ alkyloxy, is defined as mono- or polyhalo substituted $C_{1-6}$alkyl, in particular $C_{1-6}$alkyl substituted with up to one, two, three, four, five, six, or more halo atoms, such as methyl or ethyl with one or more fluoro atoms, for example, difluoromethyl, trifluoromethyl, trifluoroethyl. Also included are perfluoro $C_{1-6}$alkyl groups, which are $C_{1-6}$alkyl groups wherein all hydrogen atoms are replaced by fluoro atoms, e.g. pentafluoroethyl. In case more than one halogen atom is attached to an alkyl group within the definition of polyhalo$C_{1-4}$ alkyl, the halogen atoms may be the same or different.

Each of the monocyclic or bicyclic heterocycles in the definition of $R^1$ may optionally be substituted with 1 or where possible more substituents, such as 2, 3, 4 or 5, substituents. In particular, said heterocycles may optionally be substituted with up to 4, up to 3, up to 2 substituents, or up to 1 substituent.

Each $Ar^1$ or $Ar^2$ may be unsubstituted phenyl or phenyl substituted with 1 or more substituents, such as 5 or 4 substituents or, which is preferred, up to 3 substituents, or up to two substituents, or with one substituent.

A radical '$R^{6b}$—O—$C_{3-6}$alkenyl' or '$R^{6b}$—O—$C_{3-6}C_{3-6}$ alkynyl' such as mentioned among the substituents of $Ar^2$ in particular has the $R^{6b}$—O— group on a saturated carbon atom.

A hydroxy$C_{1-6}$alkyl group when substituted on an oxygen atom or a nitrogen atom preferably is a hydroxy$C_{2-6}$alkyl group wherein the hydroxy group and the oxygen or nitrogen is separated by at least two carbon atoms.

A dihydroxy$C_{1-6}$alkyl group as mentioned for example in the definition of $R^{4a}$ and $R^{4b}$, is a $C_{1-6}$alkyl group having two hydroxy substituents which in particular are substituted on different carbon atoms. The terms ($C_{1-6}$alkyloxy)(hydroxy)$C_{1-6}$alkyl, di($C_{1-6}$alkyloxy)$C_{1-6}$alkyl, ($Ar^1C_{1-6}$alkyloxy)(hydroxy)$C_{1-6}$alkyl refer to a $C_{1-6}$alkyl radical substitute with as well a $C_{1-6}$alkyloxy and a hydroxy group, with two $C_{1-6}$alkyloxy groups, and with a $Ar^1C_{1-6}$alkyloxy and a hydroxy group, respectively. Preferably in these radicals the substituents on the $C_{1-6}$alkyl group are on a carbon atom other than the carbon linked to the nitrogen atom to which $R^{4a}$ and/or $R^{4b}$ are linked.

As used herein $C_{1-3}$alkyl as a group or part of a group defines straight or branched chain saturated hydrocarbon radicals having from 1 to 3 carbon atoms such as methyl, ethyl, propyl, 1-methylethyl and the like; $C_{1-4}$alkyl as a group or part of a group defines straight or branched chain saturated hydrocarbon radicals having from 1 to 4 carbon atoms such as the group defined for $C_{1-3}$alkyl and butyl and the like; $C_{2-4}$alkyl as a group or part of a group defines straight or branched chain saturated hydrocarbon radicals having from 2 to 4 carbon atoms such as ethyl, propyl, 1-methylethyl, butyl and the like; $C_{1-6}$alkyl as a group or part of a group defines straight or branched chain saturated hydrocarbon radicals having from 1 to 6 carbon atoms such as the groups defined for $C_{1-4}$alkyl and pentyl, hexyl, 2-methylbutyl and the like; $C_{1-9}$alkyl as a group or part of a group defines straight or branched chain saturated hydrocarbon radicals having from 1 to 9 carbon atoms such as the groups defined for $C_{1-6}$alkyl and heptyl, octyl, nonyl, 2-methylhexyl, 2-methylheptyl and the like; $C_{1-10}$alkyl as a group or part of a group defines straight or branched chain saturated hydrocarbon radicals having from 1 to 10 carbon atoms such as the groups defined for $C_{1-9}$alkyl and decyl, 2-methylnonyl and the like.

The term '$C_{3-6}$alkenyl' used herein as a group or part of a group is meant to comprise straight or branched chain unsaturated hydrocarbon radicals having at least one double bond, and preferably having one double bond, and from 3 to 6 carbon atoms such as propenyl, buten-1-yl, buten-2-yl, penten-1-yl, penten-2-yl, hexen-1-yl, hexen-2-yl, hexen-3-yl, 2-methylbuten-1-yl, and the like. The term '$C_{2-6}$alkenyl' used herein as a group or part of a group is meant to comprise $C_{3-6}$alkenyl groups and ethylene. The term '$C_{3-6}$alkynyl' defines straight or branched chain unsaturated hydrocarbon radicals having one triple bond and from 3 to 6 carbon atoms such as propenyl, butyn-1-yl, butyn-2-yl, pentyn-1-yl, pentyn-2-yl, hexyn-1-yl, hexyn-2-yl, hexyn-3-yl, 2-methylbutyn-1-yl, and the like. The term '$C_{2-6}$alkynyl' used herein as a group or part of a group is meant to comprise $C_{3-6}$alkynyl groups and ethynyl.

Whenever a $C_{2-6}$alkenyl group is linked to a heteroatom it preferably is linked via a saturated carbon atom. Whenever a $C_{3-6}$alkenyl group is substituted with hydroxy, the hydroxy is on a saturated carbon atom.

$C_{3-7}$cycloalkyl is generic to cyclopropyl, cyclobutyl, cyclopentyl, cyclohexyl or cycloheptyl. $C_{5-7}$cycloalkyl is generic to cyclopentyl, cyclohexyl or cycloheptyl.

$C_{2-5}$alkanediyl defines bivalent straight and branched chain saturated hydrocarbon radicals having from 2 to 5 carbon atoms such as, for example, 1,2-ethanediyl, 1,3-propanediyl, 1,4-butanediyl, 1,2-propanediyl, 2,3-butanediyl, 1,5-pentanediyl and the like, $C_{1-4}$alkanediyl defines bivalent straight and branched chain saturated hydrocarbon radicals having from 1 to 4 carbon atoms such as, for example, methylene, 1,2-ethanediyl, 1,3-propanediyl, 1,4-butanediyl and the like; $C_{1-6}$alkanediyl is meant to include $C_{1-4}$alkanediyl and the higher homologues thereof having from 5 to 6 carbon atoms such as, for example, 1,5-pentanediyl, 1,6-hexanediyl and the like;

$C_{1-10}$alkanediyl is meant to include $C_{1-6}$alkanediyl and the higher homologues thereof having from 7 to 10 carbon atoms such as, for example, 1,7-heptanediyl, 1,8-octanediyl, 1,9-nonanediyl, 1,10-decanediyl and the like.

As used herein before, the term (═O) forms a carbonyl moiety when attached to a carbon atom, a sulfoxide moiety when attached to a sulfur atom and a sulfonyl moiety when two of said terms are attached to a sulfur atom. The term (═N—OH) forms a hydroxyimine moiety when attached to a carbon atom.

The term halo is generic to fluoro, chloro, bromo and iodo.

It should be noted that the radical positions on any molecular moiety used in the definitions may be anywhere on such moiety as long as it is chemically stable.

Radicals used in the definitions of the variables include all possible isomers unless otherwise indicated. For instance pyridyl includes 2-pyridyl, 3-pyridyl and 4-pyridyl; pentyl includes 1-pentyl, 2-pentyl and 3-pentyl.

The term polysubstituted is defined as substituted with more than one substituent.

When any variable occurs more than one time in any constituent, each definition is independent.

Whenever used hereinafter, the term "compounds of formula (I)", or "the present compounds" or similar term is meant to include the compounds of general formula (I), their prodrugs, N-oxides, addition salts, quaternary amines, metal complexes and stereochemically isomeric forms. An interesting subgroup of the compounds of formula (I) or any subgroup thereof are the N-oxides, salts and all the stereoisomeric forms of the compounds of formula (I).

It will be appreciated that some of the compounds of formula (I) may contain one or more centers of chirality and exist as stereochemically isomeric forms.

The term "stereochemically isomeric forms" as used hereinbefore defines all the possible compounds made up of the same atoms bonded by the same sequence of bonds but having different three-dimensional structures which are not interchangeable, which the compounds of formula (I) may possess.

Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods that may advantageously be employed are, for example, selective crystallization and chromatography, e.g. column chromatography.

For some of the compounds of formula (I), their prodrugs, N-oxides, salts, solvates, quaternary amines, or metal complexes and the intermediates used in the preparation thereof, the absolute stereochemical configuration was not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates, which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several nitrogen atoms are oxidized to the so-called N-oxide.

It will be appreciated that the compounds of formula (I) may have metal binding, chelating, complexating properties and therefore may exist as metal complexes or metal chelates. Such metalated derivatives of the compounds of formula (I) are intended to be included within the scope of the present invention.

Some of the compounds of formula (I) may also exist in their tautomeric form. Such forms although not explicitly indicated in the above formula are intended to be included within the scope of the present invention.

One embodiment of the present invention concerns compounds of formula (I-a):

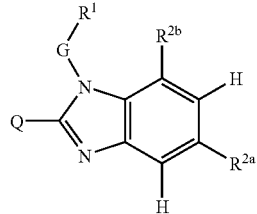

(I-a)

wherein Q, G, $R^1$, $R^{2a}$, $R^{2b}$ are as specified in the definitions of the compounds of formula (I) or any of the subgroups of compounds of formula (I) specified herein.

Another embodiment of the present invention concerns compounds of formula (I-b):

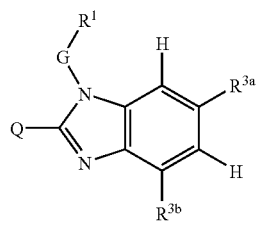

(I-b)

wherein Q, G, $R^1$, $R^{3a}$, $R^{3b}$ are as specified in the definitions of the compounds of formula (I) or any of the subgroups of compounds of formula (I) specified herein.

One particular embodiment of the present invention concerns compounds of formula (I-a-1):

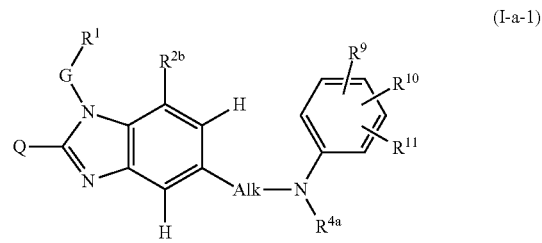

(I-a-1)

wherein Q G, $R^1$, $R^{4a}$ and $R^{2b}$ are as specified in the definitions of the compounds of formula (I) or any of the subgroups of compounds of formula (I) specified herein; and Alk is $C_{1-6}$alkanediyl;

$R^9$, $R^{10}$, $R^{11}$ independently from one another have the same meanings as the substituents on $Ar^2$ as specified in the definitions of the compounds of formula (I) or of any of the subgroups thereof; and $R^{10}$ and/or $R^{11}$ may also be hydrogen.

Another particular embodiment of the present invention concerns compounds of formula (I-b-1):

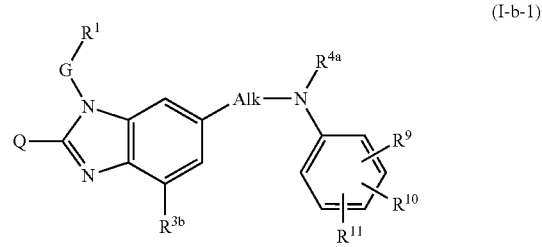

(I-b-1)

wherein Q, G, $R^1$, $R^{4a}$ and $R^{3b}$ are as specified in the definitions of the compounds of formula (I) or any of the subgroups of compounds of formula (I) specified herein; and Alk is $C_{1-6}$alkanediyl;

$R^9$, $R^{10}$, $R^{11}$ independently from one another have the same meanings as the substituents on $Ar^2$ as specified in the definitions of the compounds of formula (I) or of any of the subgroups thereof; and $R^{10}$ and/or $R^{11}$ may also be hydrogen.

Interesting subgroups are those comprising compounds of formulae:

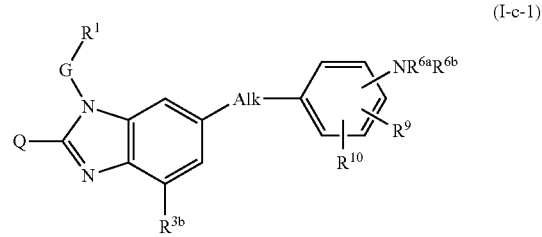

(I-c-1)

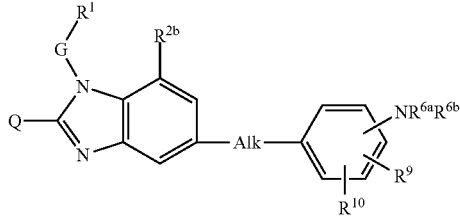

(I-c-2)

wherein in (I-c-1) and (I-c-2) the radicals G, $R^1$, $R^{2b}$, $R^{3b}$ are as specified in the definitions of the compounds of formula (I) or any of the subgroups of compounds of formula (I) specified herein; the radicals Alk, $R^9$, $R^{10}$, $R^{11}$ are as specified above or in any of the subgroups of compounds of formula (I) specified herein; and the radicals $R^{6a}$ and $R^{6b}$ are as specified in the definitions of the compounds of formula (I) or any of the subgroups of compounds of formula (I) specified herein.

Preferred subgroups are those wherein Alk is ethylene or methylene, more preferably wherein Alk is methylene.

In (I-a-1) or (I-b-1) $R^{4a}$ preferably is hydrogen, hydroxy$C_{1-6}$ alkyl, aminocarbonyl-$C_{1-6}$alkyl.

In (I-a-1), (I-b-1), (I-c-1) or (I-c-2) the radicals $R^9$, $R^{10}$, $R^{11}$ preferably and independently from one another are $C_{1-6}$alkyl or $R^{6b}$—O—$C_{1-6}$alkyl; and $R^{10}$ and/or $R^{11}$ may also be hydrogen; or $R^9$, $R^{10}$ more preferably and independently from one another are $C_{1-6}$alkyl or $R^{6b}$—O—$C_{1-6}$alkyl; and $R^{11}$ is hydrogen; or $R^9$, $R^{10}$ still more preferably are $C_{1-6}$alkyl and $R^{11}$ is hydrogen; or $R^9$ is $C_{1-6}$alkyl, $R^{10}$ is $R^{6b}$—O—$C_{1-6}$alkyl and $R^{11}$ is hydrogen.

It is to be understood that the above defined subgroups of compounds of formulae (I-a), (I-b), etc. as well as any other subgroup defined herein are meant to also comprise any prodrugs, N-oxides, addition salts, quaternary amines, metal complexes and stereochemically isomeric forms of such compounds.

Interesting compounds are those compounds of formula (I) or any subgroup thereof wherein G is $C_{1-10}$alkanediyl; more in particular, wherein G is methylene.

One embodiment comprises compounds of formula (I), as defined above or as in any of the subgroups specified herein wherein Q is hydrogen. Another embodiment is comprises compounds of formula (I), as defined above or as in any of the subgroups specified herein wherein Q is amino; or wherein Q is other than hydrogen, i.e. wherein Q is amino, mono- or di-($C_{1-6}$alkyl)amino.

Particular subgroups of the compounds of formula (I) are those compounds of formula (I), or any subgroup of compounds of formula (I) specified herein, wherein G is $C_{1-10}$alkanediyl, more in particular wherein G is methylene.

Other particular subgroups of the compounds of formula (I) are those compounds of formula (I), or any subgroup of compounds of formula (I) specified herein, wherein (a) $R^1$ is other than $Ar^1$; or wherein (b) $R^1$ is $Ar^1$ or a monocyclic heterocycle, which is as specified in the definitions of the compounds of formula (I) or any of the subgroups thereof.

Further particular subgroups of the compounds of formula (I) are those compounds of formula (I), or any subgroup of compounds of formula (I) specified herein, wherein (c) $R^1$ is pyridyl optionally substituted with 1 or 2 substituents independently selected from the group consisting of halo, hydroxy, amino, cyano, carboxyl, $C_{1-6}$alkyl, $C_{1-6}$alkyloxy, $C_{1-6}$alkylthio, $C_{1-6}$alkyloxy$C_{1-6}$alkyl, $Ar^1$, $Ar^1C_{1-6}$alkyl, $Ar^1C_{1-6}$alkyloxy, hydroxy$C_{1-6}$alkyl, mono- or di($C_{1-6}$alkyl)amino, mono- or di($C_{1-6}$alkyl)amino-$C_{1-6}$alkyl, polyhalo$C_{1-6}$alkyl, $C_{1-6}$alkylcarbonylamino, $C_{1-6}$alkyl-$SO_2$—$NR^{4a}$—, $Ar^1$—$SO_2$—$NR^{4a}$—, $C_{1-6}$alkyloxycarbonyl, —C(=O)—$NR^{4a}R^{4b}$, HO(—$CH_2$—$CH_2$—O)$_n$—, halo(—$CH_2$—$CH_2$—O)$_n$—, $C_{1-6}$alkyloxy(—$CH_2$—$CH_2$—O)$_n$—, $Ar^1C_{1-6}$alkyloxy(—$CH_2$—$CH_2$—O)$_n$— and mono- or di($C_{1-6}$alkyl)amino(—$CH_2$—$CH_2$—O)$_n$—; or more in particular (d) $R^1$ is pyridyl substituted with 1 or 2 substituents independently selected from the group consisting of hydroxy, $C_{1-6}$alkyl, halo, $C_{1-6}$alkyloxy, $Ar^1C_{1-6}$alkyloxy and ($C_{1-6}$alkyloxy)$C_{1-6}$alkyloxy; preferably wherein (e) $R^1$ is pyridyl substituted with 1 or 2 substituents independently selected from the group consisting of hydroxy, $C_{1-6}$alkyl, halo and $C_{1-6}$alkyloxy; or wherein (f) $R^1$ is pyridyl substituted with 1 or 2 substituents independently selected from the group consisting of hydroxy and $C_{1-6}$alkyl; more preferably wherein (g) $R^1$ is pyridyl substituted with hydroxy and $C_{1-6}$alkyl; or more preferably wherein (h) $R^1$ is pyridyl substituted with hydroxy and methyl; or wherein (i) $R^1$ is 3-hydroxy-6-methylpyrid-2-yl.

Further embodiments comprise those compounds of formula (I) or any of the subgroups of compounds of formula (I) wherein (j) $R^1$ is $Ar^1$, quinolinyl, benzimidazolyl, a radical of formula

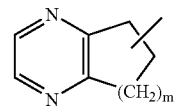

(c-4)

pyrazinyl, or pyridyl; or wherein (k) $R^1$ is $Ar^1$, quinolinyl, benzimidazolyl or a radical of formula (c-4) wherein m is 2, pyrazinyl, or pyridyl;

wherein each of the radicals in (j) and (k) may optionally be substituted with the substituents specified in the definition of the compounds of formula (I) and in particular pyridyl may be substituted as specified above in (a) to (i).

Further embodiments comprise those compounds of formula (I) or any of the subgroups of compounds of formula (I) wherein (l) $R^1$ is $Ar^1$, quinolinyl, benzimidazolyl or a radical of formula (c-4) wherein m is 2, pyrazinyl, or pyridyl, wherein each of these radicals may optionally be substituted with one, two or three radicals selected from the group consisting of halo, hydroxy, $C_{1-6}$alkyl, $C_{1-6}$alkyloxy, $Ar^1C_{1-6}$alkyloxy, ($C_{1-6}$alkyloxy)$C_{1-6}$alkyloxy; or more specifically wherein (m) $R^1$ is $Ar^1$, quinolinyl, benzimidazolyl or a radical of formula (c-4) wherein m is 2, pyrazinyl, or pyridyl, wherein each of these radicals may optionally be substituted with one, two or three radicals selected from the group consisting of halo, hydroxy, $C_{1-6}$alkyloxy, benzyloxy; or more specifically wherein (n) $R^1$ is phenyl optionally substituted with one, two or three radicals selected from the group consisting of halo, hydroxy, $C_{1-6}$alkyl, $C_{1-6}$alkyloxy; quinolinyl; a radical (c-4) wherein m is 2, optionally substituted with up to two radicals selected from $C_{1-6}$alkyl; benzimidazolyl optionally substituted with $C_{1-6}$alkyl; pyridyl optionally substituted with one or two radicals selected from hydroxy, halo, $C_{1-6}$alkyl, benzyloxy and $C_{1-6}$alkyloxy, pyrazinyl optionally substituted with up to three radicals selected from $C_{1-6}$alkyl; or pyridyl substituted or optionally substituted as specified above in (a)-(i); or wherein (o) $R^1$ is phenyl optionally substituted with one or two radicals selected from the group consisting of halo, hydroxy, $C_{1-6}$alkyl, $C_{1-6}$alkyloxy;

(p) $R^1$ is quinolinyl;

(q) $R^1$ is a radical (c-4) wherein m is 2, optionally substituted with up to two radicals selected from $C_{1-6}$alkyl;

(r) $R^1$ is benzimidazolyl optionally substituted with $C_{1-6}$alkyl; pyridyl optionally substituted with one or two radicals selected from hydroxy, halo, $C_{1-6}$alkyl, benzyloxy and $C_{1-6}$alkyloxy, (s) $R^1$ is pyrazinyl optionally substituted with up to three radicals selected from $C_{1-6}$alkyl.

Preferred subgroups of compounds of formula (I) or any of the subgroups of compounds of formula (I) are those wherein G is a direct bond or methylene and $R^1$ is as specified above in (a)-(s). Further preferred are the compounds of formula (I) or any of the subgroups specified herein wherein G is a direct bond and $R^1$ is a radical (c-4), in particular wherein m is 2, optionally substituted with up to two radicals selected from $C_{1-6}$alkyl. Further preferred are the compounds of formula (I) or any of the subgroups specified herein wherein or G is methylene and $R^1$ is as specified above in (a)-(s), but is other than a radical (c-4).

Other subgroups of the compounds of formula (I) are those compounds of formula (I), or any subgroup of compounds of formula (I) specified herein, wherein (a) $R^{4a}$ and $R^{4b}$ are each independently selected from hydrogen, $C_{1-6}$alkyl, $Ar^2C_{1-6}$alkyl, $(Ar^2)$(hydroxy)$C_{1-6}$alkyl, Het-$C_{1-6}$alkyl, hydroxy$C_{1-6}$alkyl, mono- and di-$(C_{1-6}$alkyloxy)$C_{1-6}$alkyl, (hydroxy$C_{1-6}$alkyl)oxy$C_{1-6}$alkyl, $Ar^1C_{1-6}$alkyloxy-$C_{1-6}$alkyl, dihydroxy$C_{1-6}$alkyl, $(C_{1-6}$alkyloxy)(hydroxy)$C_{1-6}$alkyl, $(Ar^1C_{1-6}$alkyloxy)(hydroxy)$C_{1-6}$alkyl, $Ar^1$oxy$C_{1-6}$alkyl, $(Ar^1$oxy)(hydroxy)-$C_{1-6}$alkyl, amino$C_{1-6}$alkyl, mono- and di($C_{1-6}$alkyl)amino-$C_{1-6}$alkyl, carboxyl$C_{1-6}$alkyl, $C_{1-6}$alkyloxycarbonyl-$C_{1-6}$alkyl, aminocarbonyl$C_{1-6}$alkyl, mono- and di($C_{1-6}$alkyl)aminocarbonyl-$C_{1-6}$alkyl, $C_{1-6}$alkylcarbonyl$C_{1-6}$alkyl, $(C_{1-4}$alkyloxy)$_2$P(=O)—$C_{1-6}$alkyl, $(C_{1-4}$alkyloxy)$_2$P(=O)—O—$C_{1-6}$alkyl, aminosulfonyl-$C_{1-6}$alkyl, mono- and di($C_{1-6}$alkyl)-aminosulfonyl-$C_{1-6}$alkyl, $C_{1-6}$alkylcarbonyl, $Ar^2$carbonyl, Het-carbonyl, $Ar^2C_{1-6}$ alkylcarbonyl, Het-$C_{1-6}$alkylcarbonyl, $Ar^2$ and Het; or wherein (b) $R^{4a}$ and $R^{4b}$ are each independently selected from hydrogen, $C_{1-6}$alkyl, $Ar^2C_{1-6}$alkyl, $(Ar^2)$(hydroxy)$C_{1-6}$alkyl, Het-$C_{1-6}$alkyl, hydroxy$C_{1-6}$alkyl, mono- and di-$(C_{1-6}$alkyloxy)$C_{1-6}$alkyl, (hydroxy$C_{1-6}$alkyl)oxy$C_{1-6}$alkyl, $Ar^1C_{1-6}$alkyloxy-$C_{1-6}$alkyl, dihydroxy$C_{1-6}$alkyl, $(C_{1-6}$alkyloxy)hydroxy)$C_{1-6}$alkyl, $(Ar^1C_{1-6}$alkyloxy)(hydroxy)$C_{1-6}$alkyl, $Ar^1$oxy-$C_{1-6}$alkyl, $(Ar^1$oxy)hydroxy)-$C_{1-6}$alkyl, amino$C_{1-6}$ alkyl, mono- and di($C_{1-6}$alkyl)amino-$C_{1-6}$alkyl, carboxyl-$C_{1-6}$alkyl, $C_{1-6}$alkyloxycarbonyl$C_{1-6}$alkyl, aminocarbonyl$C_{1-6}$alkyl, mono- and di($C_{1-6}$alkyl)aminocarbonyl$C_{1-6}$alkyl, $C_{1-6}$alkylcarbonyl$C_{1-6}$alkyl, $(C_{1-4}$alkyloxy)$_2$-P(=O)—$C_{1-6}$alkyl, $(C_{1-4}$alkyloxy)$_2$-P(=O)—O—$C_{1-6}$alkyl, aminosulfonyl-$C_{1-6}$alkyl, mono- and di($C_{1-6}$alkyl)aminosulfonyl-$C_{1-6}$alkyl, $Ar^2$ and Het; or wherein (c) $R^{4a}$ and $R^{4b}$ are each independently selected from hydrogen, $C_{1-6}$alkyl, $Ar^2C_{1-6}$alkyl, $(Ar^2)$(hydroxy)$C_{1-6}$alkyl, Het-$C_{1-6}$alkyl, hydroxy$C_{1-6}$alkyl, $(C_{1-6}$alkyloxy)$C_{1-6}$alkyl, (hydroxy$C_{1-6}$alkyl)oxy$C_{1-6}$alkyl, $Ar^1C_{1-6}$alkyloxy-$C_{1-6}$alkyl, $Ar^1$oxy-$C_{1-6}$alkyl, $(Ar^1$oxy)(hydroxy)-$C_{1-6}$alkyl, amino$C_{1-6}$alkyl, mono- and di($C_{1-6}$alkyl)amino-$C_{1-6}$alkyl, carboxyl$C_{1-6}$alkyl, $C_{1-6}$alkyloxycarbonyl-$C_{1-6}$alkyl, aminocarbonyl$C_{1-6}$alkyl, mono- and di($C_{1-6}$alkyl)aminocarbonyl-$C_{1-6}$alkyl, $(C_{1-4}$alkyloxy)$_2$P(=O)—$C_{1-6}$alkyl, $(C_{1-4}$alkyloxy)$_2$P(=O)—O—$C_{1-6}$alkyl, aminosulfonyl-$C_{1-6}$alkyl, mono- and di($C_{1-6}$alkyl)aminosulfonyl-$C_{1-6}$alkyl and $Ar^1$; or wherein (d) $R^{4a}$ and $R^{4b}$ are each independently selected from hydrogen, $C_{1-6}$alkyl, $(Ar^2)$(hydroxy)$C_{1-6}$alkyl, Het-$C_{1-6}$alkyl, hydroxy$C_{1-6}$alkyl, $(C_{1-6}$allyloxy)$C_{1-6}$alkyl, (hydroxy$C_{1-6}$alkyl)oxy$C_{1-6}$alkyl, $Ar^1C_{1-6}$alkyloxy-$C_{1-6}$alkyl, $Ar^1$oxy$C_{1-6}$alkyl, $(Ar^1$oxy)(hydroxy)-$C_{1-6}$alkyl, amino$C_{1-6}$ alkyl, mono- and di($C_{1-6}$alkyl)amino-$C_{1-6}$alkyl, carboxyl$C_{1-6}$alkyl, aminocarbonyl$C_{1-6}$alkyl, mono- and di($C_{1-6}$alkyl)-aminocarbonyl$C_{1-6}$alkyl, $(C_{1-4}$alkyloxy)$_2$P(=O)—$C_{1-6}$alkyl, $(C_{1-4}$alkyloxy)$_2$-P(=O)—O—$C_{1-6}$alkyl, aminosulfonyl-$C_{1-6}$alkyl, mono- and di($C_{1-6}$alkyl)aminosulfonyl-$C_{1-6}$alkyl and $Ar^1$.

Interesting subgroups of the compounds of formula (I) are those compounds of formula (I), or any subgroup of compounds of formula (I) specified herein, wherein (e) $R^{4a}$ and $R^{4b}$ are each independently selected from hydrogen, morpholinyl-$C_{1-6}$alkyl, hydroxy$C_{1-6}$alkyl, $(C_{1-6}$alkyloxy)$C_{1-6}$alkyl, amino$C_{1-6}$alkyl, mono- and di($C_{1-6}$alkyl)amino-$C_{1-6}$alkyl, carboxyl$C_{1-6}$alkyl, aminocarbonyl$C_{1-6}$ alkyl, mono- and di($C_{1-6}$alkyl)aminocarbonyl$C_{1-6}$alkyl, aminosulfonyl-$C_{1-6}$alkyl, mono- and di($C_{1-6}$alkyl)aminosulfonyl-$C_{1-6}$alkyl and $Ar^1$; or wherein (f) $R^{4a}$ and $R^{4b}$ are each independently selected from hydrogen, hydroxy$C_{1-6}$alkyl, $(C_{1-6}$alkyloxy)$C_{1-6}$alkyl, amino$C_{1-6}$alkyl, mono- and di($C_{1-6}$alkyl)amino-$C_{1-6}$alkyl, carboxyl$C_{1-6}$alkyl, aminocarbonyl$C_{1-6}$alkyl, mono- and di($C_{1-6}$alkyl)aminocarbonyl-$C_{1-6}$alkyl; or wherein (g) $R^{4a}$ and $R^{4b}$ are each independently selected from hydrogen, hydroxy$C_{1-6}$alkyl, aminocarbonyl$C_{1-6}$alkyl, mono- and di($C_{1-6}$alkyl)aminocarbonyl$C_{1-6}$alkyl; or wherein (h) $R^{4a}$ and $R^{4b}$ are each independently selected from hydrogen, hydroxy$C_{1-6}$alkyl and aminocarbonyl$C_{1-6}$alkyl.

Other interesting subgroups of the compounds of formula (I) are those compounds of formula (I), or any subgroup of compounds of formula (I) specified herein, wherein $R^{4a}$ is hydrogen and $R^{4b}$ is as specified above in the restricted definitions (a) to (h).

Other subgroups of the compounds of formula (I) are those compounds of formula (I), or any subgroup of compounds of formula (I) specified herein, wherein (a) $Ar^2$ is phenyl, phenyl annelated with $C_{5-7}$cycloalkyl, or phenyl substituted with 1, 2, or 3 substituents selected from halo, cyano, $C_{1-6}$alkyl, Het-$C_{1-6}$alkyl, $Ar^1$—$C_{1-6}$alkyl, cyano$C_{1-6}$alkyl, $C_{2-6}$alkenyl, cyano$C_{2-6}$alkenyl, $R^{6b}$—O—$C_{3-6}$alkenyl, $C_{2-6}$alkynyl, cyano$C_{2-6}$alkynyl, $R^{6b}$—O—$C_{3-6}$alkynyl, $Ar^1$, Het, $R^{6b}$—O—, $R^{6b}$—S—, $R^{6c}$—SO—, $R^{6c}$—SO$_2$—, $R^{6b}$—O—$C_{1-6}$alkyl-SO$_2$—, —N($R^{6a}R^{6b}$), CF$_3$, CF$_3$-oxy, CF$_3$-thio, $R^{6c}$—C(=O)—, $R^{6b}$—O—C(=O)—, N($R^{6a}R^{6b}$)—C(=O)—, $R^{6b}$—O—$C_{1-6}$alkyl, $R^{6b}$—S—$C_{1-6}$alkyl, $R^{6c}$—S(=O)$_2$—$C_{1-6}$alkyl, N($R^{6a}R^{6b}$)—$C_{1-6}$alkyl, $R^{6c}$—C(=O)—$C_{1-6}$alkyl, $R^{6b}$—O—C(=O)—$C_{1-6}$alkyl, N($R^{6a}R^{6b}$)—C(=O)—$C_{1-6}$ alkyl, $R^{6c}$—C(=O)—NR$^{6b}$—, $R^{6c}$—C(=O)—O—, $R^{6c}$—C(=O)—NR$^{6b}$—$C_{1-6}$alkyl, $R^{6c}$—C(=O)—O—$C_{1-6}$alkyl, N($R^{6a}R^{6b}$)—S(=O)—, H$_2$N—C(=NH)—;

(b) $Ar^2$ is phenyl, phenyl annelated with $C_{5-7}$cycloalkyl, or phenyl substituted with 1, 2, or 3 substituents, or with 1 or 2 substituents, selected from halo, cyano, $C_{1-6}$alkyl, Het-$C_{1-6}$alkyl, $Ar^1$—$C_{1-6}$alkyl, cyano$C_{1-6}$alkyl, $C_{2-6}$alkenyl, cyano-$C_{2-6}$alkenyl, $R^{6b}$—O—$C_{3-6}$alkenyl, $C_{2-6}$alkynyl, cyano$C_{2-6}$alkynyl, $R^{6b}$—O—$C_{3-6}$alkynyl, $Ar^1$, Het, $R^{6b}$—

O—, $R^{6b}$—S—, $R^{6c}$—SO—, $R^{6c}$—SO$_2$—, $R^{6b}$—O—C$_{1-6}$alkyl-SO$_2$—, —N($R^{6a}R^{6b}$), CF$_3$, $R^{6c}$—C(=O)—, $R^{6b}$—O—C(=O)—, N($R^{6a}R^{6b}$)—C(=O)—, $R^{6b}$—O—C$_{1-6}$alkyl, $R^{6b}$—S—C$_{1-6}$alkyl, $R^{6c}$—S(=O)$_2$—C$_{1-6}$alkyl, N($R^{6a}R^{6b}$)—C$_{1-6}$alkyl, $R^{6c}$—C(=O)—C$_{1-6}$alkyl, $R^{6b}$—O—C(=O)—C$_{1-6}$alkyl, N($R^{6a}R^{6b}$)—C(=O)—C$_{1-6}$alkyl, $R^{6c}$—C(=O)—NR$^{6b}$—, H$_2$N—C(=NH)—;

(c) Ar$^2$ is phenyl, phenyl annelated with C$_{5-7}$cycloalkyl, or phenyl substituted with 1, 2, or 3, or with 1 or 2, substituents selected from halo, cyano, C$_{1-6}$alkyl, Het-C$_{1-6}$alkyl, Ar$^1$—C$_{1-6}$alkyl, cyanoC$_{1-6}$alkyl, C$_{2-6}$alkenyl, cyanoC$_{2-6}$alkenyl, $R^{6b}$—O—C$_{3-6}$alkenyl, C$_{2-6}$alkynyl, cyanoC$_{2-6}$alkynyl, $R^{6b}$—O—C$_{3-6}$alkynyl, Ar$^1$, Het, $R^{6b}$—O—, $R^{6b}$—S—, $R^{6c}$—SO$_2$—, —N($R^{6a}R^{6b}$), CF$_3$, $R^{6b}$—O—C(=O)—, N($R^{6a}R^{6b}$)—C(=O)—, $R^{6b}$—O—C$_{1-6}$alkyl, $R^{6b}$—S—C$_{1-6}$alkyl, $R^{6c}$—S(=O)$_2$—C$_{1-6}$alkyl, N($R^{6a}R^{6b}$)—C$_{1-6}$alkyl, $R^{6c}$—C(=O)—C$_{1-6}$alkyl, $R^{6b}$—O—C(=O)—C$_{1-6}$alkyl, N($R^{6a}R^{6b}$)—C(=O)—C$_{1-6}$alkyl, $R^{6c}$—C(=O)—NR$^{6b}$—;

(d) Ar$^2$ is phenyl, phenyl annelated with C$_{5-7}$cycloalkyl, or phenyl substituted with 1, 2, or 3, or with 1 or 2, substituents selected from C$_{1-6}$alkyl, Het-C$_{1-6}$alkyl, Ar$^1$—C$_{1-6}$alkyl, cyanoC$_{1-6}$alkyl, C$_{2-6}$alkenyl, cyanoC$_{2-6}$alkenyl, $R^{6b}$—O—C$_{3-6}$alkenyl, C$_{2-6}$alkynyl, cyanoC$_{2-6}$alkynyl, $R^{6b}$—O—C$_{3-6}$alkynyl, $R^{6b}$—O—C$_{1-6}$alkyl, $R^{6c}$—S(=O)$_2$—C$_{1-6}$alkyl, N($R^{6a}R^{6b}$)—C$_{1-6}$alkyl, $R^{6b}$—O—C(=O)—C$_{1-6}$alkyl, N($R^{6a}R^{6b}$)—C(=O)—C$_{1-6}$alkyl;

(e) Ar$^2$ is phenyl, or phenyl substituted with 1, 2, or 3 substituents, or with 1 or 2 substituents, selected from C$_{1-6}$alkyl, Het-C$_{1-6}$alkyl, Ar$^1$—C$_{1-6}$alkyl, cyanoC$_{1-6}$alkyl, C$_{2-6}$alkenyl, cyanoC$_{2-6}$alkenyl, hydroxy-C$_{3-6}$alkenyl, C$_{2-6}$alkynyl, cyanoC$_{2-6}$alkynyl, hydroxy-C$_{3-6}$alkynyl, $R^{6b}$—O—C$_{1-6}$alkyl, amino-S(=O)$_2$—C$_{1-6}$alkyl, N($R^{6a}R^{6b}$)—C$_{1-6}$alkyl, $R^{6b}$—O—C(=O)—C$_{1-6}$alkyl, amino-C(=O)—C$_{1-6}$alkyl, mono- and di-C$_{1-6}$alkyl amino-C(=O)—C$_{1-6}$alkyl;

(f) Ar$^2$ is phenyl, or phenyl substituted with 1, 2, or 3 substituents or with 1 or 2 substituents selected from C$_{1-6}$alkyl, Het-C$_{1-6}$alkyl, Ar$^1$—C$_{1-6}$alkyl, cyanoC$_{1-6}$alkyl, C$_{2-6}$alkenyl, cyanoC$_{2-6}$alkenyl, C$_{2-6}$alkynyl, cyanoC$_{2-6}$alkynyl, $R^{6b}$—O—C$_{1-6}$alkyl, amino-S(=O)$_2$—C$_{1-6}$alkyl, $R^{6b}$—O—C(=O)—C$_{1-6}$alkyl, amino-C(=O)—C$_{1-6}$alkyl, mono- and di-C$_{1-6}$alkylamino-C(=O)—C$_{1-6}$alkyl;

(g) Ar$^2$ is phenyl, or phenyl substituted with 1, 2, or 3 substituents or with 1 or 2 substituents selected from C$_{1-6}$alkyl, $R^{6b}$—O—C$_{1-6}$alkyl and amino-C(=O)—C$_{1-6}$alkyl; or selected from C$_{1-6}$alkyl, hydroxy-C$_{1-6}$alkyl and amino-C(=O)—C$_{1-6}$alkyl.

The limitations in the substitutions on Ar$^2$ as specified under (a)-(g) above preferably apply to any Ar$^2$ being part of a radical R$^{2a}$ or R$^{3a}$ being C$_{1-6}$alkyl substituted with a radical —NR$^{4a}$R$^{4b}$ wherein R$^{4a}$ and/or R$^{4b}$ is or are a radical Ar$^2$.

Other subgroups of the compounds of formula (I) are those compounds of formula (I), or any subgroup of compounds of formula (I) specified herein, wherein (h) Ar$^2$ is phenyl substituted with C$_{1-6}$alkyl, Het-C$_{1-6}$alkyl, Ar$^1$—C$_{1-6}$alkyl, cyanoC$_{1-6}$alkyl, C$_{2-6}$alkenyl, cyanoC$_{2-6}$alkenyl, C$_{2-6}$alkynyl, cyanoC$_{2-6}$alkynyl, $R^{6b}$—O—C$_{1-6}$alkyl, amino-S(=O)$_2$—C$_{1-6}$alkyl, $R^{6b}$—O—C(=O)—C$_{1-6}$alkyl, amino-C(=O)—C$_{1-6}$alkyl, mono- and di-C$_{1-6}$alkylamino-C(=O)—C$_{1-6}$alkyl; and optionally further substituted with one or with two of the substituents of Ar$^2$ mentioned above in restrictions (a) to (g); or (i) Ar$^2$ is phenyl substituted with $R^{6b}$—O—C$_{1-6}$alkyl, amino-C(=O)—C$_{1-6}$alkyl; or phenyl substituted with hydroxy-C$_{1-6}$alkyl, amino-C(=O)—C$_{1-6}$alkyl; and optionally further substituted with one or with two of the substituents on Ar$^2$ mentioned above in restrictions (a) to (g).

The limitations in the substitutions on Ar$^2$ as specified under (h)-(i) above preferably apply to any Ar$^2$ being part of a radical R$^{2a}$ or R$^{3a}$ being C$_{1-6}$alkyl substituted with a radical Ar$^2$.

Further subgroups are compounds of formula (I) or of any of the subgroups of compounds of formula (I) wherein:

(a) R$^{6a}$ in particular is hydrogen, C$_{1-6}$alkyl, Ar$^1$, Ar$^1$C$_{1-6}$alkyl, C$_{1-6}$alkylcarbonyl, Ar$^1$carbonyl, Ar$^1$C$_{1-6}$alkylcarbonyl, C$_{1-6}$alkyloxyC$_{1-6}$alkyl, aminoC$_{1-6}$alkyl, mono- or di(C$_{1-6}$alkyl)aminoC$_{1-6}$alkyl, hydroxyC$_{1-6}$alkyl, (carboxyl)-C$_{1-6}$alkyl, (C$_{1-6}$alkyloxycarbonyl)-C$_{1-6}$alkyl, aminocarbonylC$_{1-6}$alkyl, mono- and di(C$_{1-6}$alkyl)aminocarbonylC$_{1-6}$alkyl, aminosulfonyl-C$_{1-6}$alkyl, mono- and di(C$_{1-6}$alkyl)aminosulfonyl-C$_{1-6}$alkyl, Het, Het-C$_{1-6}$alkyl, Het-carbonyl, Het-C$_{1-6}$alkylcarbonyl;

(b) R$^{6a}$ more in particular is hydrogen, C$_{1-6}$alkyl, Ar$^1$, Ar$^1$C$_{1-6}$alkyl, C$_{1-6}$alkyloxy-C$_{1-6}$alkyl, aminoC$_{1-6}$alkyl, mono- or di(C$_{1-6}$alkyl)aminoC$_{1-6}$alkyl, hydroxyC$_{1-6}$alkyl, (carboxyl)-C$_{1-6}$alkyl, (C$_{1-6}$alkyloxycarbonyl)-C$_{1-6}$alkyl, aminocarbonylC$_{1-6}$alkyl, mono- and di(C$_{1-6}$alkyl)aminocarbonylC$_{1-6}$alkyl, aminosulfonyl-C$_{1-6}$alkyl, mono- and di(C$_{1-6}$alkyl)aminosulfonyl-C$_{1-6}$alkyl, Het, Het-C$_{1-6}$;

(c) R$^{6a}$ further in particular is hydrogen, C$_{1-6}$alkyl, Ar$^1$C$_{1-6}$alkyl, C$_{1-6}$alkyloxyC$_{1-6}$alkyl, aminoC$_{1-6}$alkyl, mono- or di(C$_{1-6}$alkyl)aminoC$_{1-6}$alkyl, hydroxyC$_{1-6}$alkyl, (carboxyl)-C$_{1-6}$alkyl, (C$_{1-6}$alkyloxycarbonyl)-C$_{1-6}$alkyl, aminocarbonylC$_{1-6}$alkyl, mono- and di(C$_{1-6}$alkyl)aminocarbonylC$_{1-6}$alkyl, aminosulfonyl-C$_{1-6}$alkyl, mono- and di(C$_{1-6}$alkyl)aminosulfonyl-C$_{1-6}$alkyl, Het-C$_{1-6}$alkyl;

(d) R$^{6a}$ further in particular is hydrogen, C$_{1-6}$alkyl, Ar$^1$C$_{1-6}$alkyl, aminoC$_{1-6}$alkyl, hydroxyC$_{1-6}$alkyl, (carboxyl)-C$_{1-6}$alkyl, aminocarbonylC$_{1-6}$alkyl, aminosulfonyl-C$_{1-6}$alkyl, morpholinyl-C$_{1-6}$alkyl; (e) R$^{6a}$ further in particular is hydrogen, hydroxyC$_{1-6}$alkyl, aminocarbonylC$_{1-6}$alkyl, aminosulfonyl-C$_{1-6}$alkyl; or wherein (e) R$^{6a}$ is hydrogen, C$_{1-6}$alkyl, Ar$^1$ or Ar$^1$C$_{1-6}$alkyl; or R$^{6a}$ is hydrogen or C$_{1-6}$alkyl; or R$^{6a}$ is hydrogen.

Further subgroups are compounds of formula (I) or of any of the subgroups of compounds of formula (I) wherein:

(f) R$^{6b}$ preferably is hydrogen or C$_{1-6}$alkyl; or more preferably is hydrogen;

(g) R$^{6c}$ preferably is C$_{1-6}$alkyl.

In the group of compounds of formula (I) or in any of the subgroups of compounds of formula (I):

(a) Ar$^1$ preferably is phenyl or phenyl substituted with up to 3 substituents, or with up to 2 substituents, or with one substituent, selected from halo, hydroxy, C$_{1-6}$alkyl, hydroxyC$_{1-6}$alkyl, trifluoromethyl, and C$_{1-6}$alkyloxy;

(b) Ar$^1$ more preferably is phenyl or phenyl substituted with up to 3 substituents, or with up to 2 substituents, or with one substituent, selected from halo, hydroxy, C$_{1-6}$alkyl and C$_{1-6}$alkyloxy;

(c) Ar$^1$ more preferably is phenyl or phenyl substituted with up to 3 substituents, or with up to 2 substituents, or with one substituent, selected from halo and C$_{1-6}$alkyl.

Other subgroups of the compounds of formula (I) are those compounds of formula (I), or any subgroup of compounds of formula (I) specified herein, wherein (a) Het is tetrahydrofuranyl, furanyl, thienyl, thiazolyl, oxazolyl, imidazolyl, isothiazolyl, pyrazolyl, isoxazolyl, piperidinyl, homopiperidinyl, piperazinyl, morpholinyl, pyridyl, pyrazinyl, pyrimidinyl, tetrahydroquinolinyl, quinolinyl, isoquinolinyl, benzodioxanyl, benzodioxolyl, indolinyl, indolyl, which may optionally be substituted with oxo, amino, Ar$^1$, C$_{1-4}$alkyl, aminoC$_{1-6}$alkyl, Ar$^1$C$_{1-4}$ alkyl, mono- or di($C_{1-6}$alkyl)amino$C_{1-6}$alkyl, mono- or di($C_{1-6}$alkyl)amino, (hydroxy$C_{1-6}$alkyl)amino, and optionally further with one or two $C_{1-4}$alkyl radicals; or (b) Het is tetrahydrofuranyl, furanyl, thienyl, thiazolyl, oxazolyl, imidazolyl, pyrazolyl, isoxazolyl, piperidinyl, homopiperidinyl, piperazinyl, morpholinyl, pyridyl, pyrazinyl, pyrimidinyl, tetrahydroquinolinyl, quinolinyl, isoquinolinyl, benzodioxanyl, benzodioxolyl, indolinyl, indolyl, which may optionally be substituted with oxo, amino, $Ar^1$, $C_{1-4}$alkyl, amino$C_{1-4}$alkyl, and optionally further with one or two $C_{1-4}$alkyl radicals; or (c) Het is furanyl, thienyl, pyrazolyl isoxazolyl, morpholinyl, pyrimidinyl, quinolinyl, indolinyl, which may optionally be substituted with one or two $C_{1-4}$alkyl radicals.

(d) Het is morpholinyl, which may optionally be substituted with one or two $C_{1-4}$alkyl radicals; or (d) Het is morpholinyl.

A particular embodiment of the present invention concerns compounds of formula (I) wherein Q, G, $R^1$ and $R^5$ are as specified above in the definition of formula (I) or as in any of the subgroups of compounds of formula (I) specified herein; and wherein (a) one of $R^{2a}$ and $R^{3a}$ is selected from —N($R^{4a}R^{4b}$), ($R^{4a}R^{4b}$)N—CO—, $C_{1-6}$alkyl substituted with one or two substituents selected from hydroxy, cyano, $Ar^2$, Het or —N($R^{4a}R^{4b}$) and $C_{2-6}$alkenyl substituted with cyano or $Ar^2$; and the other one of $R^{2a}$ and $R^{3a}$ is hydrogen; or (b) one of $R^{2a}$ and $R^{3a}$ is selected from —N($R^{4a}R^{4b}$); ($R^{4a}R^{4b}$)N—CO—; $C_{1-6}$alkyl optionally substituted with hydroxy, cyano, $Ar^2$, Het or —N($R^{4a}R^{4b}$); $C_{1-6}$alkyl substituted with hydroxy and $Ar^2$; and $C_{2-6}$alkenyl substituted with cyano or $Ar^2$; and the other one of $R^{2a}$ and $R^{3a}$ is hydrogen; or (c) one of $R^{2a}$ and $R^{3a}$ is selected from ($R^{4a}R^{4b}$)N—CO—; $C_{1-6}$alkyl optionally substituted with hydroxy, $Ar^2$, Het or —N($R^{4a}R^{4b}$); and $C_{2-6}$alkenyl substituted with $Ar^2$; and the other one of $R^{2a}$ and $R^{3a}$ is hydrogen; and in case $R^{2a}$ is different from hydrogen then $R^{2b}$ is hydrogen, $C_{1-6}$alkyl or halogen and $R^{3b}$ is hydrogen;

in case $R^{3a}$ is different from hydrogen then $R^{3b}$ is hydrogen, $C_{1-6}$alkyl or halogen and $R^{2b}$ is hydrogen;

$Ar^2$, Het $R^{4a}$ and $R^{4b}$ are as in the definitions of the compounds of formula (I) or as in any subgroup specified herein.

Another particular embodiment of the present invention concerns compounds of formula (I) wherein Q, G, $R^1$ and $R^5$ are as specified above in the definition of formula (I) or as in any of the subgroups of compounds of formula (I) specified herein; and (d) one of $R^{2a}$ and $R^{3a}$ is selected from ($R^{4a}R^{4b}$)N—CO—; $C_{1-6}$alkyl optionally substituted with hydroxy, $Ar^2$, Het or —N($R^{4a}R^{4b}$); and $C_{2-6}$alkenyl substituted with $Ar^1$; and the other one of $R^{2a}$ and $R^{3a}$ is hydrogen; or (e) one of $R^{2a}$ and $R^{3a}$ is selected from ($R^{4a}$)HN—CO—; $C_{1-6}$alkyl optionally substituted with hydroxy, $Ar^2$, Het, —NH($R^{4a}$) or —N($R^{4a}$)$Ar^2$; and $C_{2-6}$alkenyl substituted with $Ar^1$; and the other one of $R^{2a}$ and $R^{3a}$ is hydrogen; or (f) one of $R^{2a}$ and $R^{3a}$ is $C_{1-6}$alkyl optionally substituted with hydroxy, $Ar^2$, Het, —NH($R^{4a}$) or —N($R^{4a}$)$Ar^2$; and the other one of $R^{2a}$ and $R^{3a}$ is hydrogen; or (g) one of $R^{2a}$ and $R^{3a}$ is $C_{1-6}$alkyl optionally substituted with hydroxy, $Ar^2$, —NH($R^{4a}$) or —N($R^{4a}$)$Ar^2$; and the other one of $R^{2a}$ and $R^{3a}$ is hydrogen;

(h) one of $R^{2a}$ and $R^{3a}$ is $C_{1-6}$alkyl optionally substituted with —NH($R^{4a}$) or —N($R^{4a}$)$Ar^2$; and the other one of $R^{2a}$ and $R^{3a}$ is hydrogen;

(i) one of $R^{2a}$ and $R^{3a}$ is $C_{1-6}$alkyl optionally substituted with —NH($R^{4a}$); and the other one of $R^{2a}$ and $R^{3a}$ is hydrogen;

(j) one of $R^{2a}$ and $R^{3a}$ is $C_{1-6}$alkyl optionally substituted with —N($R^{4a}$)$Ar^2$; and the other one of $R^{2a}$ and $R^{3a}$ is hydrogen;

in case $R^{2a}$ is different from hydrogen then $R^{2b}$ is hydrogen or $C_{1-6}$alkyl and $R^{3b}$ is hydrogen;

in case $R^{3a}$ is different from hydrogen then $R^{3b}$ is hydrogen or $C_{1-6}$alkyl and $R^{2b}$ is hydrogen;

$Ar^2$, Het, $R^{4a}$ and $R^{4b}$ are as in the definitions of the compounds of formula (I) or as in any subgroup specified herein.

Another particular embodiment of the present invention concerns compounds of formula (I) wherein Q, G, $R^1$ and $R^5$ are as specified above in the definition of formula (I) or as in any of the subgroups of compounds of formula (I) specified herein; wherein $R^{2a}$ and $R^{3a}$ are as defined in (a)-(j) above and $R^{2b}$ and $R^{3b}$ are both hydrogen.

Another embodiment of the present invention concerns compounds of formula (I) wherein Q, G, $R^1$ and $R^5$ are as specified above in the definition of formula (I) or as in any of the subgroups of compounds of formula (I) specified herein; wherein (k) one of $R^{2a}$ and $R^{3a}$ is $C_{1-6}$alkyl; and the other one of $R^{2a}$ and $R^{3a}$ is hydrogen;

in case $R^{2a}$ is different from hydrogen then $R^{2b}$ is $C_{1-6}$alkyl and $R^{3b}$ is hydrogen;

in case $R^{3a}$ is different from hydrogen then $R^{3b}$ is $C_{1-6}$alkyl and $R^{2b}$ is hydrogen.

Still another embodiment of the present invention concerns compounds of formula (I) wherein Q, G, $R^1$ and $R^5$ are as specified above in the definition of formula (I) or as in any of the subgroups of compounds of formula (I) specified herein; wherein one of $R^{2a}$ and $R^{3a}$ is selected from $C_{1-6}$alkyl substituted with —N($R^{4a}R^{4b}$), wherein $R^{4b}$ is hydrogen;

and the other one of $R^{2a}$ and $R^{3b}$ is hydrogen; and in case $R^{2a}$ is different from hydrogen then $R^{2b}$ is hydrogen and $R^{3b}$ is hydrogen;

in case $R^{3a}$ is different from hydrogen then $R^{3b}$ is hydrogen and $R^{2b}$ is hydrogen.

Still another embodiment of the present invention concerns compounds of formula (I) wherein Q, G, $R^1$ and $R^5$ are as specified above or as in any of the subgroups of compounds specified herein; and one of $R^{2a}$ and $R^{3a}$ is selected from $C_{1-6}$alkyl substituted with —N($R^{4a}R^{4b}$); and the other one of $R^{2a}$ and $R^{3a}$ is hydrogen; and in case $R^{2a}$ is different from hydrogen then $R^{2b}$ is hydrogen and $R^{3b}$ is hydrogen;

in case $R^{3a}$ is different from hydrogen then $R^{3b}$ is hydrogen and $R^{2b}$ is hydrogen; and further wherein $R^{4a}$ is $Ar^2$ and $R^{4b}$ is $C_{1-6}$alkyl, $Ar^2C_{1-6}$alkyl, $C_{1-6}$alkyloxy$C_{1-6}$alkyl, hydroxy$C_{1-6}$alkyloxy$C_{1-6}$alkyl, $Ar^1C_{1-6}$alkyloxy$C_{1-6}$alkyl, ($C_{1-6}$alkyloxy)(hydroxy)$C_{1-6}$alkyl, ($Ar^1C_{1-6}$alkyloxy)(hydroxy)$C_{1-6}$alkyl, amino$C_{1-6}$alkyl, mono- and di($C_{1-6}$alkyl)amino$C_{1-6}$alkyl, hydroxy-$C_{1-6}$alkyl, aminocarbonyl$C_{1-6}$alkyl, mono- and di($C_{1-6}$alkyl)aminocarbonyl$C_{1-6}$alkyl, $C_{1-4}$alkyloxycarbonyl$C_{1-6}$alkyl, hydroxycarbonyl$C_{1-6}$alkyl, Het or Het-$C_{1-6}$alkyl.

Preferred compounds are those compounds listed in tables 1 through 6, more in particular the compound numbers 1 to 75, 81 to 116, 129 to 165, 167 to 183, 191 to 192, 194 to 197, 205 to 214 and 238 to 239.

Most preferred is compound 90 in Table 1, the name of which is 2-(2-amino-6-{[2-(3-hydroxy-propyl)-5-methylphenylamino]-methyl}-benzimidazol-1-ylmethyl)-6-methylpyridin-3-ol, as well as the prodrugs, N-oxides, addition salts, quaternary amines and metal complexes thereof, in particular said compound and the acid-addition salts thereof.

The compounds of formula (I) or any of the subgroups thereof can be prepared as in the following reaction schemes.

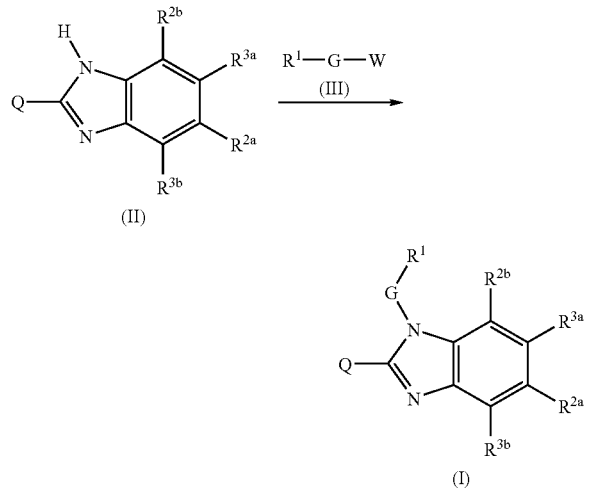

In this scheme G, $R^1$, $R^{2a}$, $R^{2b}$, $R^{3a}$, $R^{3b}$ have the meanings defined above for the compounds of formula (I) or of any of the subgroups thereof. W is an appropriate leaving group, preferably it is chloro or bromo. The reaction of this scheme can be typically conducted in a suitable solvent such as an ether, e.g. THF, a halogenated hydrocarbon, e.g. dichoromethane, $CHCl_3$, toluene, a polar aprotic solvent such as DMF, DMSO, DMA and the like. A base may be added to pick up the acid that is liberated during the reaction. If desired, certain catalysts such as iodide salts (e.g. KI) may be added.

Where in the conversion of (II) into (I) the radical Q is amino, said radical Q may be protected with an appropriate protecting group such as an alkyloxycarbonyl group, e.g. methoxycarbonyl, ethoxycarbonyl, t.butyloxycarbonyl, which subsequently is removed, for example by treatment with a base. Where radical Q is methoxycarbonylamino, said radical Q may be transformed into a methylamino group by treatment of the starting methoxycarbonylamino benzimidazole with a complex metal hydride such as $LiAlH_4$.

The compounds of formula (I) wherein Q is amino, said compounds being represented by formula (I-d) can be prepared as outlined in the following reaction schemes.

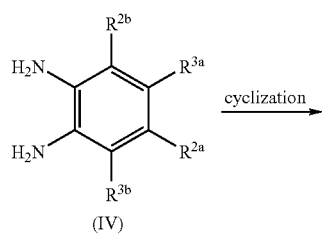

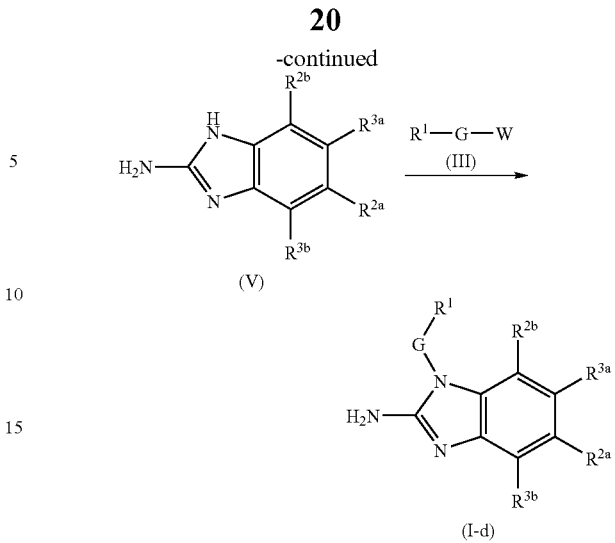

In a first step, a diaminobenzene (IV) is cyclized with a suitable reagent, for example with cyanogen bromide, preferably in a suitable solvent, e.g. an alcohol such ethanol, to yield an aminobenzimidazole (V). The latter intermediate (V) is reacted with reagent (III) in an N-alkylation reaction to obtain an intermediate (II). One of the amino groups in starting material (IV) can be substituted with a radical -G-$R^1$ and this derivative of (IV) can be cyclized with cyanogen bromide as described above to directly obtain (I-d). Alternatively, intermediate (IV) can be reacted with urea in a condensation reaction to yield a benzimidazol-2-one, in a suitable solvent such as xylene. The resulting product is converted into a corresponding 2-substituted benzimidazole derivative, wherein the group in 2-position is a leaving group, preferably halo, e.g. chloro or bromo, by reaction with a halogenating agent such as $POCl_3$. The obtained product can further be reacted with ammonia to yield (V).

The above-mentioned N-alkylations are conducted in a suitable solvent and, if desired, in the presence of a base.

Compounds of formula (I) may be converted into each other following art-known functional group transformation reactions, comprising those described hereinafter.

Compounds of formula (I) wherein $R^{2a}$ or $R^{3a}$ is $C_{1-6}$alkoxycarbonyl or $C_{1-6}$alkyl substituted with $C_{1-6}$alkoxycarbonyl can be reduced, e.g. with $LiAlH_4$, to the corresponding compounds wherein $R^{2a}$ or $R^{3a}$ is hydroxy $C_{1-6}$alkyl. The latter group can be oxidized to an aldehyde group, e.g. with $MnO_2$, which can further be derivatized with amines, e.g. with a reductive amination process, to the corresponding $C_{1-6}$alkylamines or derivatized amines. Alternatively the compounds of formula (I) wherein $R^{2a}$ or $R^{3a}$ is hydroxy$C_{1-6}$alkyl can be converted to the corresponding halo$C_{1-6}$alkyl compounds, e.g. by treatment with a suitable halogenating agent such as $SOCl_2$, which compounds subsequently are reacted with an amine or amine derivative.

Compounds of formula (I) wherein $R^{2a}$ or $R^{3a}$ is an aldehyde can be converted to the corresponding compounds wherein $R^{2a}$ or $R^{3a}$ is $C_{2-6}$alkenyl or substituted $C_{2-6}$alkenyl by a Wittig reaction or a Wittig-Horner reaction. In the former instance a Wittig type reagent is used, such as a triphenylphosphoniumylide in a suitable reaction-inert solvent such as an ether, starting from triphenylphosphine and a halo derivative. The Wittig-Horner reaction is performed using a phosphonate, such as e.g. a reagent of formula di($C_{1-6}$alkyloxy)-P(=O)—$CH_2$—$CH_2$—CN in the presence of a base, preferably a strong base, in an aprotic organic solvent. Compounds wherein $R^{2a}$ or $R^{3a}$ is $C_{2-6}$alkenyl or substituted $C_{2-6}$alkenyl can be reduced to the corresponding saturated alkyls, e.g. with hydrogen in the presence of a suitable catalyst such as Raney Ni.

Compounds of formula (I) wherein $R^{2a}$ or $R^{3a}$ is an aldehyde can also be derivatized with a Grignard type of reaction to introduce aryl or alkyl groups.

Nitro groups can be reduced to amino groups, which subsequently may be alkylated to mono- or dialkylamino groups, or acylated to arylcarbonylamino or alkylcarbonylamino and the like groups. Cyano groups may be reduced to aminomethylene groups, which similarly may be derivatized.

A number of the intermediates used to prepare the compounds of formula (I) are known compounds or are analogs of known compounds, which can be prepared following modifications of art-known methodologies readily accessible to the skilled person. A number of preparations of intermediates are given hereafter in somewhat more detail.

The intermediates of formula (VII) can be obtained from the corresponding alcohols by a suitable alcohol to leaving group conversion, e.g. by reaction of the alcohol with $SOCl_2$. The intermediates of formula (VII) wherein G is a direct bond and $R^1$ is a radical (c-4) or a similar radical, can be prepared by a halogenation reaction of an intermediate $R^1$—H, e.g. with N-bromo succinimide.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I) which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

In a further aspect, the present invention concerns a pharmaceutical composition comprising a therapeutically effective amount of a compound of formula (I) as specified herein, or a compound of any of the subgroups of compounds of formula (I) as specified herein, and a pharmaceutically acceptable carrier. A therapeutically effective amount in this context is an amount sufficient to prophylaxictically act against, to stabilize or to reduce viral infection, and in particular RSV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the subgroups of compounds of formula (I) as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailabilty, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. (Antiviral Research (1998), 38, 31-42).

Due to their antiviral properties, particularly their anti-RSV properties, the compounds of formula (I) or any subgroup thereof their prodrugs, N-oxides, addition salts, quaternary amines, metal complexes and stereochemically isomeric forms, are useful in the treatment of individuals experiencing a viral infection, particularly a RSV infection, and for the prophylaxis of these infections. In general, the compounds of the present invention may be useful in the treatment of warm-blooded animals infected with viruses, in particular the respiratory syncytial virus.

The compounds of the present invention or any subgroup thereof may therefore be used as medicines. Said use as a medicine or method of treatment comprises the systemic administration to viral infected subjects or to subjects susceptible to viral infections of an amount effective to combat the conditions associated with the viral infection, in particular the RSV infection.

The present invention also relates to the use of the present compounds or any subgroup thereof in the manufacture of a medicament for the treatment or the prevention of viral infections, particularly RSV infection.

The present invention furthermore relates to a method of treating a warm-blooded animal infected by a virus, or being at risk of infection by a virus, in particular by RSV, said method comprising the administration of an anti-virally effective amount of a compound of formula (I), as specified herein, or of a compound of any of the subgroups of compounds of formula (I), as specified herein.

In general it is contemplated that an antivirally effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

EXAMPLES

The following examples are intended to illustrate the present invention and not to limit it thereto. The terms 'compound 1, compound 4, etc. used in these examples refer to the same compounds in the tables.

The compounds were analysed by LC/MS using one of the following methods:

LCT: electrospray ionisation in positive mode, scanning mode from 100 to 900 amu; Xterra MS C18 (Waters, Milford, Mass.) 5 µm, 3.9×150 mm); flow rate 1 ml/min. Two mobile phases (mobile phase A: 85% 6.5 mM ammonium acetate+15% acetonitrile; mobile phase B: 20% 6.5 mM ammonium acetate+80% acetonitrile) were employed to run a gradient from 100% A for 3 min to 100% B in 5 min., 100% B for 6 min to 100% A in 3 min, and equilibrate again with 100% A for 3 min)

ZQ: electrospray ionisation in both positive and negative (pulsed) mode scanning from 100 to 1000 amu; Xterra RP C18 (Waters, Milford, Mass.) 5 µm, 3.9×150 mm); flow rate 1 ml/min. Two mobile phases (mobile phase A: 85% 6.5 mM ammonium acetate+15% acetonitrile; mobile phase B: 20% 6.5 mM ammonium acetate+80% acetonitrile) were employed to run a gradient condition from 100% A for 3 min

Example 1

Preparation of dimethylbenzimidazole-2-amines

Scheme A

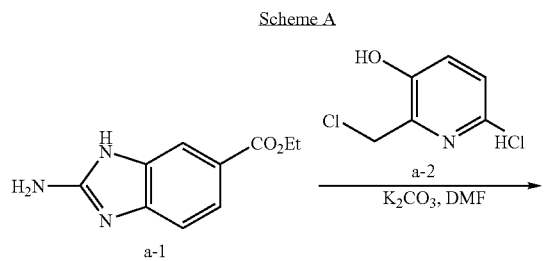
a-1

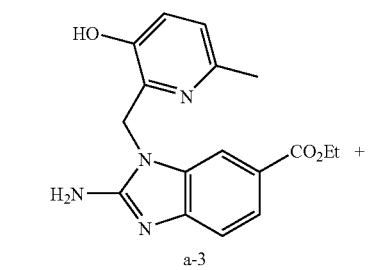
a-3

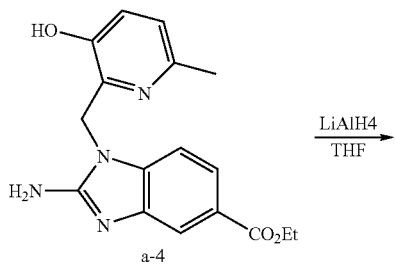
a-4

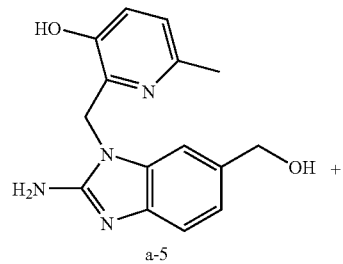
a-5

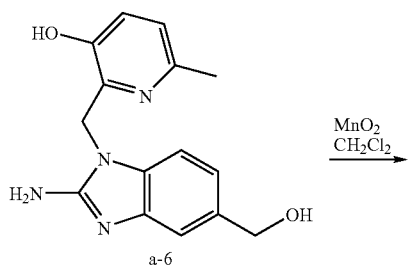
a-6

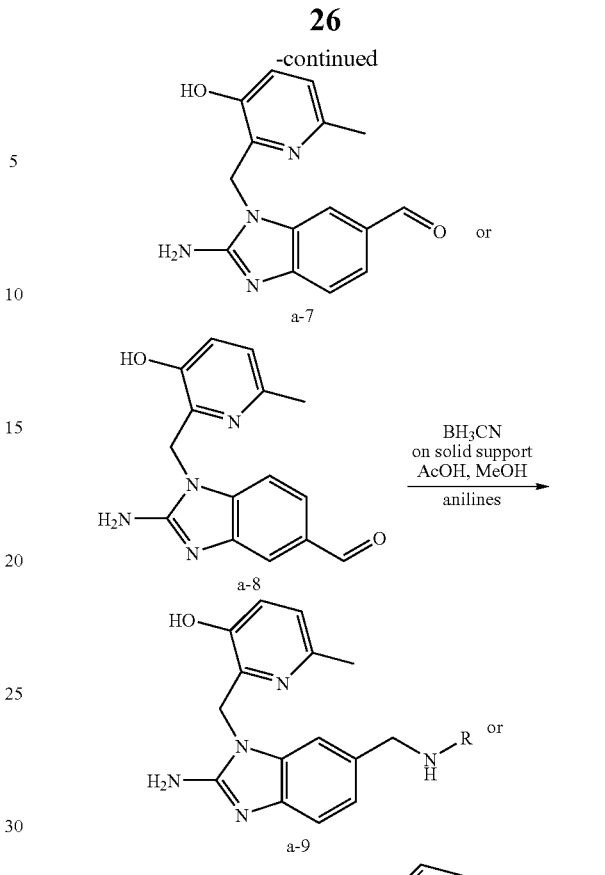

Preparation of Intermediates a-3 and a-4:

A mixture of a-1 (0.0268 mol), a-2 (0.0321 mol) and potassium carbonate (0.0938 mol) in dimethylformamide (100 ml) were stirred at 70° C. for 12 hours. The solvent was evaporated. The residue was taken up in 2-propanone. The precipitate was filtered. The solvent of the mother layer was evaporated. The residue (13.6 g) was purified by column chromatography over silica gel (eluent: $CH_2Cl_2/CH_3OH/NH_4OH$ 92/8/0.5; 20-45 µm). The pure fractions were collected and the solvent was evaporated, yielding 6.2 g of a mixture of a-3 and a-4 (50/50) (overall yield 71%).

Preparation of Intermediates a-5 and a-6:

Lithium aluminum hydride (0.0367 mol) was added portion wise at 0° C. to a mixture of a-3 and a-4 (0.0184 mol) in tetrahydrofuran (THF) (100 ml) under nitrogen flow. The mixture was stirred at 5° C. for 30 minutes, then at room temperature for 2 hours. Ethylacetate (5 ml) then $H_2O$ (5 ml) were added drop wise at 0° C. The mixture was filtered over celite. Celite was washed with THF and then water. The filtrate was extracted with a solution of $CH_2Cl_2$ with 10% of methanol. The organic layer was dried over magnesium sulfate, filtered and concentrated. The residue (5 g) was purified by column chromatography over silica gel (eluent $CH_2Cl_2/CH_3OH/NH_4OH$ 92/8/0.5; 15-40 µm). Two fractions were collected and the solvent evaporated, yielding 1.45 g of a-5 (28%, melting point: >250° C.) and 1.4 g of a-6 (27%, melting point 222° C.).

Preparation of Intermediate a-7:

MnO$_2$ (10 g) was added to a mixture of a-5 (0.0035 mol) in CH$_2$Cl$_2$/THF (50 ml, 50/50) and methanol (5 ml). The reaction was stirred at room temperature for 3 hours, and then filtered over celite. Celite was washed with CH$_2$Cl$_2$/methanol (90/10). The filtrate was evaporated, yielding 0.6 g of a-7 (60%). This product was used directly in the next reaction step.

Preparation of Intermediate a-8:

This intermediate was prepared analogous to the procedure for preparing intermediate a-7.

Preparation of Compounds of Formula a-9 and a-10:

Variant 1: Meta-methylaniline (0.0017 mol) was added at room temperature to a mixture of a-7 (0.0017 mol) and CH$_2$Cl$_2$ (15 ml). The mixture was stirred at room temperature for 30 minutes. Acetic acid (0.5 ml) and NaBH$_3$CN (0.0017 mol) were added at room temperature. The reaction mixture was stirred at room temperature for 5 hours, poured into water saturated with K$_2$CO$_3$ and extracted with CH$_2$Cl$_2$. The organic layer was washed with H$_2$O, dried over magnesium sulfate, filtered, and the solvent was evaporated. The residue (0.45 g) was purified by column chromatography over silica gel (eluent: CH$_2$Cl$_2$/CH$_3$OH/NH$_4$OH 90/10/0.5; 15-35 μm). The pure fractions were collected and the solvent was evaporated. The residue (0.26 g, 40%) was crystallized from 2-propanone/diethyl ether. The precipitate was filtered off and dried, yielding 0.195 g (30%, compound 1, melting point 234° C.) of 2-[2-Amino-6-(m tolylamino-methyl)-benzoimidazol-1-ylmethyl]-6-methyl-pyridin-3-ol.

Variant 2: A mixture of a-7 (0.001 mol), meta-(OCF$_3$)-aniline (0.0015 mol), supported cyano-borohydride (0.0021 mol) and acetic acid (6 drops) in methanol was stirred at room temperature for 48 hours, and then filtered. The filtrate was evaporated. The residue was taken up in CH$_2$Cl$_2$/methanol. The organic layer was washed with a solution of K$_2$CO$_3$ 10%, dried over magnesium sulfate, filtered and the solvent was evaporated. The residue (0.42 g) was purified by column chromatography over silica gel (eluent: CH$_2$Cl$_2$/CH$_3$OH/NH$_4$OH 93/7/0.5; 15-35 μm). The pure fractions were collected and the solvent was evaporated. The residue (0.15 g, 32%) was crystallized from CH$_3$CN/methanol. The precipitate was filtered off and dried, yielding 0.085 g (18%, compound 4, melting point 156° C.) of 2-{2-Amino-6-[(3-trifluoromethoxyphenylamino)-methyl]-benzoimidazol-1-ylmethyl}-6-methyl-pyridin-3-ol.

Variant 3: Ortho-methylaniline (0.000265 mol) was added to solution of a-7 (0.000177 mol) in methanol (7 ml). Acetic acid (3 drops) and cyano borohydride on solid support (0.000265 mol) were then added. The reaction was carried out at room temperature for 48 h. The supported reagent was filtered off. Triethylamine (0.2 ml) was added to the filtrate. The solvent was evaporated. The residue was purified by column chromatography over silica gel (eluent CH$_2$Cl$_2$/CH$_3$OH/NH$_4$OH 90/10/0.5; 10 μm).

The pure fractions were collected and the solvent was evaporated. The residue (0.050 g, 65%) was crystallized from diisopropyl-ether. The precipitate was filtered off and dried, yielding 0.027 g (35%, compound 8, melting point 120° C.) of 2-[2-Amino-6-(o-tolylamino-methyl)-benzoimidazol-1-ylmethyl]-6-methyl-pyridin-3-ol acetic acid salt.

Example 2

Preparation of 6-aminomethyl substituted benzimidazole-2-amines

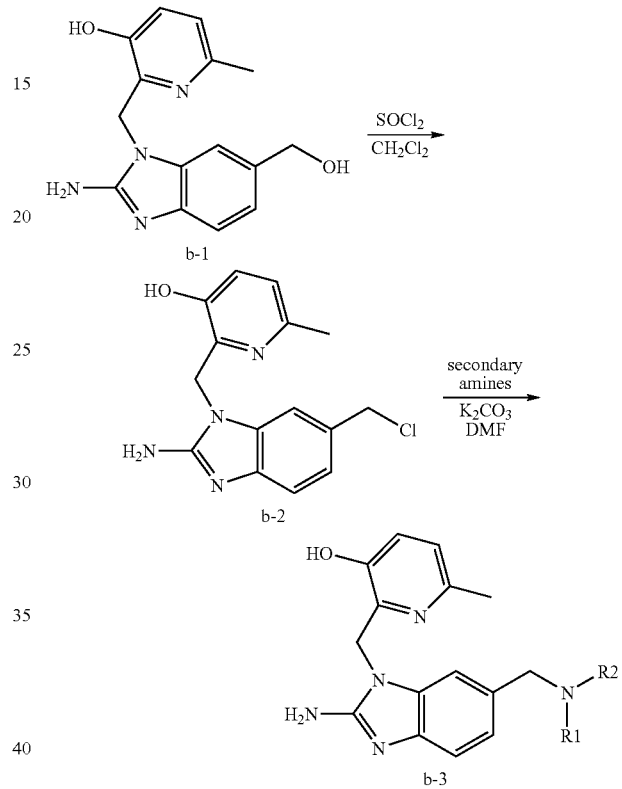

Preparation of Intermediate b-2:

SOCl$_2$ (0.0021 mol) was added drop wise at 5° C. to a solution of b-1 (0.0014 mol) in CH$_2$Cl$_2$ (10 ml). The mixture was stirred at room temperature for 4 hours. The precipitate was filtered, washed with CH$_2$Cl$_2$, then with diisopropyl ether and dried, yielding 0.49 g of b-2 (100%).

Preparation of Compounds of Formula b-3

Variant 1: A mixture of b-2 (0.0008 mol), (N-ethanol)-meta-methylaniline (0.0013 mol) and potassium carbonate (0.003 mol) in dimethylformamide (5 ml) was stirred at 80° C. for 12 hours, poured into water and extracted with CH$_2$Cl$_2$. The organic layer was washed with water, dried over magnesium sulfate, filtered and the solvent was evaporated. The residue (0.4 g) was purified by column chromatography over silica gel (eluent: CH$_2$Cl$_2$/CH$_3$OH/NH$_4$OH 93/7/0.5; 15-35 μm). The pure fractions were collected and the solvent was evaporated. The residue (0.13 g, 35%) was crystallized from methanol. The precipitate was filtered off and dried, yielding 0.06 g (16%, compound 129, melting point 210° C.) of 2-(2-amino-6-{[(2-hydroxy-ethyl)-m-tolyl-amino]-methyl}-benzoimidazol-1-ylmethyl)-6-methyl-pyridin-3-ol.

Variant 2:
a) 3-bromo-butyric acid ethyl ester (0.029 mol) and triethylamine (0.0436 mol) were added to a solution of 3-bromoaniline (0.029 mol) in toluene (50 ml). The reaction was stirred under reflux for 12 hours and then cooled down to room temperature. The precipitate was filtered off. The solvent was evaporated under reduced pressure. The residue was purified by column chromatography over silica gel (eluent: Cyclohexane:AcOEt 80/20; 20-45 μm). The pure fractions were collected and the solvent was evaporated, yielding 5 g of 4-(3-bromo-phenylamino)-butyric acid ethyl ester (60%, melting point: 65° C.).

b) 4-(3-Bromo-phenylamino)-butyric acid ethyl ester (0.00524 mol) in tetrahydrofuran (15 ml) was added drop wise to slurry of LiAlH$_4$ (0.00786 mol) in tetrahydrofuran (15 ml) at 5° C. under N$_2$ flow. The reaction was stirred at 5° C. for 1 hour. Ethylacetate and water were added carefully. The reaction was extracted with a mixture CH$_2$Cl$_2$/methanol (90/10). The organic layer was separated, dried (over MgSO$_4$) and filtered. The solvent was evaporated under reduced pressure. The residue was purified by column chromatography over silica gel (eluent CH$_2$Cl$_2$/CH$_3$OH/NH$_4$OH 96/4/0.3; 15-40 μm). The pure fractions were collected and the solvent was evaporated, yielding 0.76 g of 4-(3-bromophenylamino)-butan-1-ol (60%).

c) 2-(2-Amino-6-{[(3-bromo-phenyl)-(4-hydroxy-butyl)-amino]-methyl}-benzoimidazol-1-ylmethyl)-6-methyl-pyridin-3-ol (compound 139, melting point 120° C. gum) was synthesized starting from 4-(3-bromo-phenylamino)-butan-1-ol in a way analogous to the procedure described in variant 1 for the synthesis of compounds b-3.

Variant 3:
a) A mixture of 3-(3-bromo-aniline)-propionic acid ethyl ester (0.0037 mol) and a saturated solution of NH$_3$ in methanol (15 ml) were heated at 80° C. in a PARR apparatus for 12 hours. The reaction was cooled down to room temperature and the solvent was evaporated under reduced pressure. The residue was purified by column chromatography over silica gel (eluent: Cyclohexane:ethylacetate 80/20; 20-45 μm). The pure fractions were collected and the solvent was evaporated, yielding 0.75 g of 3-(3-bromo-phenylamino)-propionamide (83%).

b) 3-[[2-Amino-3-(3-hydroxy-6-methyl-pyridin-2-ylmethyl)-3H-benzoimidazol-5-ylmethyl]-(3-bromo-phenyl)-amino]-propionamide (compound 137, melting point: 245° C.) was synthesized starting from 3-(3-bromo-phenylamino)-propionamide in a way analogous to the procedure described in variant 1 for the synthesis of compounds b-3.

Variant 4:
a) K$_2$CO$_3$ (0.0109 mol) and 4-(2-chloro-ethyl)-morpholine (1 HCl) (0.0036 mol) were added to a solution of 2-ethanol-aniline (0.0036 mol) in CH$_3$CN (15 ml). The reaction was stirred at 80° C. for 24 hours and then cooled down to room temperature. The precipitate was filtered off and rinsed with CH$_3$CN. The solution was concentrated under reduced pressure. The residue was purified by column chromatography over silica gel (eluent CH$_2$Cl$_2$/CH$_3$OH/NH$_4$OH 98/2/0.1; 35-70 μm). The pure fractions were collected and the solvent was evaporated, yelding 0.7 g of 2-[2-(2-morpholin-4-yl-ethylamino)-phenyl]-ethanol (77%).

b) 2-(2-Amino-6-{[[2-(2-hydroxy-ethyl)-phenyl]-(2-morpholin-4-yl-ethyl)-amino]-methyl}-benzoimidazol-1-ylmethyl)-6-methyl-pyridin-3-ol (compound 160, melting point: 184° C.) was synthesized starting from 2-[2-(2-morpholin-4-yl-ethylamino)-phenyl]-ethanol in a way analogous to the procedure described in variant 1 for the synthesis of compounds b-3.

Variant 5:
Lithium hydroxide hydrate (0.00093 mol) was added to a solution of 3-{[2-amino-3-(3-hydroxy-6-methyl-pyridin-2-ylmethyl)-3H-benzoimidazol-5-ylmethyl]-m-tolylamino}-propionic acid ethyl ester (0.000464 mol) in a mixture of water (10 ml) and tetrahydrofuran (10 ml). The reaction was stirred at room temperature for 12 hours. The tetrahydrofuran was removed under reduced pressure and the solution was acidified to pH 4 with a 1N solution of HCl in water. The precipitate was filtered off, rinsed with water, then with diethyl ether and dried, yielding 0.157 g of 3-{[2-amino-3-(3-hydroxy-6-methyl-pyridin-2-ylmethyl)-3H-benzoimidazol-5-ylmethyl]-m-tolyl-amino}-propionic acid (76%, compound 161, melting point 165° C.).

Variant 6:
a) A mixture of b-2 (0.0016 mol), N-(ethylamino-Boc)-meta-methylaniline (0.0016 mol) and K$_2$CO$_3$ (0.0048 mol) in dimethylformamide (10 ml) was stirred at 80° C. for 12 hours. The reaction was poured into water and extracted with CH$_2$Cl$_2$/methanol. The organic layer was washed with water, dried over magnesium sulfate, filtered and the solvent was evaporated. The residue (4 g) was purified by column chromatography over silica gel (eluent CH$_2$Cl$_2$/CH$_3$OH/NH$_4$OH 95/5/0.5; 10 μm). The pure fractions were collected and the solvent was evaporated, yielding 0.11 g (13%) of 2-{2-Amino-6-[(propyl-m-tolyl-amino)-methyl]-benzoimidazol-1-ylmethyl}-6-methyl-pyridin-3-ol (b-4).

b) A solution of HCl 5-6N in 2-propanol (0.5 ml) was added at room temperature to a mixture of b-4 (0.0002 mol) in 2-propanol (15 ml). The mixture was stirred at 60° C. for 2 hours, and then cooled to room temperature. The precipitate was filtered off, washed with diethyl ether and dried, yielding 0.075 g (65%, compound 131, melting point: 200° C.) of 2-(2-amino-6-{[(2-amino-ethyl)-m-tolyl-amino]-methyl}-benzoimidazol-1-ylmethyl)-6-methyl-pyridin-3-ol HCl salt.

Example 3

Synthesis of 5- and 6-formyl substituted benzimidazole-2-amines

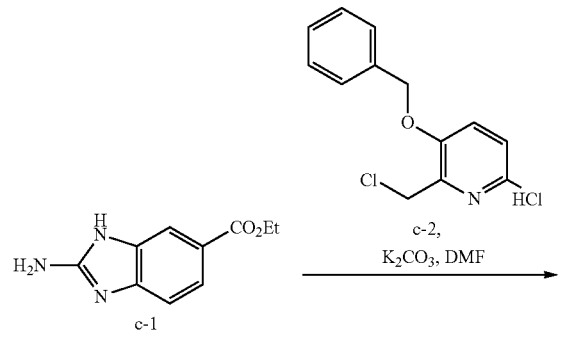

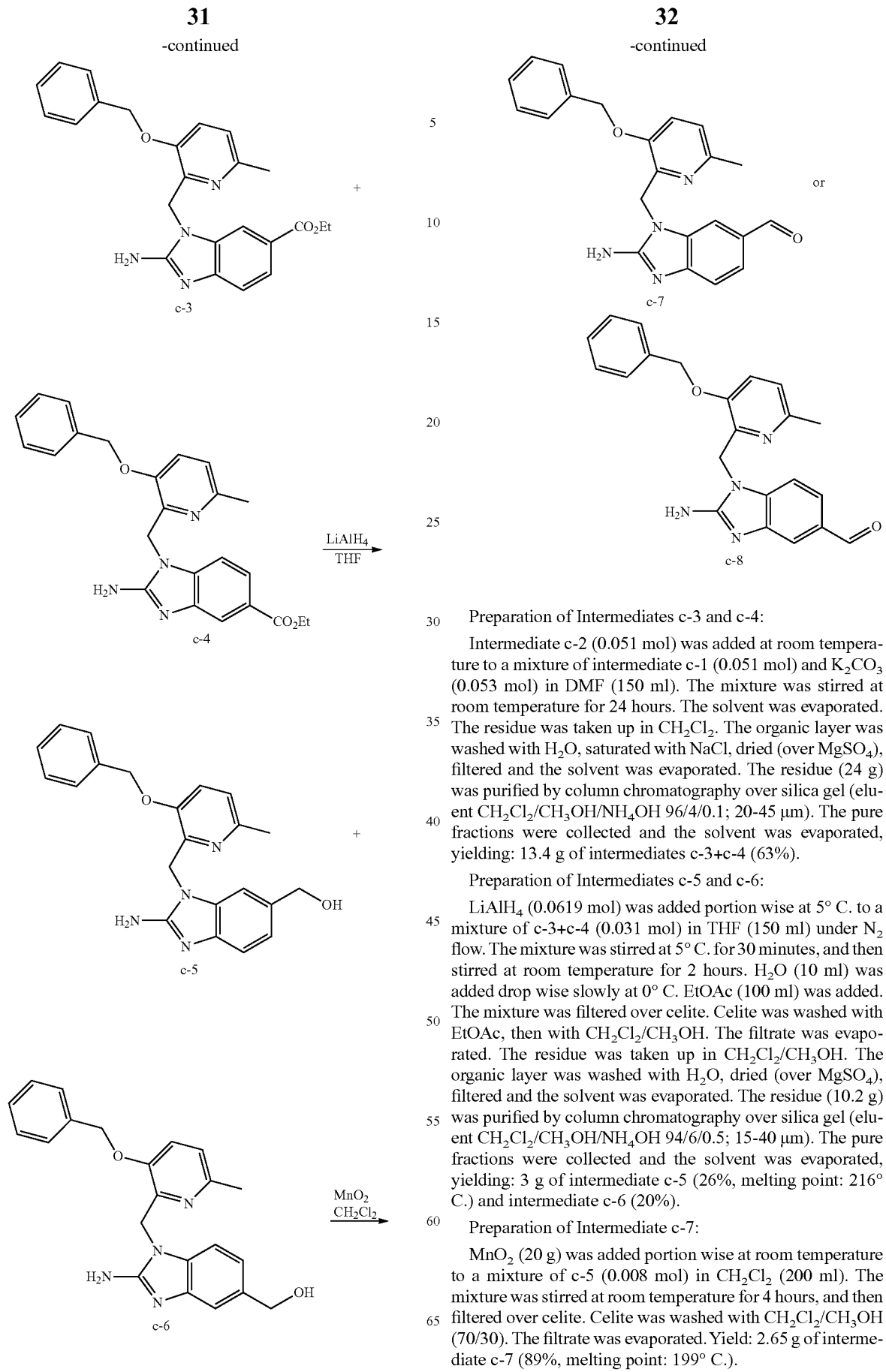

Preparation of Intermediates c-3 and c-4:

Intermediate c-2 (0.051 mol) was added at room temperature to a mixture of intermediate c-1 (0.051 mol) and $K_2CO_3$ (0.053 mol) in DMF (150 ml). The mixture was stirred at room temperature for 24 hours. The solvent was evaporated. The residue was taken up in $CH_2Cl_2$. The organic layer was washed with $H_2O$, saturated with NaCl, dried (over $MgSO_4$), filtered and the solvent was evaporated. The residue (24 g) was purified by column chromatography over silica gel (eluent $CH_2Cl_2/CH_3OH/NH_4OH$ 96/4/0.1; 20-45 μm). The pure fractions were collected and the solvent was evaporated, yielding: 13.4 g of intermediates c-3+c-4 (63%).

Preparation of Intermediates c-5 and c-6:

$LiAlH_4$ (0.0619 mol) was added portion wise at 5° C. to a mixture of c-3+c-4 (0.031 mol) in THF (150 ml) under $N_2$ flow. The mixture was stirred at 5° C. for 30 minutes, and then stirred at room temperature for 2 hours. $H_2O$ (10 ml) was added drop wise slowly at 0° C. EtOAc (100 ml) was added. The mixture was filtered over celite. Celite was washed with EtOAc, then with $CH_2Cl_2/CH_3OH$. The filtrate was evaporated. The residue was taken up in $CH_2Cl_2/CH_3OH$. The organic layer was washed with $H_2O$, dried (over $MgSO_4$), filtered and the solvent was evaporated. The residue (10.2 g) was purified by column chromatography over silica gel (eluent $CH_2Cl_2/CH_3OH/NH_4OH$ 94/6/0.5; 15-40 μm). The pure fractions were collected and the solvent was evaporated, yielding: 3 g of intermediate c-5 (26%, melting point: 216° C.) and intermediate c-6 (20%).

Preparation of Intermediate c-7:

$MnO_2$ (20 g) was added portion wise at room temperature to a mixture of c-5 (0.008 mol) in $CH_2Cl_2$ (200 ml). The mixture was stirred at room temperature for 4 hours, and then filtered over celite. Celite was washed with $CH_2Cl_2/CH_3OH$ (70/30). The filtrate was evaporated. Yield: 2.65 g of intermediate c-7 (89%, melting point: 199° C.).

Preparation of Intermediate c-8:

This intermediate was synthesized according to the procedure described for intermediate c-7.

Example 4

Synthesis of hydroxymethylene substituted benzimidazole-2-amines

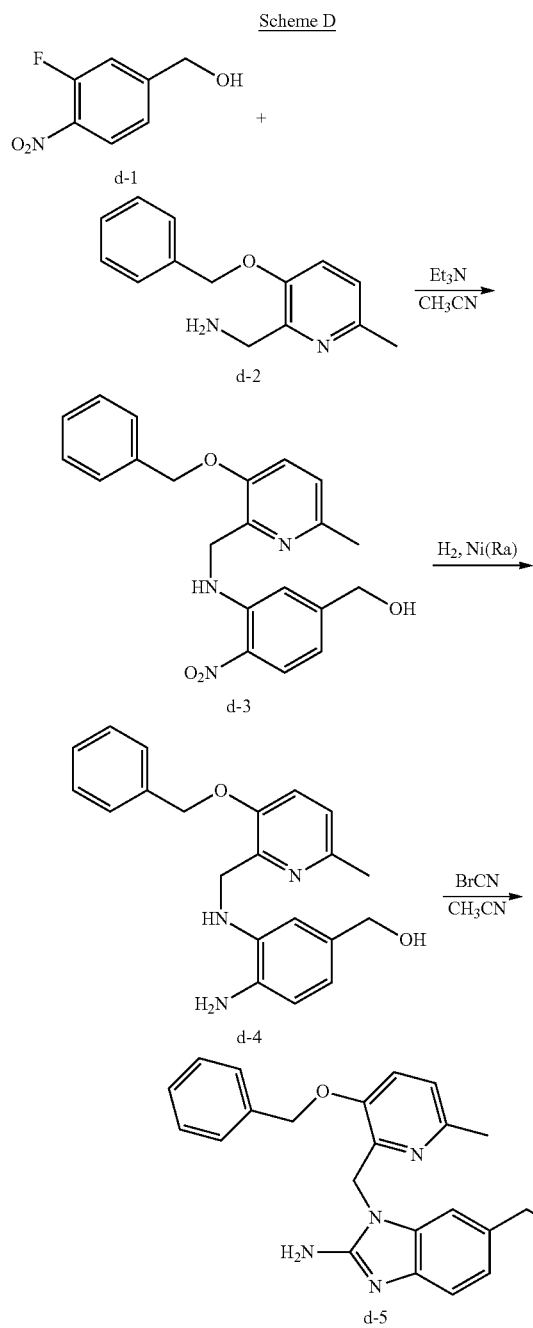

Preparation of Intermediate d-3:

A mixture of d-1 (0.0292 mol), d-2 (0.0438 mol) and NEt$_3$ (0.0584 mol) in CH$_3$CN (150 ml) was stirred and refluxed for 12 h, then cooled to room temperature and the solvent was evaporated. The mixture was poured into water and extracted with EtOAc. The organic layer was separated, dried (over MgSO$_4$), filtered and the solvent was evaporated. The residue (12.5 g) was purified by column chromatography over silica gel (eluent: CH$_2$Cl$_2$/EtOAc 96/4; 20-45 µm). Yield: 2 g of intermediate d-3 (45%, melting point: 140° C.).

Preparation of Intermediate d-4:

A mixture of d-3 (0.0081 mol) and Raney Nickel (3 g) in CH$_3$OH (100 ml) was hydrogenated at room temperature for 2 hours, then filtered over celite. Celite was washed with CH$_3$OH. The filtrate was concentrated, yielding 2.9 g of intermediate d-4 (100%).

Preparation of Intermediate d-5:

A mixture of b-4 (0.0083 mol) and BrCN (0.0091 mol) in EtOH (50 ml) was stirred and refluxed for 1 h, then cooled to room temperature and the solvent was evaporated. The residue was taken up in CH$_2$Cl$_2$. The organic layer was washed with a solution of K$_2$CO$_3$ 10%, dried (over MgSO$_4$), filtered and the solvent was evaporated. The residue (3 g) was crystallized form CH$_3$CN. The precipitate was filtered off and dried, yielding 2.2 g of intermediate d-5 (71%).

Example 5

Synthesis of arylamino substituted benzimidazole-2-amines

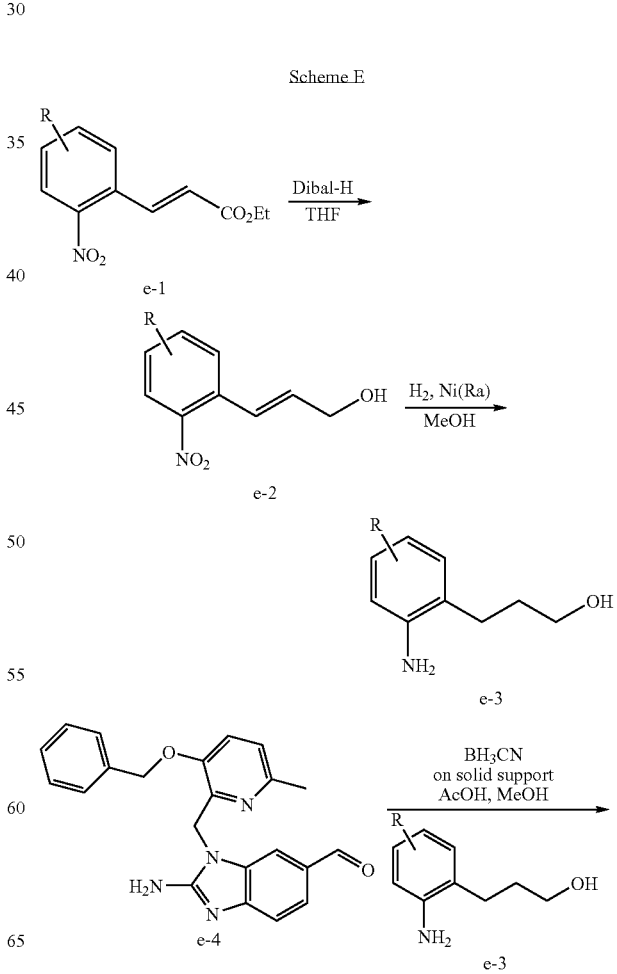

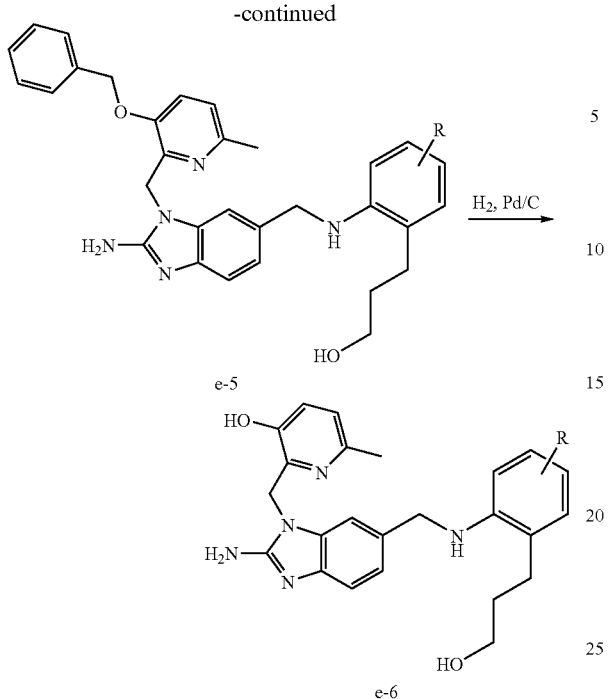

e-5 e-6

Preparation of 3-(4-methyl-2-nitro-phenyl)-prop-2-en-1-ol, intermediate (e-2)

Dibal-H (0.0255 mol) was added at −35° C. to a mixture of 3-(4-methyl-2-nitro-phenyl)-acrylic acid ethyl ester (0.0085 mol) in THF (80 ml) under $N_2$ flow. The mixture was stirred at −35° C. for 15 minutes. $H_2O$ (20 ml) was added drop wise at −35° C. under $N_2$ flow. The mixture was half-evaporated. $CH_2Cl_2$ was added. The mixture was filtered over celite. Celite was washed with $CH_2Cl_2$. The filtrate was washed with $H_2O$. The organic layer was separated, dried (over $MgSO_4$), filtered and the solvent was evaporated. Yield: 2 g of 3-(4-Methyl-2-nitro-phenyl)-prop-2-en-1-ol (e-2) (100%).

Preparation of intermediate 3-(2-Amino-4-methyl-phenyl)-propan-1-ol (e-3)

A mixture of 3-(4-Methyl-2-nitro-phenyl)-prop-2-en-1-ol (e-2) (0.0085 mol) and Raney Nickel (1.6 g) in MeOH (30 ml) was hydrogenated at room temperature for 2 hours under a 3 bar pressure, then filtered over celite. Celite was washed with $CH_3OH$. The filtrate was evaporated. Yield: 1.7 g of 3-(2-Amino-4-methyl-phenyl)-propan-1-ol (e-3) (86%, melting point: 65° C.).

Preparation of Intermediate e-5:

AcOH (10 drops) then $BH_3CN$— on solid support (0.007 mol) were added at room temperature to a mixture of e-4 (0.0035 mol) and 3-(2-amino-4-methyl-phenyl)-propan-1-ol (e-3) (0.0052 mol) in MeOH (50 ml). The mixture was filtered, and then washed with $CH_3OH$. The filtrate was evaporated. The residue was taken up in $CH_2Cl_2/CH_3OH$. The organic layer was washed with $K_2CO_3$ 10%, dried (over $MgSO_4$), filtered and the solvent was evaporated until dryness. The residue (2.7 g) was purified by column chromatography over silica gel (eluent $CH_2Cl_2/CH_3OH/NH_4OH$ 95/5/0.1). The pure fractions were collected and the solvent was evaporated. Yield: 1.3 g (71%). This fraction was crystallized from 2-propanone/diethyl ether. The precipitate was filtered off and dried. Yield: 0.026 g of intermediate e-5 (compound 128, melting point: 129° C.).

Preparation of Final Compound e-6:

A mixture of e-5 (0.0024 mol) and Pd/C (0.3 g) in $CH_3OH$ (60 ml) was hydrogenated at room temperature for 1 hour and 30 minutes under a bar pressure, and then filtered over celite. Celite was washed with $CH_3OH$. The filtrate was evaporated. The residue (1.1 g) was purified by column chromatography over silica gel (eluent $CH_2Cl_2/CH_3OH/NH_4OH$ 90/10/0.1; 15-40 μm). The pure fractions were collected and the solvent was evaporated. The residue (0.88 g) was crystallized from 2-propanone/diethyl ether. The precipitate was filtered off and dried. Yield: 0.735 g of final compound e-6 (68%, compound 90, melting point: 248° C.).

Example 6

Synthesis of arylamino substituted benzimidazole-2-amines

Scheme F

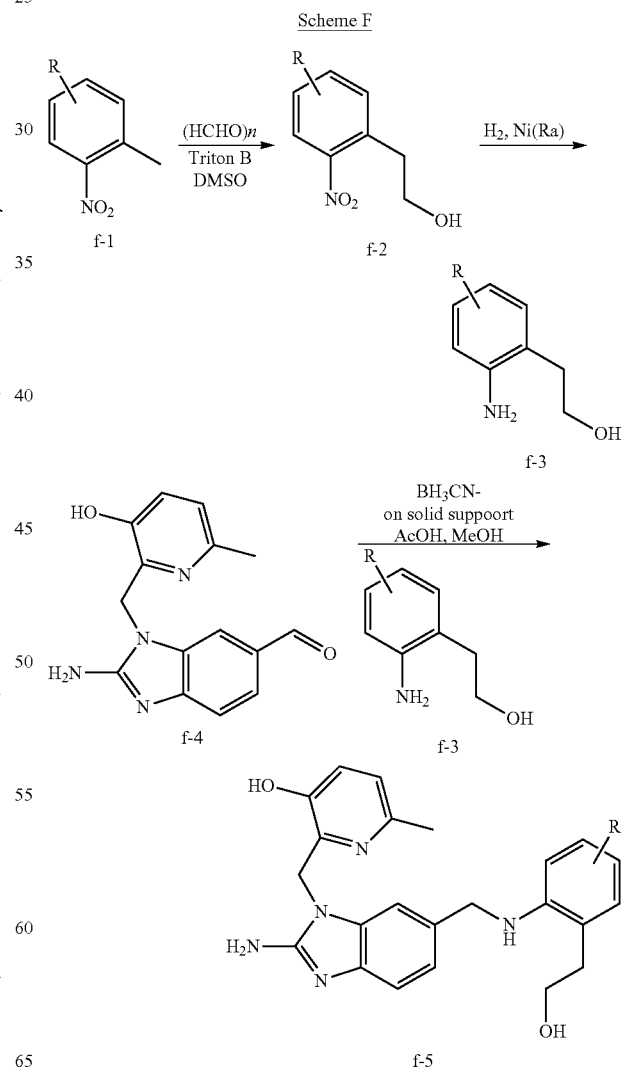

Preparation of intermediate 2-(4-Bromo-2-nitro-phenyl)-ethanol (f-2)

A mixture of 4-bromo-1-methyl-2-nitro-benzene (f-1) (0.01134 mol) and paraformaldehyde (0.009 mol) in DMSO (5 ml) and Triton-B (035 ml) was stirred at 50° C. for 2 hours, then cooled to room temperature and purified by column chromatography over silica gel (eluent: $CH_2Cl_2/CH_3OH$ 98.5/1.5; 35-70 μm). The pure fractions were collected and the solvent was evaporated. Yield: 1.18 g of 2-(4-Bromo-2-nitro-phenyl)-ethanol (f-2) (42%).

Preparation of intermediate 2-(2-Amino-4-bromo-phenyl)-ethanol (f-3)

A mixture of 2-(4-Bromo-2-nitro-phenyl)-ethanol (f-2) (0.00203 mol) and Raney Nickel (0.5 g) in MeOH (20 ml) and thiophene (0.5 ml) was hydrogenated at room temperature for 2 hours under a 3 bar pressure, then filtered over celite. Celite was washed with $CH_3OH$. The filtrate was concentrated. Yield: 1.7 g of 2-(2-Amino-4-bromo-phenyl)-ethanol (f-3) (91%).

Preparation of Final Compound f-5 (Compound 93):

This compound was synthesized according to the procedure described for compound e-5.

Example 7

Synthesis of ethynylphenylamino substituted benzimidazole-2-amines

Scheme G

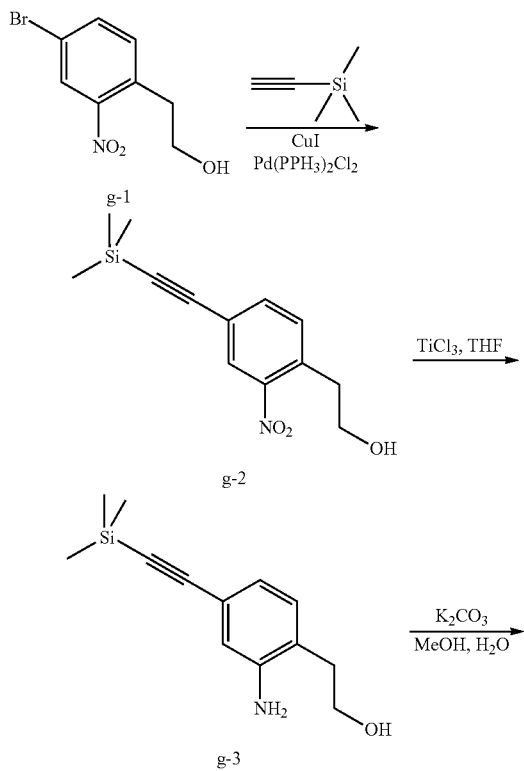

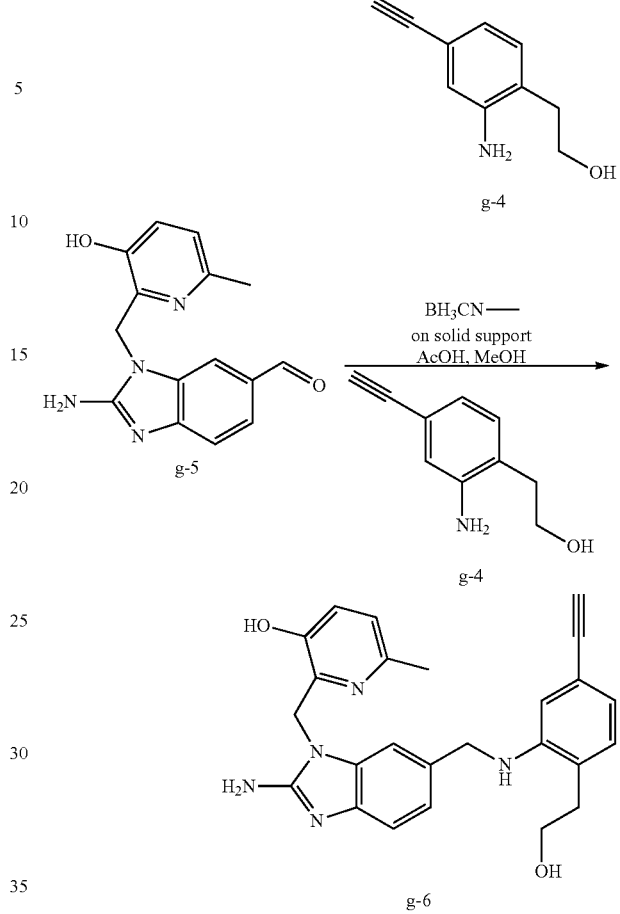

Preparation of Intermediate g-2:

Disopropyl-ethylamine (23.5 ml) was added drop wise to a mixture of g-1 (0.0047 mol), $Pd(PPh_3)_2Cl_2$ (0.0002 mol) and CuI (0.0002 mol) in THF (50 ml) under $N_2$ flow. Ethynyl-trimethyl-silane (0.0095 mol) was added drop wise at room temperature. The mixture was stirred at 50° C. for 12 hours under $N_2$ flow, poured into $H_2O$ and extracted with EtOAc. The organic layer was washed with $H_2O$, dried (over $MgSO_4$), filtered and the solvent was evaporated. The residue (3.1 g) was purified by column chromatography over silica gel (eluent: $CH_2Cl_2/CH_3OH$ 99/1). The pure fractions were collected and the solvent was evaporated. Yield: 1 g of intermediate e-2 (80%).

Preparation of Intermediate g-3:

$TiCl_3$ (0.0334 mol) was added drop wise at 0° C. to a mixture of g-2 (0.0041 mol) in THF (50 ml). The mixture was stirred at room temperature for 12 hours. EtOAc was added. The mixture was washed several times with $H_2O$, washed with a solution $K_2CO_3$ 10%, and finally with $H_2O$. The organic layer was separated, dried (over $MgSO_4$), filtered and the solvent was evaporated. Yield: 0.82 g of intermediate g-3 (84%).

Preparation of Intermediate g-4:

A mixture of g-3 (0.0022 mol) and $K_2CO_3$ (0.0066 mol) in $CH_3OH$ (20 ml) and $H_2O$ (4 ml) was stirred at room temperature for 2 hours. The solvent was evaporated until dryness. The residue was taken up in $CH_2Cl_2/H_2O$. The organic layer was washed with $H_2O$, dried (over $MgSO_4$), filtered and the solvent was evaporated, yielding: 0.29 g of intermediate g-4 (81%).

Preparation of Final Compound g-6:

This compound was synthesized according to the procedure described for compound c-5 (yield: 33%, compound 92, melting point: 252° C.).

Example 8

Synthesis of alkylsulfonylphenylamino substituted benzimidazole-2-amines

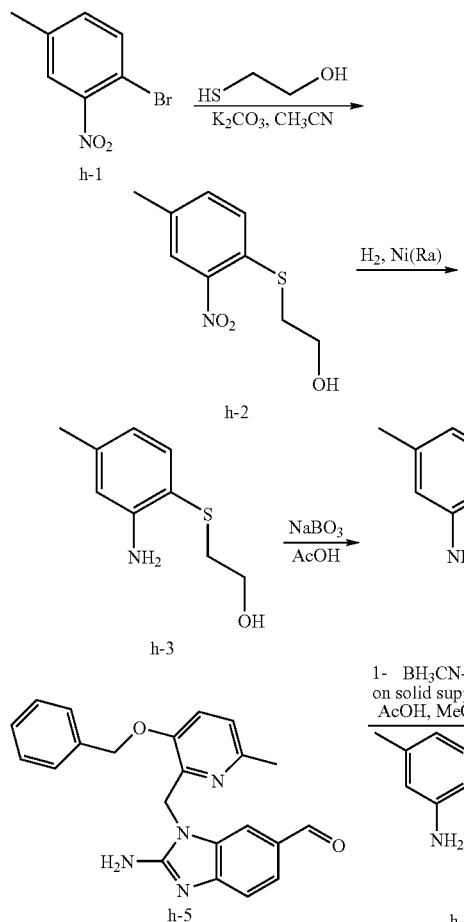

Preparation of Intermediate h-2:

A mixture of h-1 (0.0092 mol), 2-mercapto-ethanol (0.0102 mol) and $K_2CO_3$ (0.0139 mol) in $CH_3CN$ (50 ml) was stirred and refluxed for 6 hours, then poured into $H_2O$ and extracted with EtOAc. The organic layer was washed with $H_2O$, dried (over $MgSO_4$), filtered and the solvent was evaporated. Yield: 2.1 g of intermediate h-2 (100%). This fraction was used directly in the next reaction step.

Preparation of Intermediate h-3:

A mixture of h-2 (0.0098 mol) and Raney Nickel (2 g) in $CH_3OH$ (50 ml) was hydrogenated at room temperature for 1 hour under a 3 bar pressure, then filtered over celite. Celite was washed with $CH_3OH$. The filtrate was evaporated. Yield: 1.5 g of intermediate h-3 (83%).

Preparation of Intermediate h-4:

Sodium perborate ($NaBO_3$, 0.005 mol) was added portion wise at 0° C. to a mixture of h-3 (0.0025 mol) in AcOH (5 ml). The mixture was stirred at room temperature for 12 hours, poured on ice, basified with $K_2CO_3$ and extracted with EtOAc. The organic layer was separated, dried (over $MgSO_4$), filtered and the solvent was evaporated until dryness. The residue (0.46 g) was purified by column chromatography over silica gel (eluent $CH_2Cl_2/CH_3OH$ 98/2; 10 μm). The pure fractions were collected and the solvent was evaporated. Yield: 0.16 g of intermediate h-4 (30%).

Preparation of Final Compound h-6 (Compound 100, Melting Point: >260%):

This compound was synthesized according to the procedure described for compound e-6.

Example 9

Synthesis of phenylamino substituted benzimidazole-2-amines

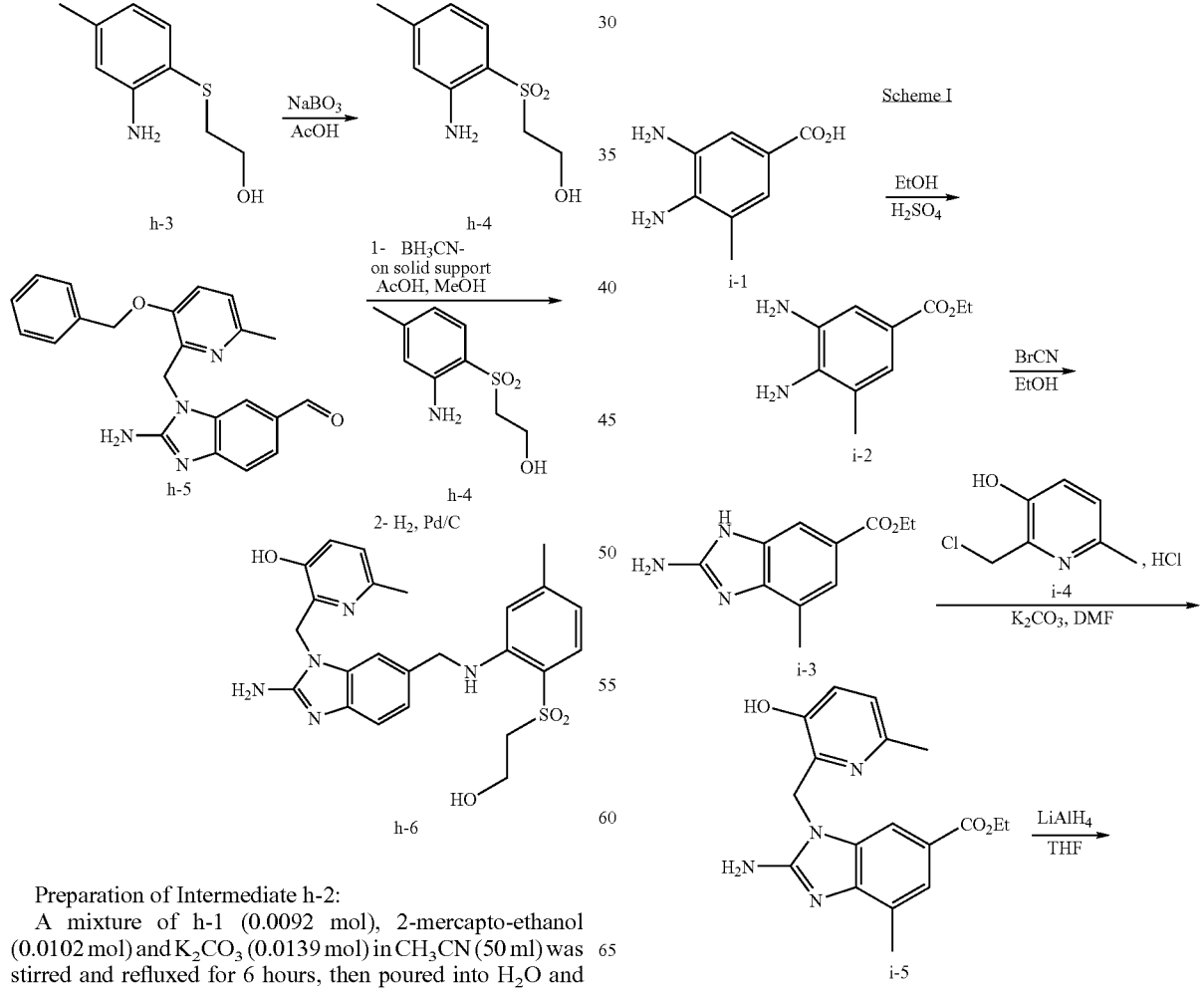

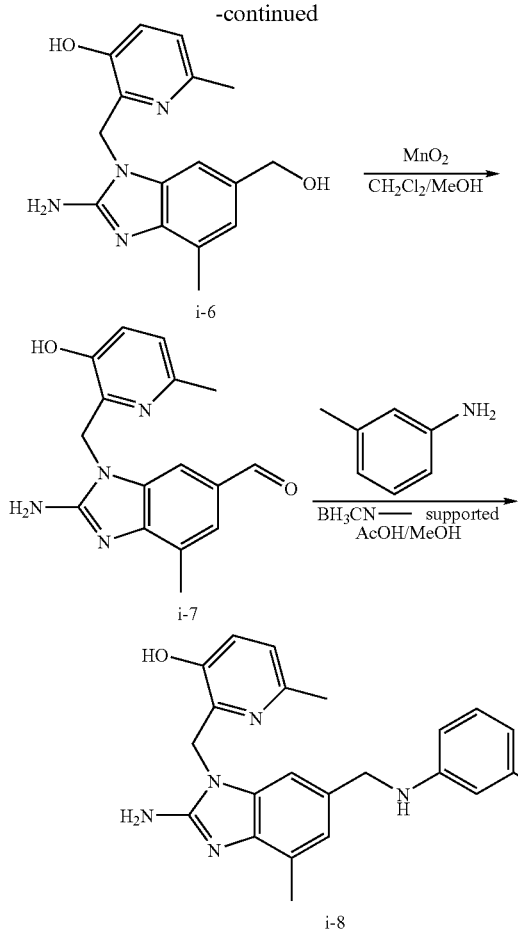

mixture was filtered through a pad of celite. The pad was washed with water, then with THF. The filtrate was evaporated. The residue was taken up in CH$_2$Cl$_2$/methanol. The organic layer was separated, dried over magnesium sulfate, filtered and the solvent was evaporated, yielding 1.7 g of i-6 (100%).

Preparation of Intermediate i-7:

MnO$_2$ (4 g) was added portion wise at room temperature to a mixture of i-6 (0.0013 mol) in CH$_2$Cl$_2$ (20 ml) and methanol (2 ml). The reaction was stirred at room temperature for 30 minutes, and then filtered through a pad of celite. The pad was washed with CH$_2$Cl$_2$/methanol. The filtrate was evaporated, yielding 0.5 g of i-7 (69%).

Preparation of Compound I-8:

A mixture of i-7 (0.0006 mol), m-methylaniline (0.0008 mol), supported cyanoborohydride (0.001 mol) and acetic acid (6 drops) in methanol (20 ml) was stirred at room temperature for 48 hours, then filtered and washed with CH$_2$Cl$_2$/methanol. The filtrate was evaporated. The residue (0.32 g) was purified by column chromatography over silica gel (eluent CH$_2$Cl$_2$/methanol/NH$_4$OH 90/10/0.5; 10 μm). The pure fractions were collected and the solvent was evaporated. The residue (0.054 g, 31%) was crystallized from diethyl ether. The precipitate was filtered off and dried, yielding 0.036 g (21%) of 2-[2-amino-4-methyl-6-(m-tolylamino-methyl)-benzoimidazol-1-ylmethyl]-6-methyl-pyridin-3-ol.

Example 10

Synthesis of aminoalkyl substituted benzimidazole-2-amines

Scheme J

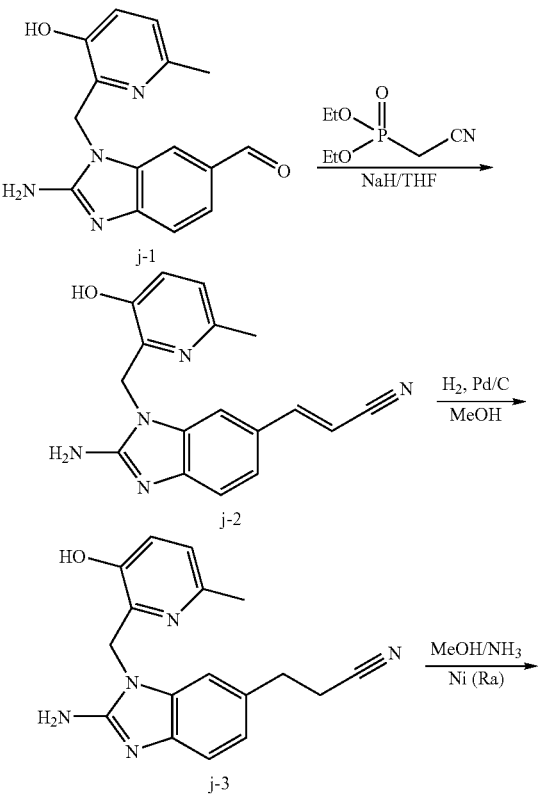

Preparation of Intermediate i-2:

A mixture of i-1 (0.0185 mol) in ethanol (60 ml) and H$_2$SO$_4$ 36N (5 ml) was stirred and refluxed for 24 hours. The solvent was evaporated. The residue was taken up in CH$_2$Cl$_2$. The organic layer was washed with a solution of K$_2$CO$_3$ 10% in water, dried over magnesium sulfate, filtered and the solvent was evaporated, yielding 3.2 g of i-2 (89%). This crude fraction was used directly in the next step.

Preparation of Intermediate i-3:

A mixture of i-2 (0.0144 mol) and BrCN (0.0158 mol) in ethanol (30 ml) was stirred and refluxed for 2 hours. The solvent was evaporated. The residue was taken up in K$_2$CO$_3$ 10% in water, extracted with CH$_2$Cl$_2$/methanol. The organic layer was separated, dried over magnesium sulfate, filtered and the solvent was evaporated, yielding 2.3 g of i-3 (73%). This crude fraction was used directly in the next step.

Preparation of Intermediate i-5:

A mixture of c-3 (0.0095 mol), i-4 (0.0115 mol) and K$_2$CO$_3$ (0.0335 mol) in dimethylformamide (50 ml) was stirred at 70° C. for 12 hours, then cooled to room temperature and taken up in 2-propanone. The precipitate was filtered and washed with 2-propanone. The filtrate was evaporated. The residue (4.5 g) was crystallized from CH$_2$Cl$_2$/methanol. The precipitate was filtered off and dried, yielding 2.4 g of c-5 (74%, melting point >250° C.).

Preparation of Intermediate i-6:

LiAlH$_4$ (0.0106 mol) was added portion wise at 5° C. to a mixture of i-5 (0.0052 mol) in THF (50 ml) under nitrogen flow. The reaction was stirred at 5° C. for 30 minutes then at room temperature for 6 hours. Water was added carefully. The

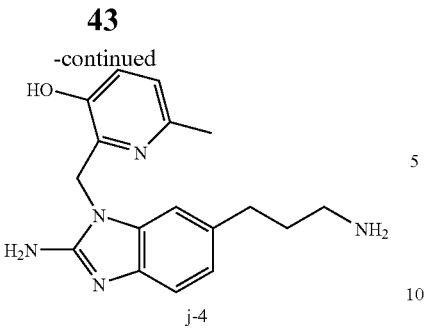

j-4

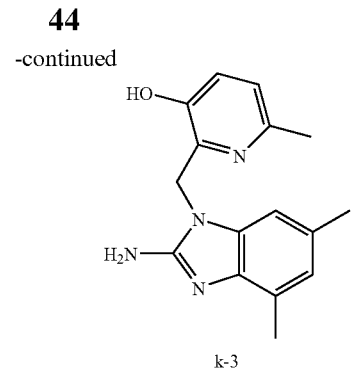

k-3

Preparation of Intermediate 3-2:

Diethylcyanomethyl phosphonate (0.0021 mol) was added drop wise at 5° C. to a solution of NaH (0.0043 mol) in THF (10 ml) under nitrogen flow. The mixture was stirred at 5° C. for 30 minutes under nitrogen flow. j-1 (0.0007 mol) was added portion wise. The mixture was stirred at 5° C. for 1 hour, and then stirred at room temperature for 12 hours and poured onto ice. The aqueous layer was saturated with $K_2CO_3$ and extracted with $CH_2Cl_2$/methanol. The organic layer was separated, dried over magnesium sulfate, filtered and the solvent was evaporated, yielding 0.5 g of j-2 (100%). This crude product was used directly in the next reaction step.

Preparation of Intermediate j-3:

A mixture of j-2 (0.0007 mol) and Pd/C (0.1 g) in methanol (20 ml) was hydrogenated at room temperature for 12 hours under a 3 bar pressure, and then filtered through a pad of celite. The pad was washed with methanol. The filtrate was evaporated. The residue was purified by column chromatography over silica gel (eluent $CH_2Cl_2$/methanol/$NH_4OH$ 90/10/0.5; 15-40 μm). The pure fractions were collected and the solvent was evaporated. The residue (0.25 g, 100%) was crystallized from $CH_3CN$/diisopropyl ether. The precipitate was filtered off and dried, yielding 0.055 g of j-3 (25%, compound 198, melting point 242° C.).

Preparation of Compound j-4:

A mixture of j-3 (0.0006 mol) and Raney Nickel (0.2 g) in methanol/$NH_3$ 7N (30 ml) was hydrogenated at room temperature for 12 hours under a 3 bar pressure, and then filtered through a pad of celite. The pad was washed with methanol. The filtrate was evaporated. The residue was dissolved in isopropanol/HCl and converted into the hydrochloric acid salt. The precipitate was filtered off and dried, yielding 0.058 g of j-4 (22%, compound 196, melting point: 195° C.).

Example 11

Synthesis of dimethyl substituted benzimidazole-2-amines

Scheme K

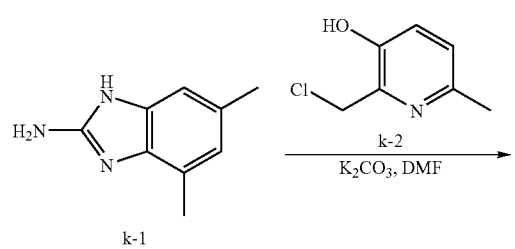

A mixture of k-1 (0.031 mol), k-2 (0.0372 mol) and $K_2CO_3$ (0.0183 mol) in dimethylformamide (150 ml) was stirred at 70° C. for 24 hours. The solvent was evaporated. The residue was taken up in $CH_2Cl_2$. The organic layer was washed with water, dried over magnesium sulfate, filtered and the solvent was evaporated. The residue (12 g) was purified by column chromatography over silica gel (eluent: $CH_2Cl_2$/methanol/$NH_4OH$ 90/10/0.5; 20-45 μm). The pure fractions were collected and the solvent was evaporated. The residue (6.8 g, 78%) was crystallized from $CH_3CN$/diisopropyl ether. The precipitate was filtered off and dried, yielding 0.506 g of k-3 (compound 199, melting point: >260° C.).

Example 12

Synthesis of phenyl(hydroxymethyl) substituted benzimidazole-2-amines

Scheme L

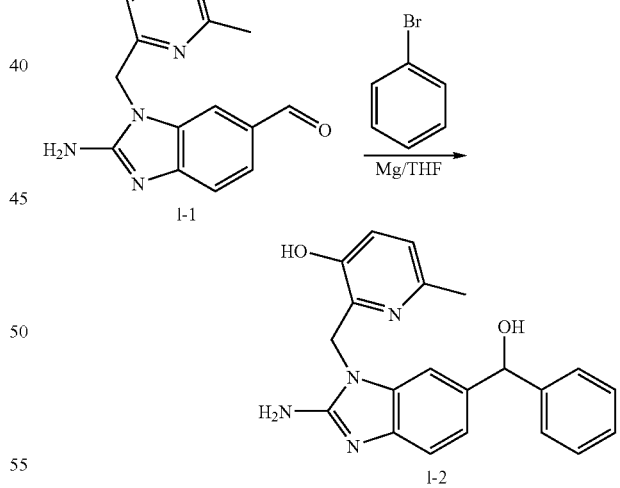

Bromobenzene (0.0026 mol) was added drop wise to a mixture of magnesium (0.0026 mol) in THF (3 ml) under nitrogen flow. The mixture was stirred at room temperature under nitrogen flow until the magnesium disappeared. l-1 (0.0002 mol) was added portion wise. The mixture was stirred at room temperature for 2 hours. A solution of $NH_4Cl$ 10% in water (3 ml) was added drop wise at 0° C. The mixture was extracted with $CH_2Cl_2$. The organic layer was separated, dried over magnesium sulfate, filtered and the solvent was evaporated. The residue (0.2 g) was purified by column chromatography over silica gel (eluent: $CH_2Cl_2$/methanol/$NH_4OH$ 90/10/0.5; 5 μm). The pure fractions were collected and the solvent was evaporated, yielding 0.035 g of l-2 (compound 197, 36%).

Example 13

Synthesis of 1-(pyridinylmethyl)-6-benzoylamido-benzimidazoles

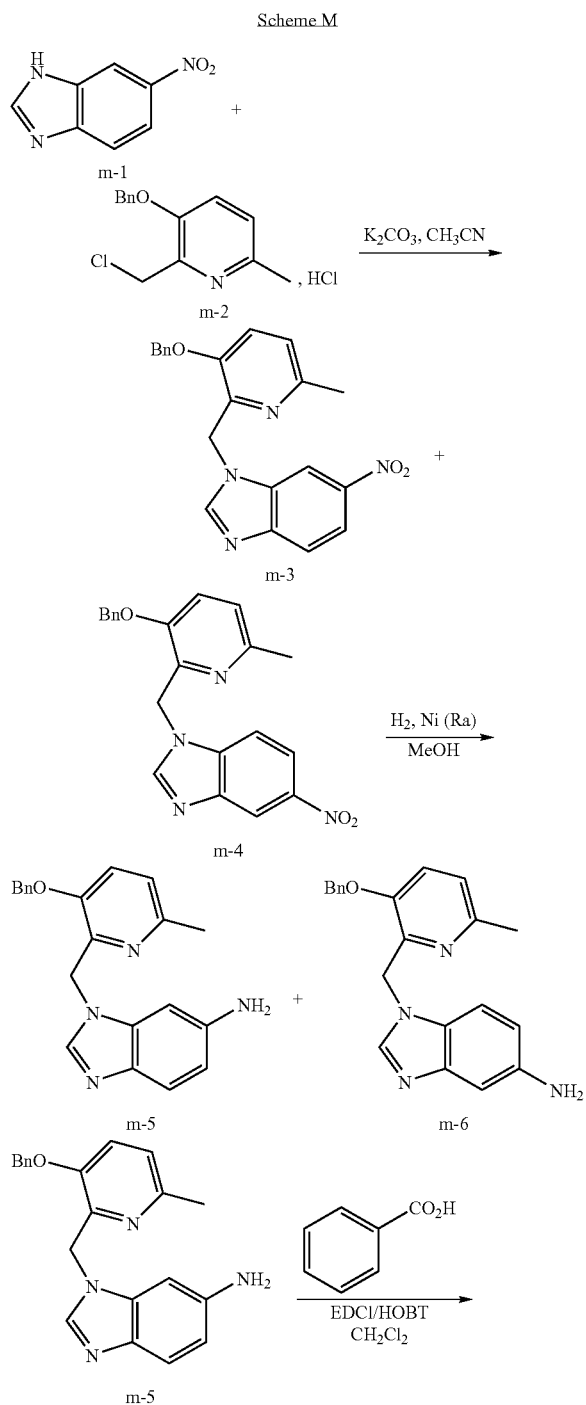

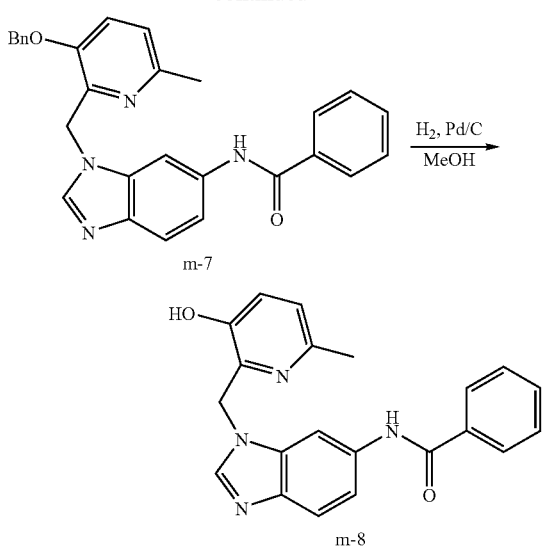

Preparation of the Mixture of Intermediates m-3 and m-4:

m-2 (0.0368 mol) was added to a mixture of m-1 (0.03 mol) and $K_2CO_3$ (0.107 mol) in $CH_3CN$ (200 ml). The reaction was stirred and refluxed 12 hours. The solvent was evaporated. The residue was taken up in $CH_2Cl_2$. The organic layer was washed with water, dried over magnesium sulfate, filtered and the solvent was evaporated, yielding 15.5 g of a mixture of m-3 and m-4 (100%).

Preparation of Intermediates m-5 and m-6:

A mixture of m-3 and m-4 (0.03 mol) and Raney Nickel (11 g) in methanol (200 ml) was hydrogenated at room temperature for 1 hour under a 3 bar pressure, and then filtered through a pad of celite. The pad was washed with methanol. The filtrate was evaporated. The residue (12 g) was purified by column chromatography over silica gel (eluent: $CH_2Cl_2$/methanol/$NH_4OH$ 97/3/0.1; 20-45 μm). The pure fractions were collected and the solvent was evaporated, yielding 5 g of m-5 (48%) and 4.8 g of m-6 (45%).

Preparation of Intermediate m-7:

Benzoic acid (0.0005 mol) was added at room temperature to a mixture of m-5 (0.0005 mol) and 1-(3-dimethylaminopropyl)-3-ethylcarbodiimide hydrochloride (0.0006 mol) in $CH_2Cl_2$ (5 ml). The reaction was stirred at room temperature for 12 hours and poured into water. The organic layer was separated, dried over magnesium sulfate, filtered and the solvent was evaporated, yielding: 027 g of m-7 (100%). The crude compound was used in the next reaction step.

Preparation of Compound m-8:

A mixture of m-7 (0.0005 mol) and Pd/C (0.05 g) in methanol (30 ml) was hydrogenated at room temperature for 8 hours under a 5 bar pressure, and then filtered through a pad of celite. The pad was washed with methanol. The filtrate was evaporated. The residue (0.42 g) was purified by column chromatography (eluent: $CH_2Cl_2$/methanol/$NH_4OH$ 95/5/0.5; 10 μm). The pure fractions were collected and the solvent was evaporated. The residue (0.09 g, 43%) was crystallized from ethanol. The precipitate was filtered off and dried, yielding 0.057 g of m-8 (27%, compound 198, melting point: >250° C.).

Example 14

Synthesis of 1-(pyridylmethyl)5- and 6-formyl-benzimidazoles

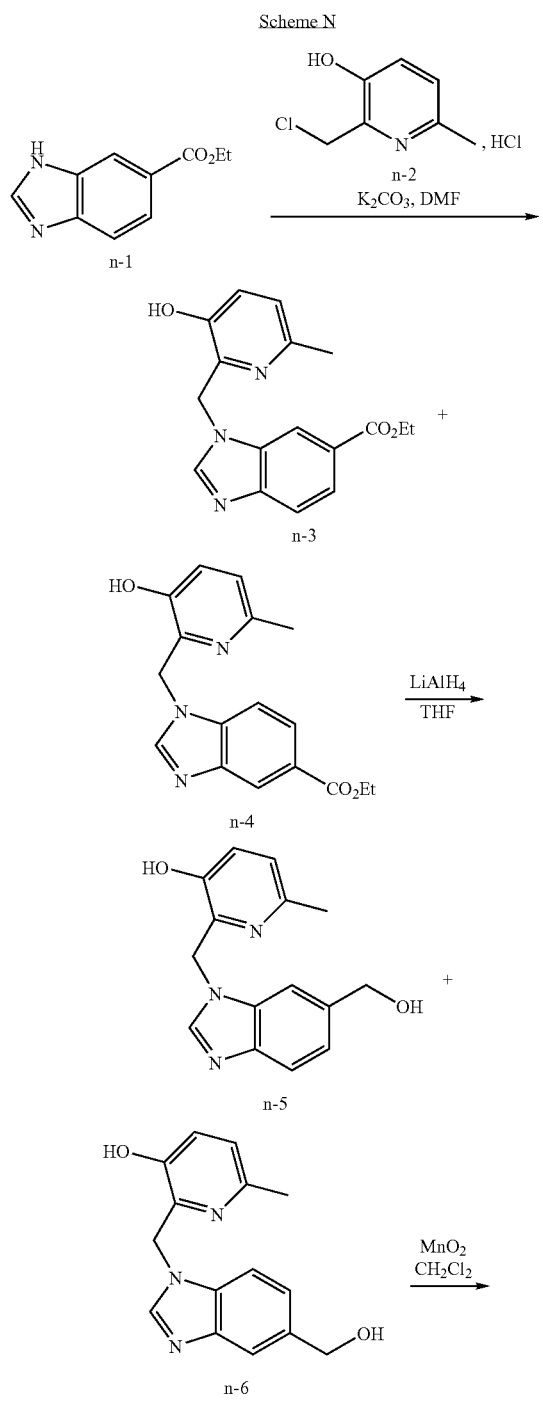

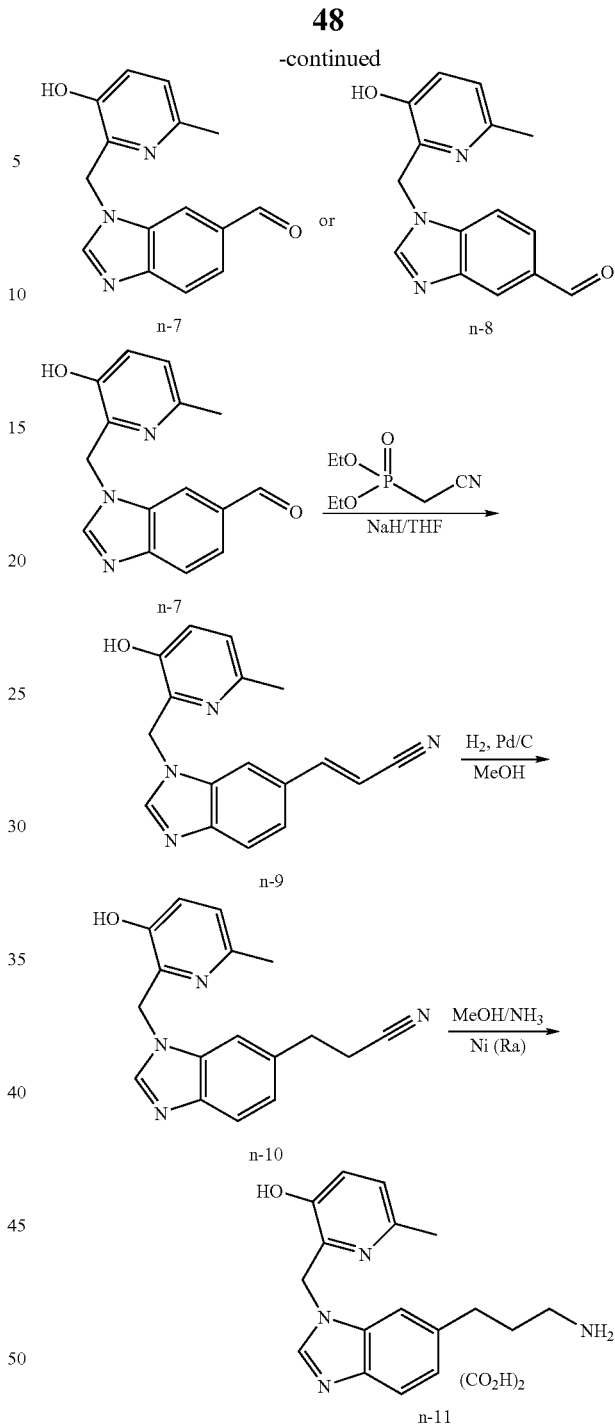

Preparation of the Mixture of Intermediates n-3 and n-4:

A mixture of n-1 (0.0708 mol), n-2 (0.077 mol) and K$_2$CO$_3$ (0.02455 mol) in dimethylformamide (130 ml) was stirred at 70° C. for 24 hours. The solvent was evaporated. The residue was taken up in CH$_2$Cl$_2$. The organic layer was washed with water, dried over magnesium sulfate, filtered and the solvent was evaporated. The residue was taken up in acetone. The precipitate was filtered off and dried, yielding 16.2 g of a mixture of n-3 and n-4 (74%).

Preparation of Intermediates n-5 and n-6:

LiAlH$_4$ (0.052 mol) was added portion wise at 5° C. to a mixture of n-5 and n-6 (0.026 mol) in THF (160 ml) under nitrogen flow. The reaction was stirred at 5° C. for 2 hours.

Ethyl acetate and water were added carefully. The mixture was filtered through a pad of celite. The pad was washed with water, then with THF. The filtrate was evaporated. The residue was taken-up in CH$_2$Cl$_2$/methanol. The organic layer was separated, dried over magnesium sulfate, filtered and the solvent was evaporated, yielding 13 g of the mixture of n-5 and n-6 (92%). The two compounds were separated by column chromatography over silica gel (eluent: CH$_2$Cl$_2$/methanol/NH$_4$OH 90/10/0.5; 10 μm).

Preparation of Intermediate n-7:

MnO$_2$ (36 g) was added to a mixture of n-5 (0.014 mol) in CH$_2$Cl$_2$/THF (400 ml) and methanol (20 ml). The reaction was stirred at room temperature for 3 hours, and then filtered through a pad of celite. The pad was washed with CH$_2$Cl$_2$/methanol. The filtrate was evaporated, yielding 3.5 g of n-7 (93%). This product was used directly in the next reaction step.

Preparation of Intermediate n-9:

Diethylcyanomethyl phosphonate (0.0033 mol) was added drop wise at 5° C. to a mixture of NaH (0.0011 mol) in THF (15 ml) under nitrogen flow. The mixture was stirred at 5° C. for 30 minutes under nitrogen flow. A solution of n-7 (0.0011 mol) in THF (15 ml) was added drop wise at 5° C. The reaction was stirred at 5° C. for 1 hour, and then at room temperature for 2 hours and poured into water. The aqueous layer was saturated with K$_2$CO$_3$ and extracted with ethylacetate/methanol. The organic layer was separated, dried over magnesium ulphate, filtered and the solvent was evaporated, yielding 1 g of n-9 (100%, compound 189, melting point: >250° C., mixture E/Z (90/10)).

Preparation of Intermediate n-10:

A mixture of n-9 (0.0007 mol) and Pd/C (0.1 g) in methanol (15 ml) was hydrogenated at room temperature for 12 hours under a 3 bar pressure, and then filtered through a pad of celite. The pad was washed with methanol. The filtrate was evaporated, yielding 0.2 g of n-10 (91%). This crude product was used directly in the next reaction step.

Preparation of Compound n-11:

A mixture of n-10 (0.0006 mol) and Raney Nickel (0.2 g) in methanol/NH$_3$ 7N (20 ml) was hydrogenated at room temperature for 4 hours under a 3 bar pressure, and then filtered through a pad of celite. The pad was washed with methanol. The filtrate was evaporated. The residue (0.33 g) was purified by column chromatography over silica gel (eluent: CH$_2$Cl$_2$/methanol/NH$_4$OH 85/14/1; 15-35 μm), yielding 0.128 g of the free base of n-11 (72%). The compound was dissolved in CH$_3$CN and converted into the ethanedioic acid salt. The precipitate was filtered off and dried, yielding 0.031 g of n-11 (10%, compound 188, melting point 205° C.).

Example 15

Synthesis of 1-(pyridylmethyl)-6-aminomethylbenzimidazoles

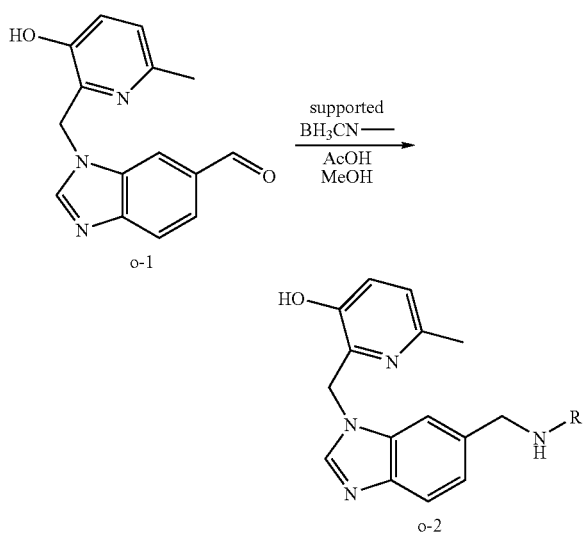

Meta-chloroaniline (0.000224 mol) was added to solution of o-1 (0.187 mmol) in methanol (5 ml). Acetic acid (1 drops) and cyano borohydride on solid support (0.224 mmol) were then added. The reaction was carried out at room temperature for 48 hours. The supported reagent was filtered off. The solvent was evaporated. The residue was purified by column chromatography over silica gel (eluent CH$_2$Cl$_2$/CH$_3$OH/NH$_4$OH 90/10/0.5; 10 μm). The pure fractions were collected and the solvent was evaporated, yielding 0.044 g (62%, compound 186) of 2-{6-[(3-chloro-phenylamino)-methyl]-benzoimidazol-1-ylmethyl}-6-methyl-pyridin-3-ol.

Example 16

Synthesis of 1-(pyridylmethyl)-6-aminomethyl-benzimidazole-2-amines

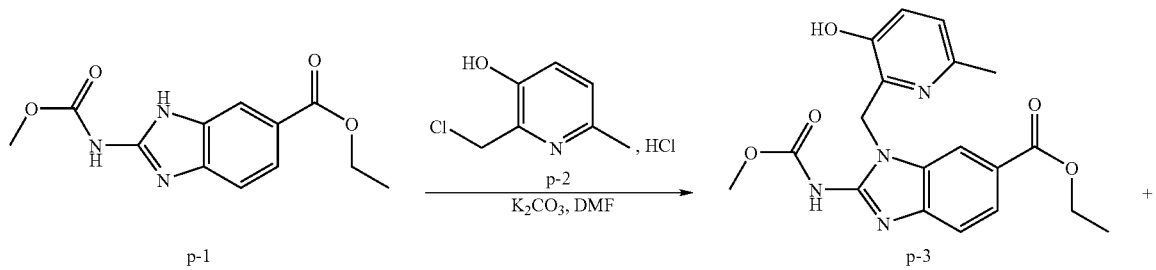

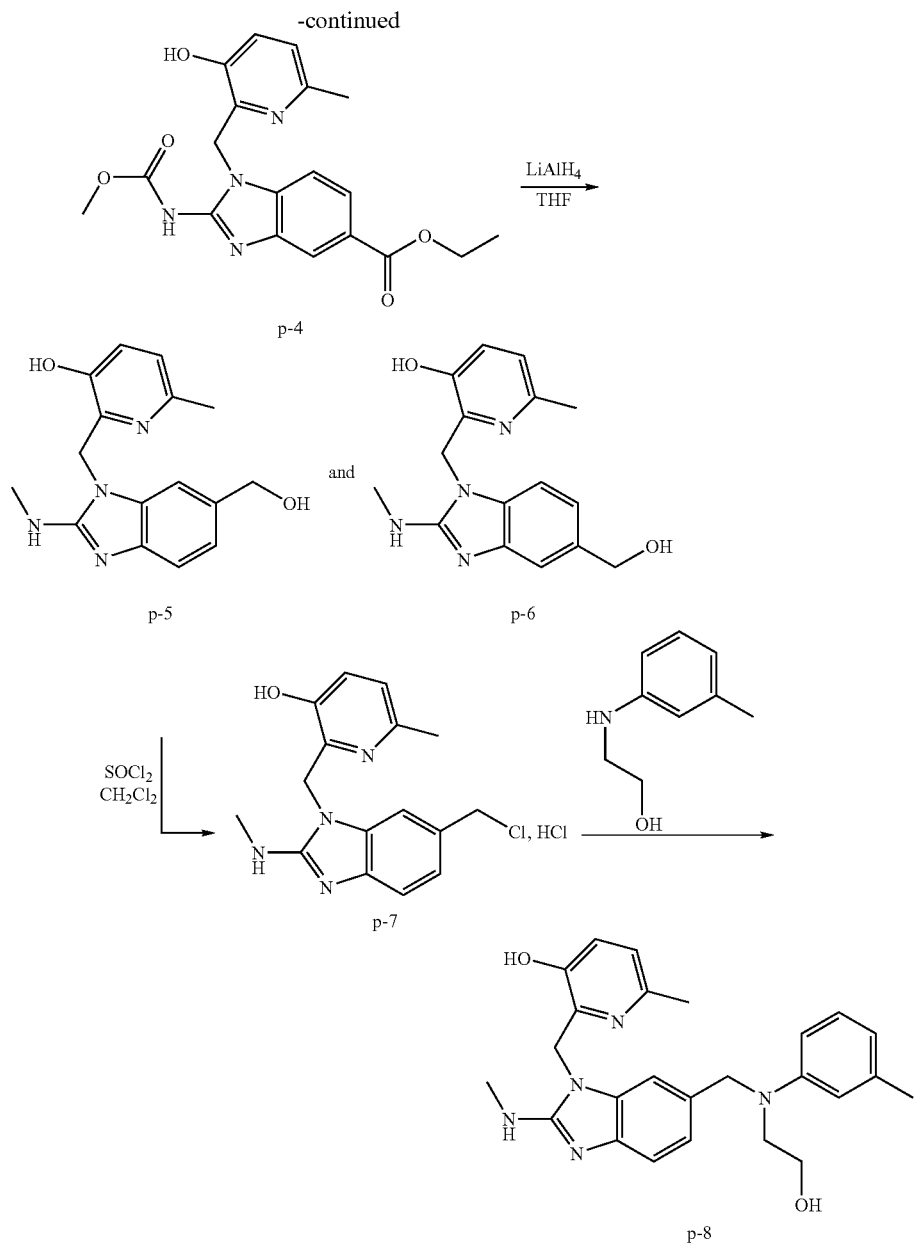

Preparation of Intermediates p-3

Intermediate p-3 was prepared from p-1 and p-2 (which is identical to k-2) following the same procedures as for the preparation of k-3.

Preparation of Intermediates p-5 and p-6

LiAlH$_4$ (0.0198 mol) was added portion wise to a solution of p-3 and p-4 (0.00494 mol; intermediates prepared analogous to intermediates c-3 and c-4) in tetrahydrofuran (50 ml) at 5° C. under N$_2$ flow. The reaction was stirred at 5° C. for 0.5 hour and then at 40° C. for 12 hours. The reaction was cooled down to 5° C. and ethylacetate and water were added drop wise very carefully. The solution was filtered over celite. The pad was rinsed with water and tetrahydrofuran. The solution was saturated with K$_2$CO$_3$ powder and extracted with a mixture CH$_2$Cl$_2$/methanol (90/10). The organic layer was separated, dried (over MgSO$_4$) and evaporated until dryness. The two isomers were isolated by column chromatography over silica gel (eluent CH$_2$Cl$_2$/CH$_3$OH/NH$_4$OH 90/10/1; 15-40 μm). The pure fractions were collected and the solvent was evaporated, yielding 0.21 g of p-5 (14%, melting point: >260° C.) and 0.35 g of p-6 (24%, melting point: >260° C.).

Preparation of Intermediate p-7 and Compound p-8

2-(6-Chloromethyl-2-methylamino-benzoimidazol-1-yl-methyl)-6-methyl-pyridin-3-ol hydrochloride salt (prepared analogous to the preparation of intermediate b-2) was used as starting material to prepare 2-(6-{[(2-hydroxy-ethyl)-m-tolyl-amino]-methyl}-2-methylamino-benzoimidazol-1-yl-methyl)-6-methyl-pyridin-3-ol (compound 188, melting point: 204° C.) in an analogous way to the preparation of compounds of formula b-3.

Example 17

Synthesis of 1-quinolylmethyl-6-aminomethylbenzimidazole-2-amines

Scheme Q

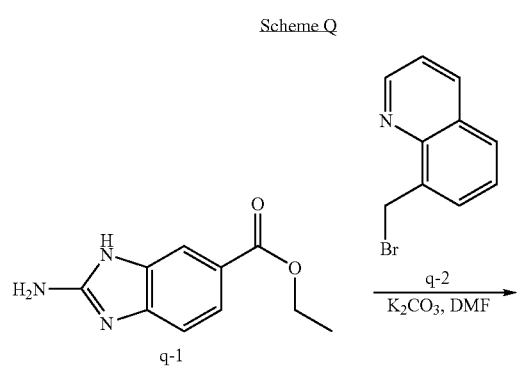

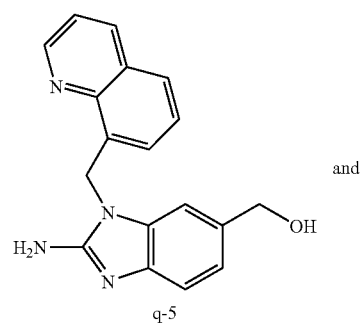

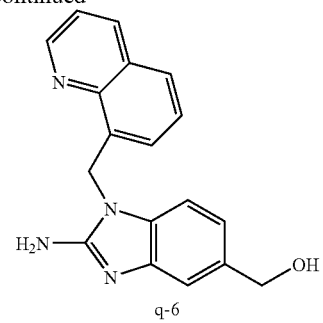

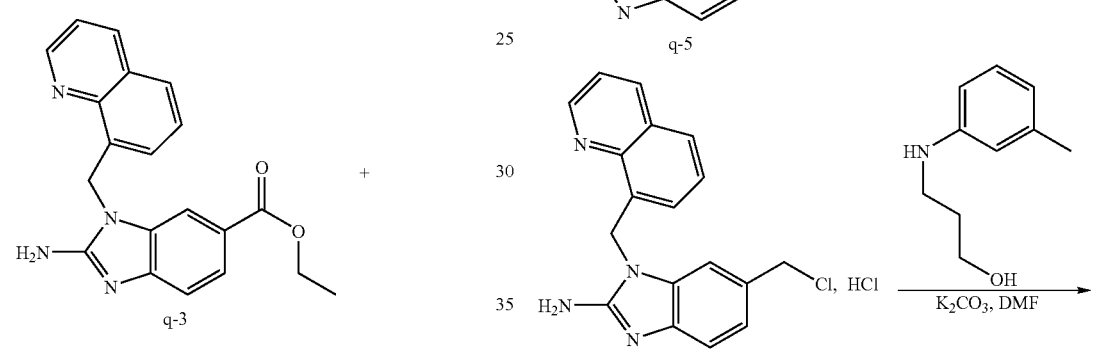

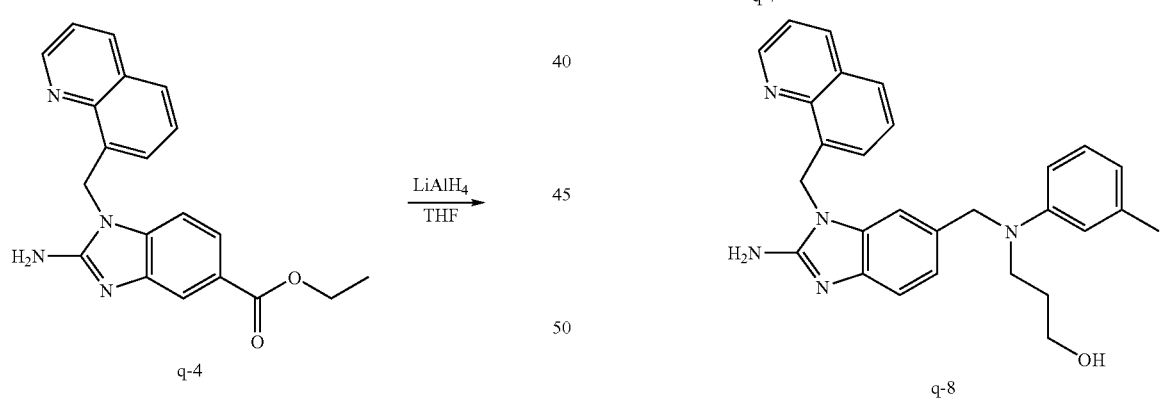

Synthesis of Intermediates q-5 and q-6:

These intermediates were synthesized analogous to the procedure described for intermediates c-5 and c-6. The separation of the two isomers was performed by column chromatography over silica gel (eluent $CH_2Cl_2/CH_3OH/NH_4OH$ 92/8/0.5; 15-40 µm). The pure fractions were collected and the solvent was evaporated, yielding 0.43 g of (2-amino-3-quinolin-8-ylmethyl-3H-benzoimidazol-5-yl)-methanol (q-5, 18%, compound 222, melting point: 230° C.) and 0.24 g of (2-amino-1-quinolin-8-ylmethyl-1H-benzoimidazol-5-yl)-methanol (q-6, compound 224, 10%, melting point: >260° C.).

55

Preparation of Intermediate q-7 and compound q-8

6-Chloromethyl-1-quinolin-8-ylmethyl-1H-benzoimidazol-2-ylamine hydrochloride salt (prepared analogously to the preparation of intermediate d-2) was used as starting material to prepare 3-[(2-amino-3-quinolin-8-ylmethyl-3H-benzoimidazol-5-ylmethyl)-m-tolyl-amino]-propan-1-ol (compound 222, melting point: 191° C.) in an analogous way to the preparation of compounds of formula d-3.

Example 18

Synthesis of bicyclic intermediates R¹-G-W

Scheme R

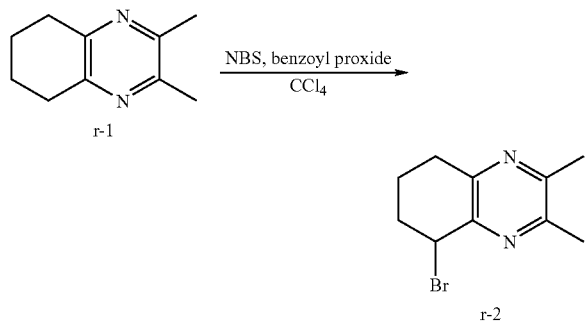

A mixture of 2,3-dimethyl-5,6,7,8-tetrahydro-quinoxaline (0.0198 mol), NBS (0.0198 mol) and benzoyl peroxide (0.0017 mol) in CCl₄ (237 ml) was stirred and refluxed for 30 minutes, and then filtered. The filtrate was evaporated. The residue was purified by column chromatography over silica gel (eluent: CH₂Cl₂/CH₃OH 100/0 and 95/5; 35-70 μm). The pure fractions were collected and the solvent was evaporated. Yield: 2.61 g of intermediate r-2 (55%).

Example 19

Synthesis of Intermediates R¹-G-W

Scheme S

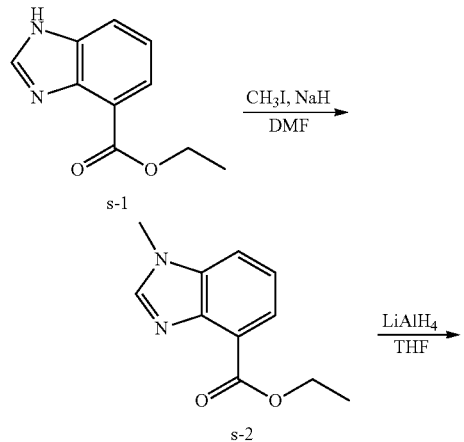

56

-continued

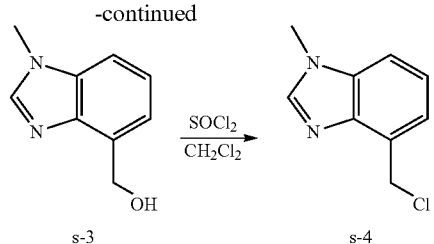

Synthesis of Intermediate s-2:

NaH (0.054 mol) was added portion wise at 5° C. under N₂ flow to a mixture of 1H-benzoimidazole-4-carboxylic acid ethyl ester (0.045 mol) in DMF (50 ml). The mixture was stirred at 0° C. under N₂ flow for 1 hour. CH₃I (0.045 mol) was added drop wise at 0° C. under N₂ flow. The mixture was stirred at room temperature under N₂ flow for 2 hours, hydrolyzed with ice water and extracted with CH₂Cl₂. The organic layer was separated, washed several times with H₂O, dried (over MgSO₄), filtered and the solvent was evaporated. The residue (10.5 g) was purified by column chromatography over silica gel (eluent CH₂Cl₂/CH₃OH 97/3; 20-45 μm). Two pure fractions were collected and their solvents were evaporated. Yield: 7 g of intermediate s-2 (76%, melting point: 86° C.).

Synthesis of Intermediate s-3:

LiAlH₄ (0.0342 mol) was suspended portion wise at 0° C. under N₂ flow in THF (100 ml). A solution of s-2 (0.0342 mol) in a small amount of THF was added drop wise at 0° C. under N₂ flow. The mixture was stirred at 0° C. for 2 hours, hydrolyzed with EtOAc and H₂O, decanted and extracted with EtOAc. The organic layer was separated, washed with H₂O, dried (over MgSO₄), filtered and the solvent was evaporated. The residue (4.3 g) was purified by column chromatography over silica gel (eluent: CH₂Cl₂/CH₃OH/NH₄OH 97/3/0.1; 15-40 μm). The desired fractions were collected and the solvent was evaporated. Yield: 2.6 g of intermediate s-3 (47%, melting point: 116° C.).

Synthesis of Intermediate s-4:

SOCl₂ (0.0222 mol) was added drop wise at 5° C. to a solution of s-3 (0.0148 mol) in CH₂Cl₂ (70 ml). The mixture was stirred at room temperature for 2 hours, poured on ice, basified with K₂CO₃ 10% and extracted with CH₂Cl₂. The organic layer was separated, washed with H₂O, dried (over MgSO₄), filtered and the solvent was evaporated. Yield: 2.8 g of intermediate s-4 (100%). The product was used without further purification.

Example 20

Synthesis of 1-substituted benzimidazole-2-amines

Scheme T

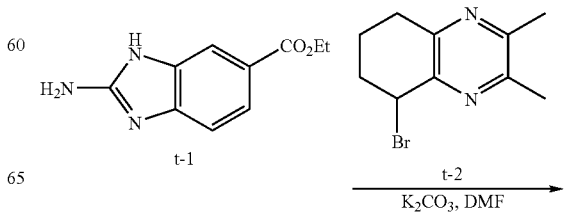

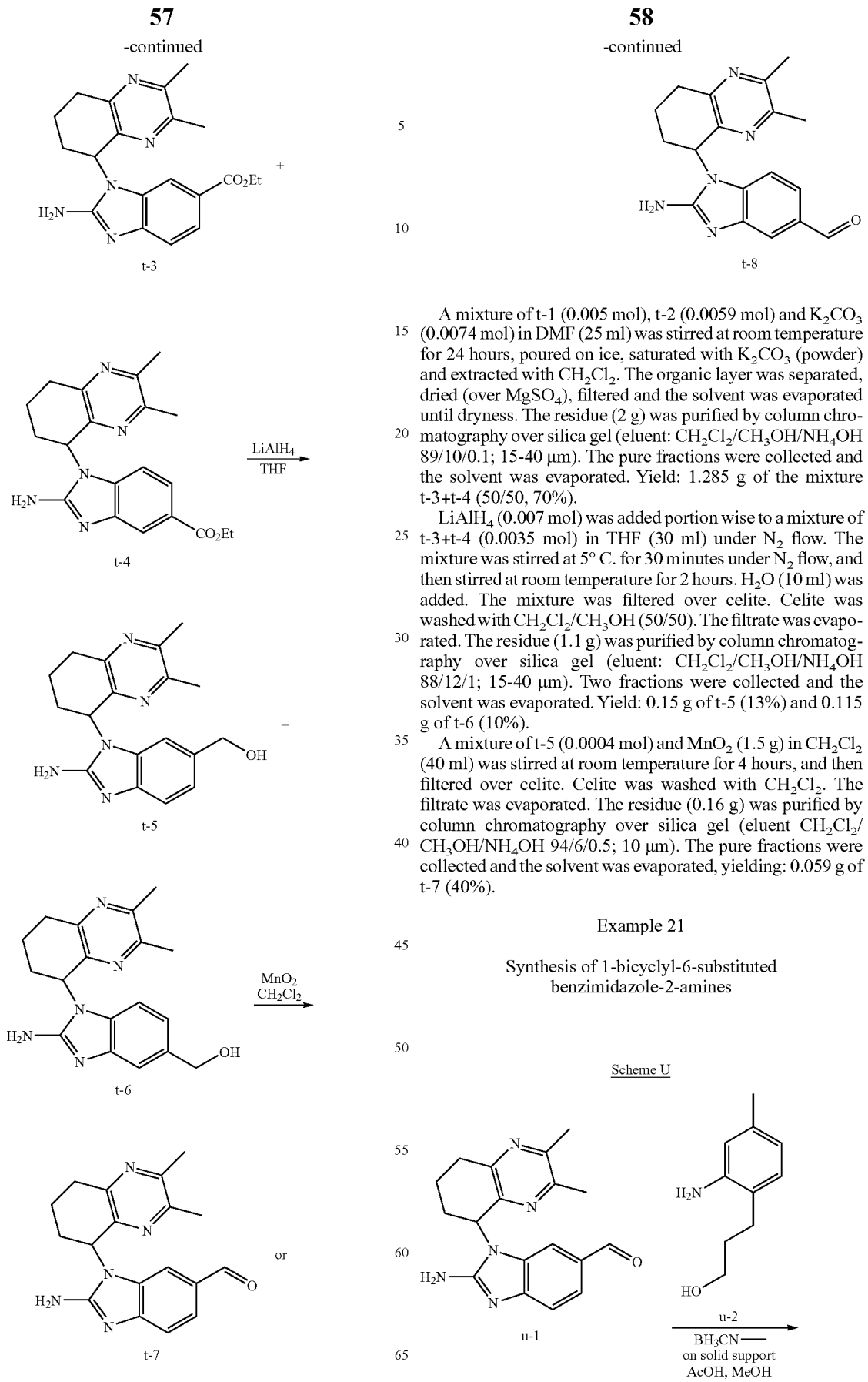

A mixture of t-1 (0.005 mol), t-2 (0.0059 mol) and $K_2CO_3$ (0.0074 mol) in DMF (25 ml) was stirred at room temperature for 24 hours, poured on ice, saturated with $K_2CO_3$ (powder) and extracted with $CH_2Cl_2$. The organic layer was separated, dried (over $MgSO_4$), filtered and the solvent was evaporated until dryness. The residue (2 g) was purified by column chromatography over silica gel (eluent: $CH_2Cl_2/CH_3OH/NH_4OH$ 89/10/0.1; 15-40 μm). The pure fractions were collected and the solvent was evaporated. Yield: 1.285 g of the mixture t-3+t-4 (50/50, 70%).

$LiAlH_4$ (0.007 mol) was added portion wise to a mixture of t-3+t-4 (0.0035 mol) in THF (30 ml) under $N_2$ flow. The mixture was stirred at 5° C. for 30 minutes under $N_2$ flow, and then stirred at room temperature for 2 hours. $H_2O$ (10 ml) was added. The mixture was filtered over celite. Celite was washed with $CH_2Cl_2/CH_3OH$ (50/50). The filtrate was evaporated. The residue (1.1 g) was purified by column chromatography over silica gel (eluent: $CH_2Cl_2/CH_3OH/NH_4OH$ 88/12/1; 15-40 μm). Two fractions were collected and the solvent was evaporated. Yield: 0.15 g of t-5 (13%) and 0.115 g of t-6 (10%).

A mixture of t-5 (0.0004 mol) and $MnO_2$ (1.5 g) in $CH_2Cl_2$ (40 ml) was stirred at room temperature for 4 hours, and then filtered over celite. Celite was washed with $CH_2Cl_2$. The filtrate was evaporated. The residue (0.16 g) was purified by column chromatography over silica gel (eluent $CH_2Cl_2/CH_3OH/NH_4OH$ 94/6/0.5; 10 μm). The pure fractions were collected and the solvent was evaporated, yielding: 0.059 g of t-7 (40%).

Example 21

Synthesis of 1-bicyclyl-6-substituted benzimidazole-2-amines

Scheme U

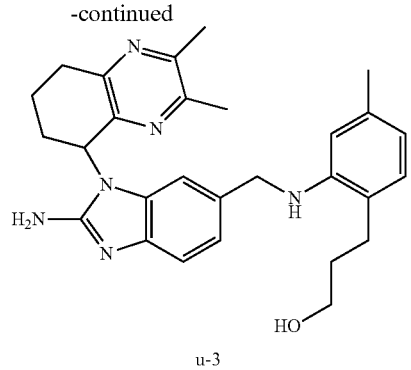

u-3

A mixture of u-1 (0.0001 mol), u-2 (0.0002 mol), BH$_3$CN— on solid support (0.0002 mol) and CH$_3$CO$_2$H (3 drops) in CH$_3$OH (10 ml) was stirred at room temperature for 12 hours. The solvent was evaporated until dryness. The residue was taken up in CH$_2$Cl$_2$/CH$_3$OH. The mixture was basified with K$_2$CO$_3$ 10%, saturated with K$_2$CO$_3$ (powder) and extracted with CH$_2$Cl$_2$. The organic layer was separated, dried (over MgSO$_4$), filtered and the solvent was evaporated until dryness. The residue was crystallized from 2-propanone/Diisopropylether. The precipitate was filtered off and dried, yielding: 0.042 g of u-3 (49%, compound 206, melting point: 165° C.).

Example 22

Synthesis of 1-[(4-benzimidazolyl)methyl-5-formyl-benzimidazole-2-amines

Scheme V

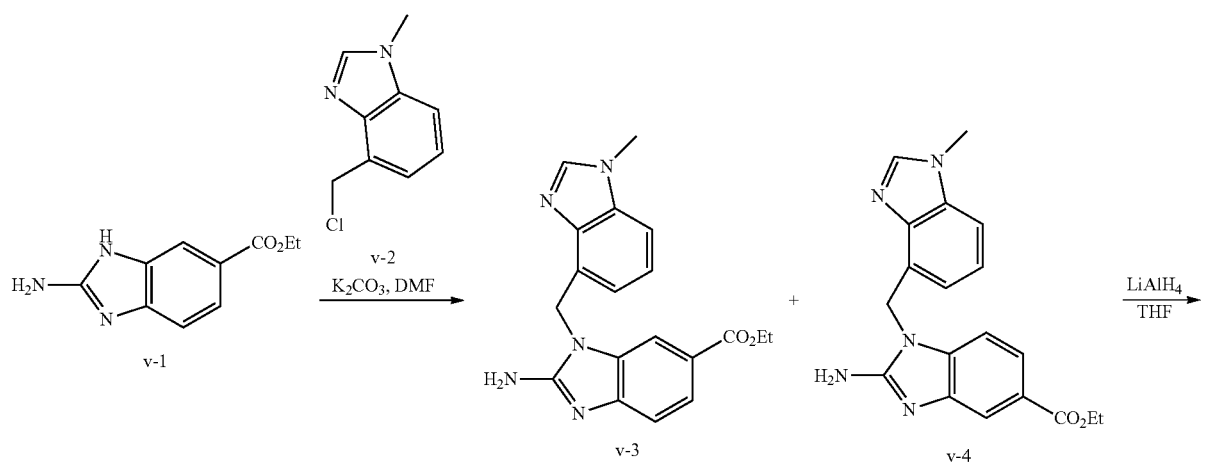

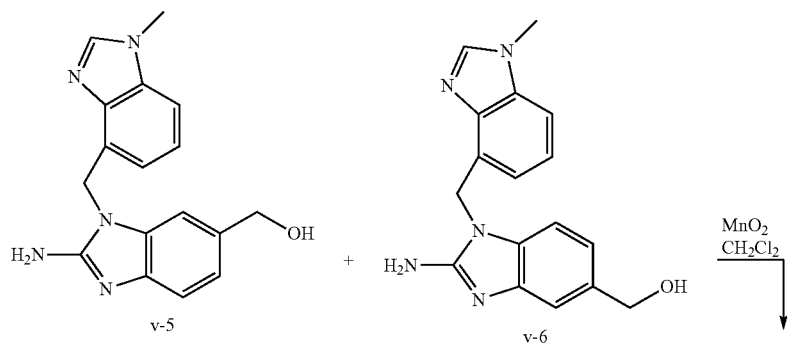

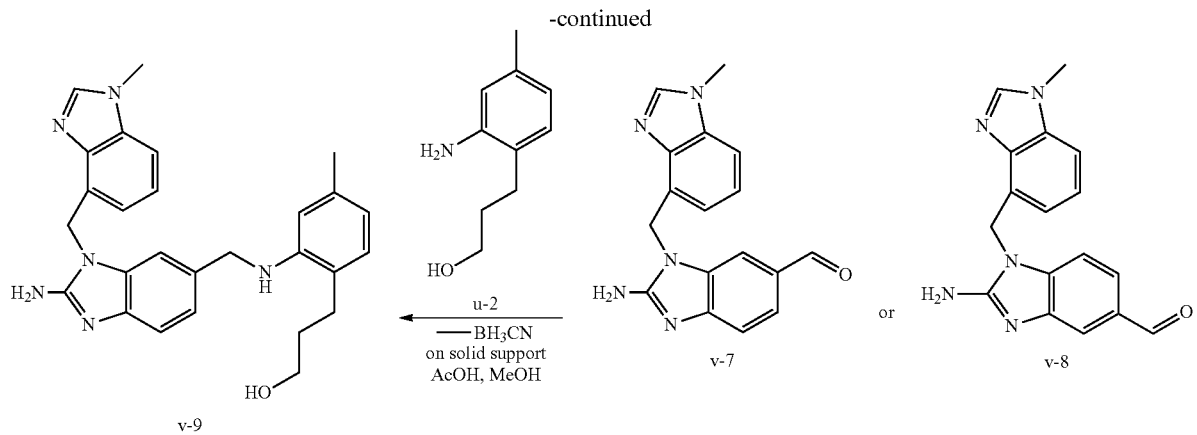

The mixture of intermediates v-3+v-4 (50/50, 93%, melting point: 144° C.) was synthesized according to the procedure described for the mixture of intermediates t-3+t-4.

Compounds v-5 (33%, compound 223, melting point 258° C.) and v-6 (35%, melting point 260° C.) were synthesized according to the procedure described for intermediates t-5 and t-6.

Compound v-7 (81%) was synthesized according to the procedure described for intermediate t-7.

Final compound v-9 (28%, compound 211, melting point: 174° C.) was synthesized according to the procedure described for final compound u-3.

Example 23

Synthesis of 1-quinolonylmethyl-benzimidazole-2-amines

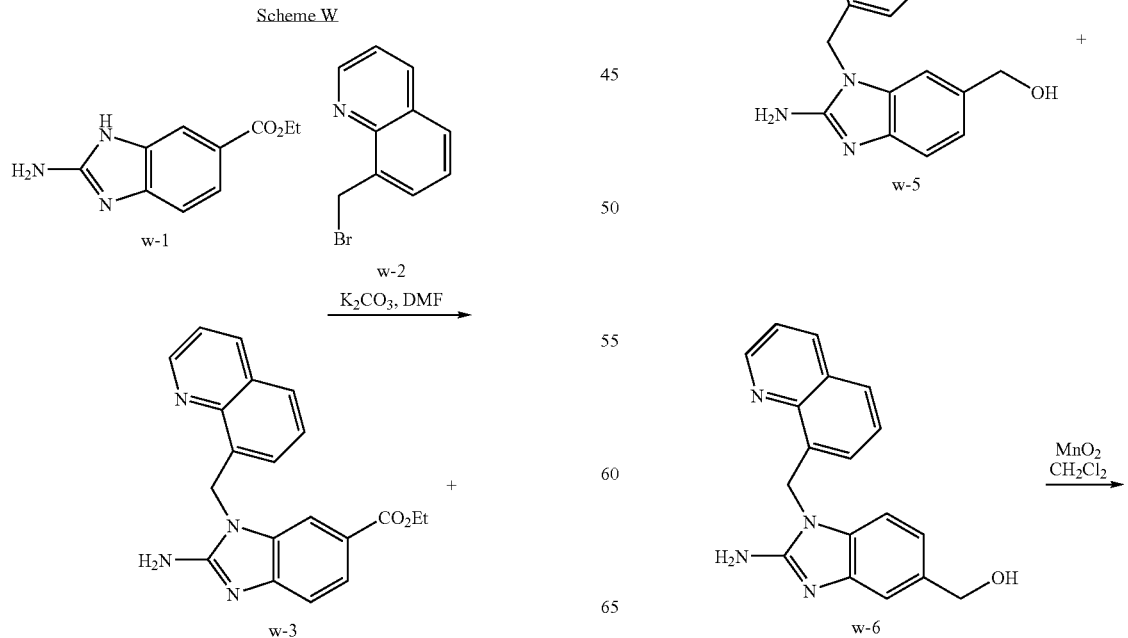

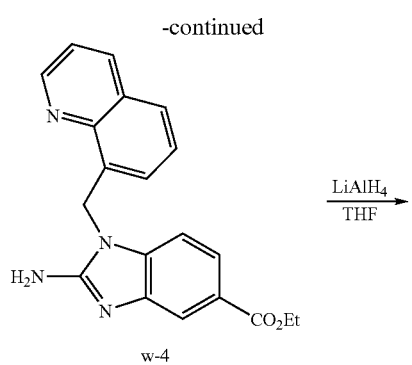

-continued

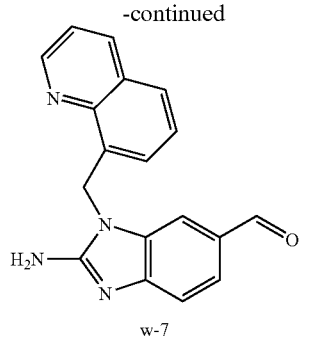

w-7 or

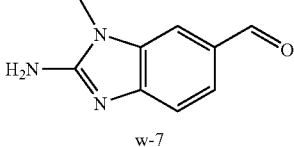

w-8

Intermediate w-2 is identical to intermediate q-2.

The mixture of intermediates w-3+w-4 (50/50, 32%) was synthesized according to the procedure described for the mixture of intermediates t-3+t-4.

Intermediates w-5 (18%, melting point 230° C.) and w-6 (10%, melting point: >260° C.) have been synthesized according to the procedure described for intermediates t-5 and t-6.

Intermediate w-7 (81%) was synthesized according to the procedure described for intermediate t-7.

Example 24

Synthesis of 1-quinolonylmethyl-6-phenylaminomethyl-benzimidazole-2-amines

Scheme X

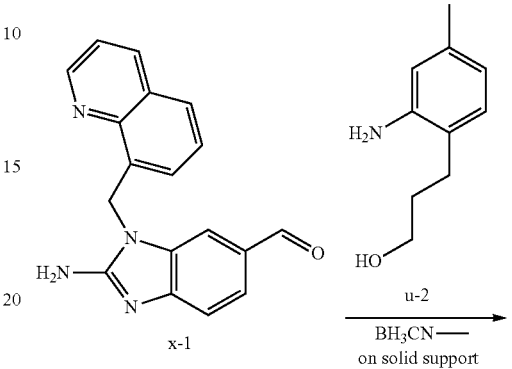

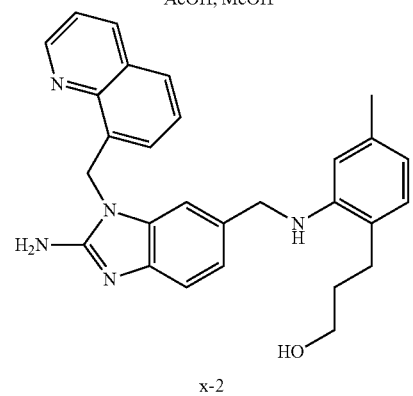

x-2

Final compound x-2 (26%, compound 214, melting point: 194° C.) was synthesized according to the procedure described for final compounds u-3.

Example 25

Synthesis of 1-pyridylmethyl-6-phenylaminomethyl-benzimidazole-2-amines

Scheme Y

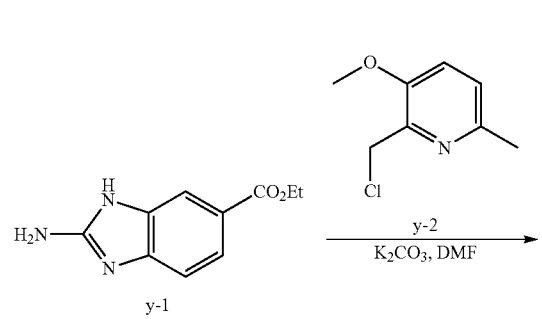

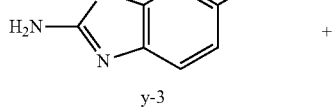

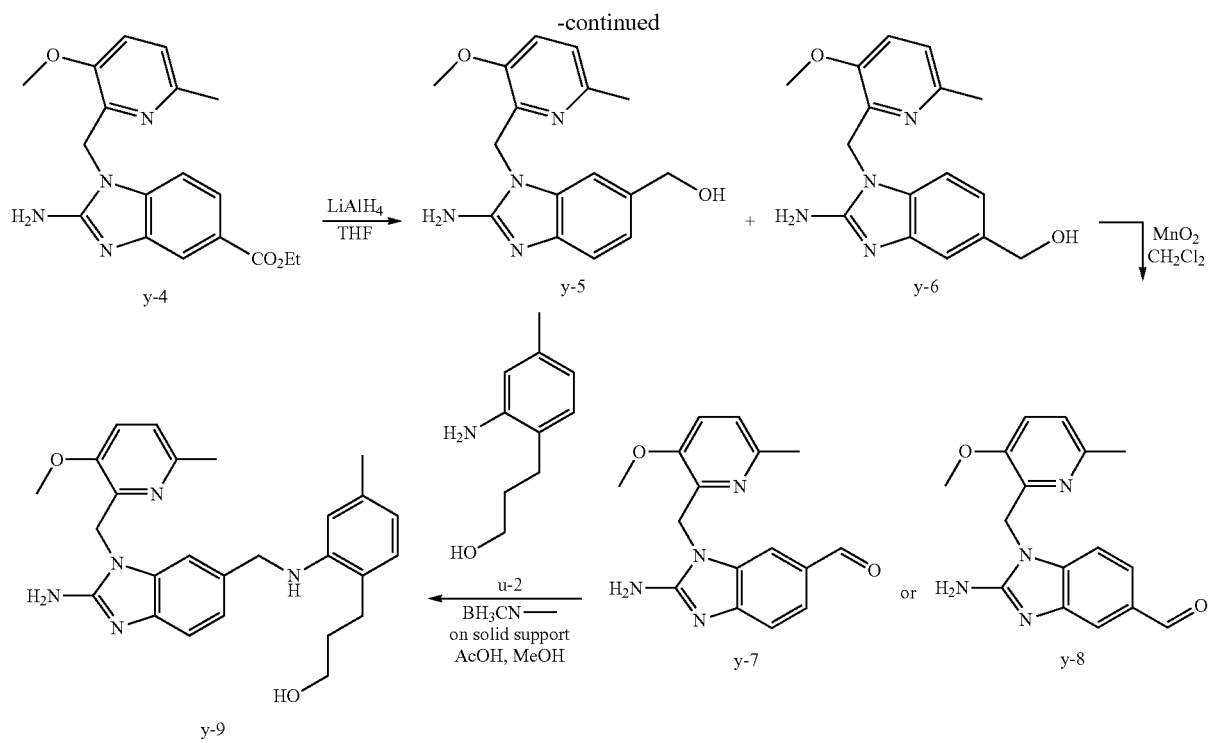

The mixture of intermediates y-3 and y-4 (50/50, 57%) was synthesized according to the procedure described for the mixture of intermediates t-3 and t-4.

Intermediates y-5 (12%) and y-6 (9%) were synthesized according to the procedure described for intermediates t-5 and t-6.

Intermediate y-7 (91%) was synthesized according to the procedure described for intermediate t-7.

Final compound y-9 (30%, compound 209, melting point: 212° C.) was synthesized according to the procedure described for final compounds u-3.

Example 26

Synthesis of (6-bromo-1-pyridyl)methyl 5- and 6-aminomethylbenzimidazole-2-amines Scheme Z

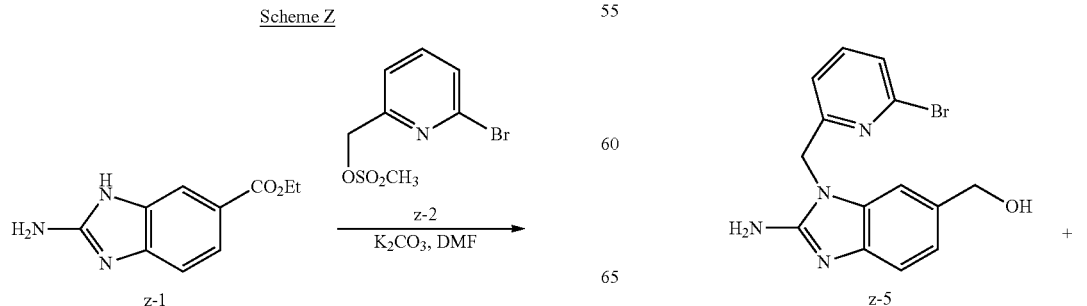

-continued

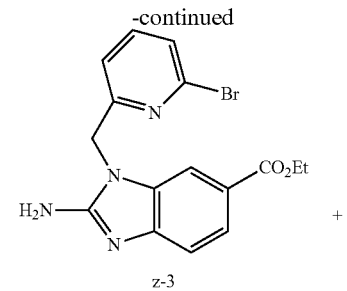

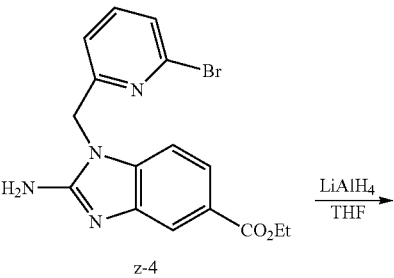

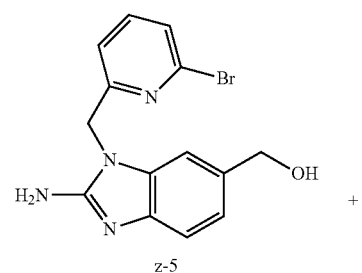

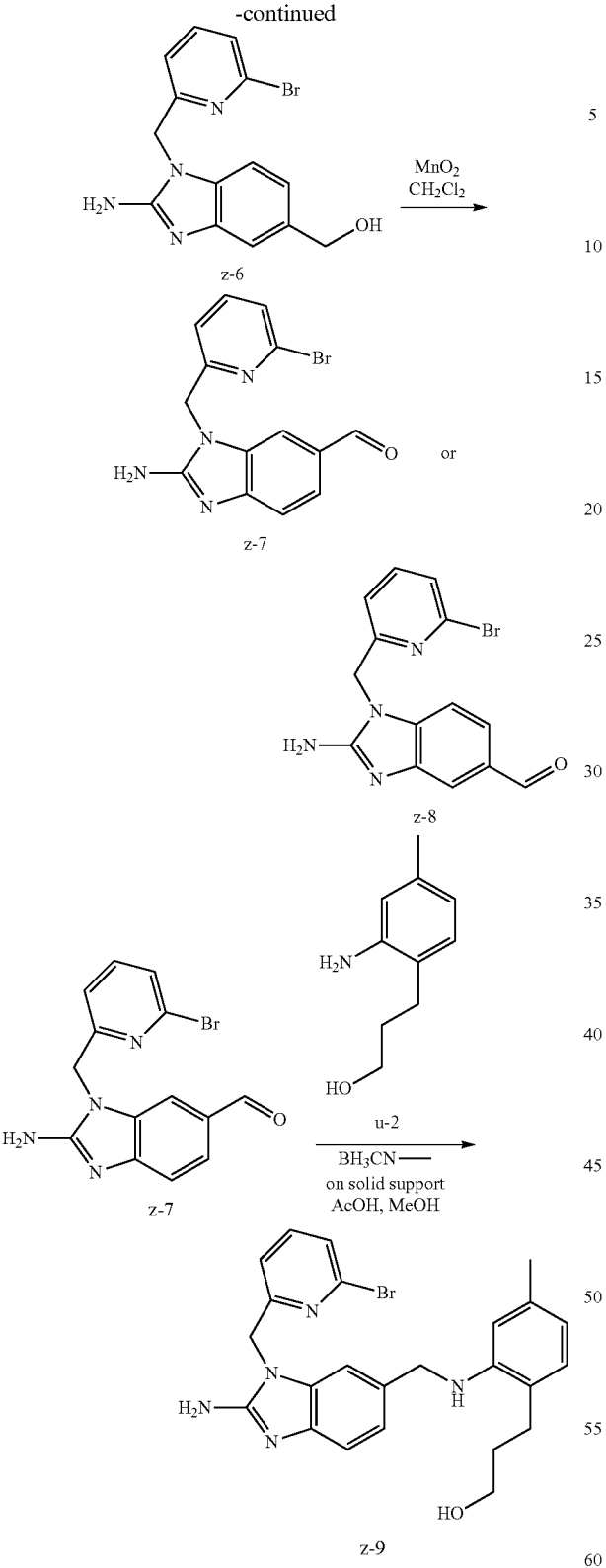

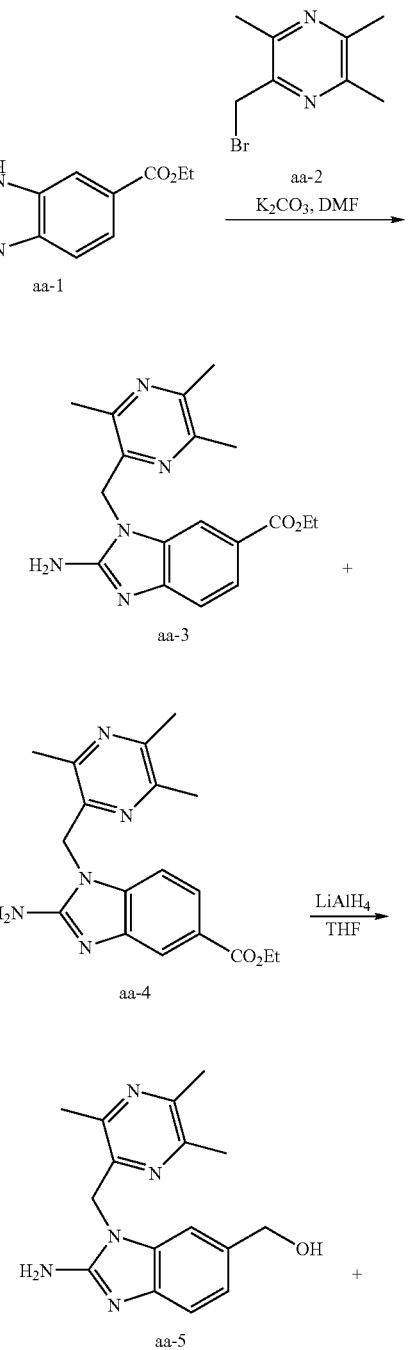

C.) have been synthesized according to the procedure described for intermediates t-5 and t-6.

Intermediate z-7 (80%) was synthesized according to the procedure described for intermediate t-7.

Final compound z-10 (48%, compound 212, melting point: 158° C.) was synthesized according to the procedure described for final compounds u-3.

Example 27

Scheme AA

The mixture of intermediates z-3+z-4 (50/50, 40%) was synthesized according to the procedure described for the mixture of intermediates t-3+t-4.

Intermediates z-5 (18%, compound 226, melting point 221° C.) and z-6 (16%, compound 227, melting point: 230°

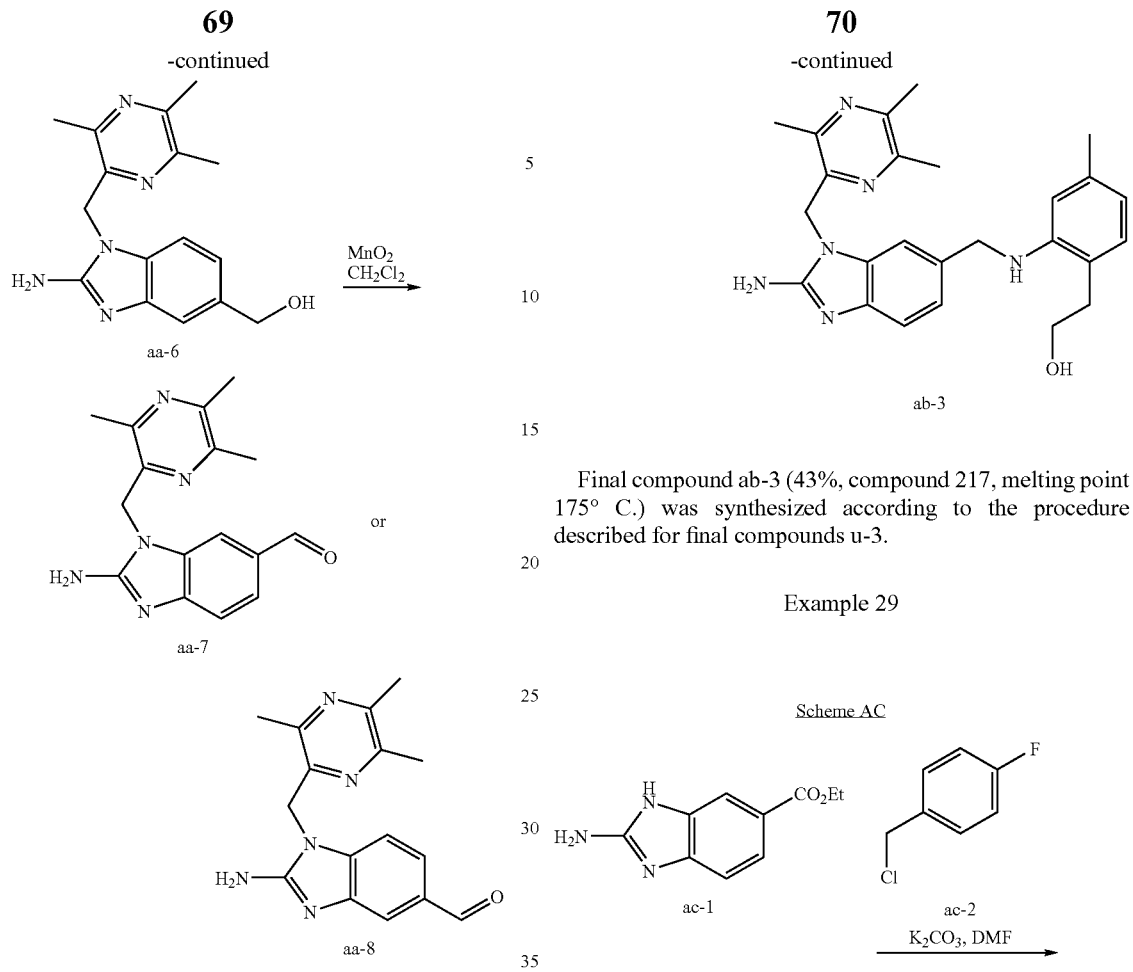

The mixture of intermediates aa-3+aa-4 (50/50, 35%) was synthesized according to the procedure described for the mixture of intermediates t-3+t-4.

Intermediates aa-5 (24%) and aa-6 (18%) have been synthesized according to the procedure described for intermediates t-5 and t-6.

Intermediate aa-7 (100%) was synthesized according to the procedure described for intermediate t-7.

Example 28

Scheme AB

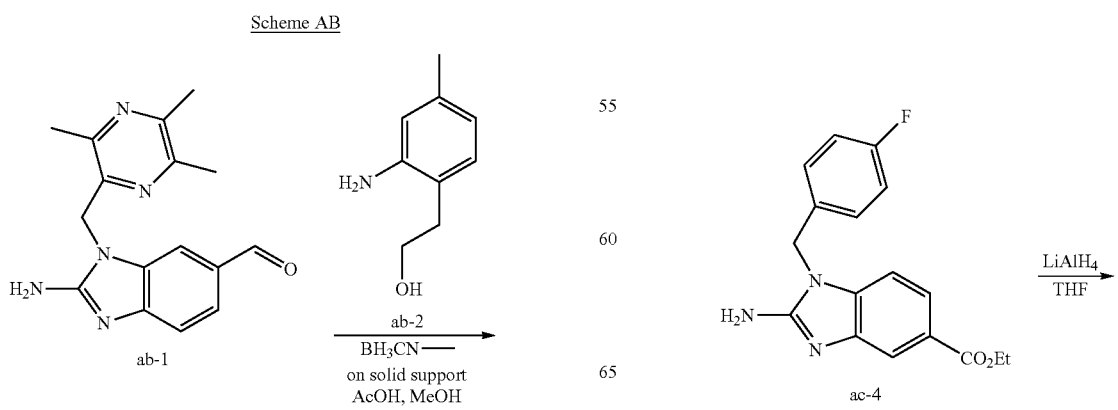

Final compound ab-3 (43%, compound 217, melting point 175° C.) was synthesized according to the procedure described for final compounds u-3.

Example 29

-continued

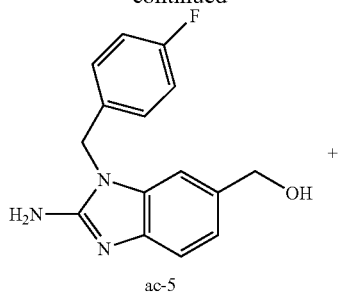
ac-5

+

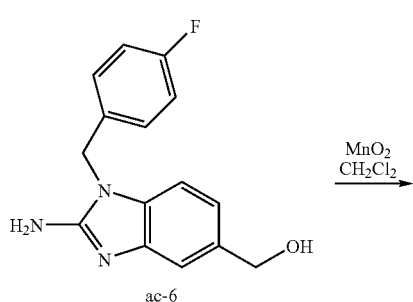
ac-6

MnO₂
CH₂Cl₂ →

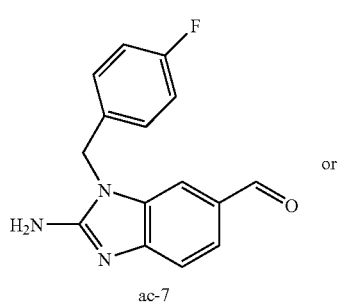
ac-7 or

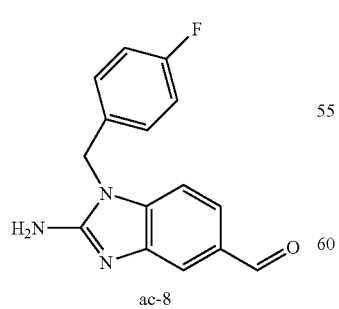
ac-8

The mixture of intermediates ac-3+ac-4 (50/50, 46%, melting point 193° C.) was synthesized according to the procedure described for the mixture of intermediates t-3+t-4.

Intermediates ac-5 (33%, compound 236, melting point 202° C.) and ac-6 (21%, compound 237, melting point >260° C.) have been synthesized according to the procedure described for intermediates t-5 and t-6.

Intermediate ac-7 (100%) was synthesized according to the procedure described for intermediate t-7.

Example 30

Scheme AD

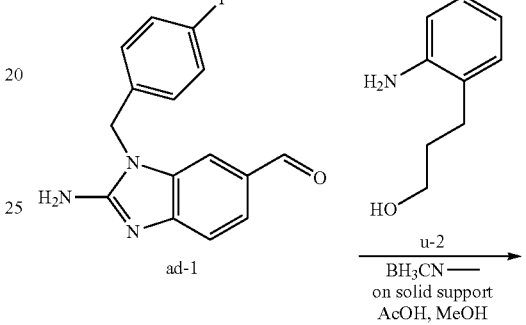
ad-1        u-2
BH₃CN
on solid support
AcOH, MeOH →

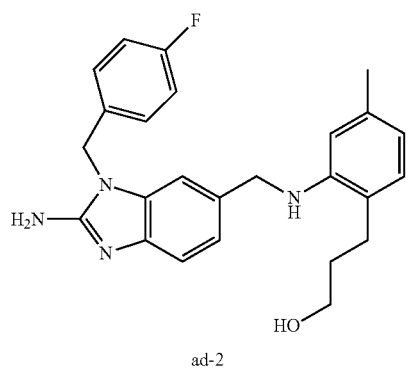
ad-2

Final compound ad-2 (46%, compound 219, melting point: 179° C.) was synthesized according to the procedure described for final compounds o-5.

The compounds listed in the following tables were prepared analogous to one of the above exemplified synthesis schemes. The tables include physicochemical data such as mass spectral data (MH+) and/or melting point. Any radical depicted in these tables is connected to the remainder of the molecule by the 'open' bond, i.e. that bond that at one side has no radical).

TABLE 1

| Comp. No. | R | Activity | MH+ | Melting point | Salt form | Synthesis scheme |
|---|---|---|---|---|---|---|
| 1 | 3-methylphenyl | 8.6 | 374 | 234° C. | | A |
| 2 | 3,5-dichlorophenyl | 8.6 | 428 | 250° C. | | A |
| 3 | 3-bromophenyl | 8.6 | 438 | | | A |
| 4 | 3-(trifluoromethoxy)phenyl | 8.6 | 444 | 156° C. | | A |
| 5 | 3-chlorophenyl | 8.5 | 394 | | | A |
| 6 | 3-ethynylphenyl | 8.5 | 384 | 200° C. | | A |
| 7 | 2-methoxyphenyl | 8.5 | 390 | 140° C. (gum) | acetate | A |
| 8 | 2-methylphenyl | 8.5 | 374 | 120° C. (gum) | acetate | A |

TABLE 1-continued
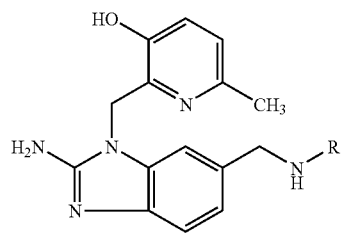
| Comp. No. | R | Activity | MH+ | Melting point | Salt form | Synthesis scheme |
|---|---|---|---|---|---|---|
| 9 | 3,5-dimethylphenyl | 8.4 | 388 | 228° C. | | A |
| 10 | 4-methylphenylsulfonamide | 8.4 | 439 | 188° C. | | A |
| 11 | 2-(hydroxymethyl)phenyl | 8.4 | 390 | 212° C. | | A |
| 12 | 2-ethylphenyl | 8.4 | 388 | 130° C. (gum) | acetate | A |
| 13 | 4-cyanophenyl | 8.4 | 385 | | | A |
| 14 | ethyl 3-hydroxy-4-methylbenzoate | 8.3 | 448 | 252° C. | | A |
| 15 | 3-methyl(methylthio)phenyl | 8.3 | 406 | 188° C. | | A |
| 16 | 2-ethyl-6-methylphenyl | 8.3 | 402 | | | A |

TABLE 1-continued
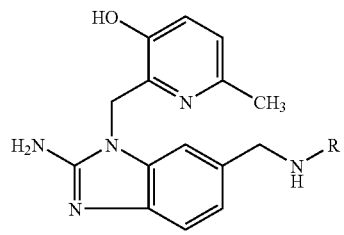
| Comp. No. | R | Activity | MH+ | Melting point | Salt form | Synthesis scheme |
|---|---|---|---|---|---|---|
| 17 | 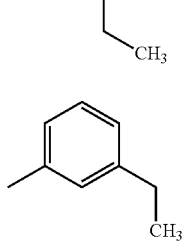 | 8.1 | 416 | | | A |
| 18 | 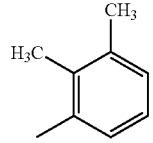 | 8.0 | 388 | | | A |
| 19 | 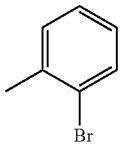 | 8.0 | 388 | | | A |
| 20 | 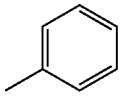 | 8.0 | 438 | | | A |
| 21 | 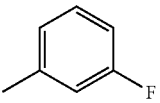 | 7.9 | 360 | >250° C. | | A |
| 22 | 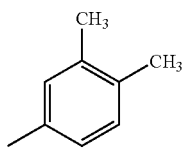 | 7.9 | 378 | | | A |
| 23 | 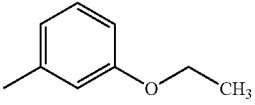 | 7.9 | 388 | | | A |
| 24 |  | 7.9 | 404 | | | A |

TABLE 1-continued
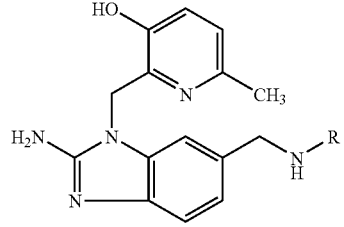
| Comp. No. | R | Activity | MH+ | Melting point | Salt form | Synthesis scheme |
|---|---|---|---|---|---|---|
| 25 | 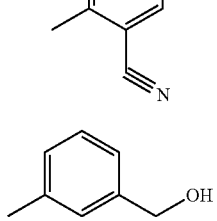 | 7.9 | 385 | | | A |
| 26 | 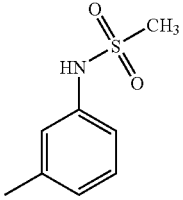 | 7.9 | 390 | | | A |
| 27 | 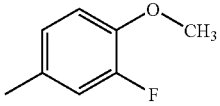 | 7.9 | 453 | | | A |
| 28 | 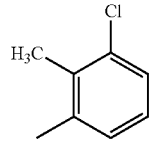 | 7.8 | 408 | | | A |
| 29 | 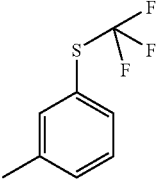 | 7.8 | 408 | | | A |
| 30 | 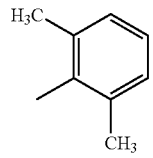 | 7.8 | 460 | | | A |
| 31 | 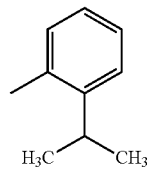 | 7.8 | 388 | | | A |
| 32 |  | 7.8 | 402 | | | A |

TABLE 1-continued
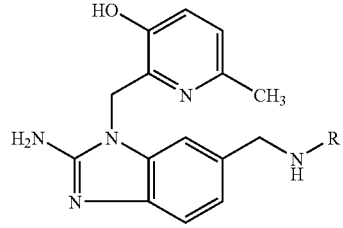
| Comp. No. | R | Activity | MH+ | Melting point | Salt form | Synthesis scheme |
|---|---|---|---|---|---|---|
| 33 | 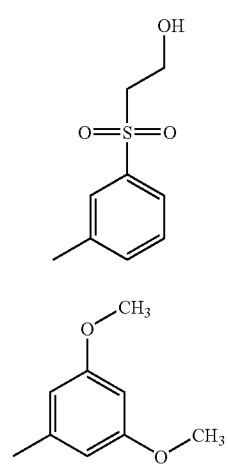 | 7.8 | 468 | | | A |
| 34 | 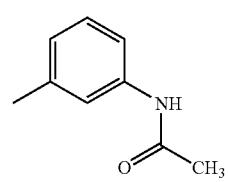 | 7.7 | 420 | | | A |
| 35 | 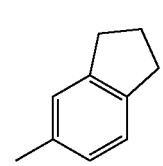 | 7.7 | 417 | | | A |
| 36 | 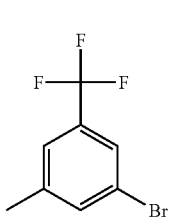 | 7.7 | 400 | | | A |
| 37 | 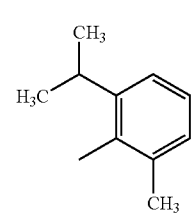 | 7.7 | 506 | | | A |
| 38 |  | 7.7 | 416 | | | A |

TABLE 1-continued

| Comp. No. | R | Activity | MH+ | Melting point | Salt form | Synthesis scheme |
|---|---|---|---|---|---|---|
| 39 | 2-methyl-benzamide | 7.7 | 403 | | | A |
| 40 | 2-fluoro-6-methylphenyl | 7.7 | 378 | | | A |
| 41 | 3-methyl-benzamidine | 7.7 | 402 | | | A |
| 42 | 3-methyl-acetophenone | 7.6 | 402 | | | A |
| 43 | 6-methyl-2,3-dihydro-1,4-benzodioxine | 7.6 | 418 | | | A |
| 44 | 8-methylquinoline | 7.6 | 411 | | | A |
| 45 | 3-fluoro-5-(trifluoromethyl)phenyl | 7.6 | 446 | | | A |

TABLE 1-continued

| Comp. No. | R | Activity | MH+ | Melting point | Salt form | Synthesis scheme |
|---|---|---|---|---|---|---|
| 46 | 3-methylphenylacetic acid | 7.6 | 418 | | | A |
| 47 | 3-methyl-N-butylbenzenesulfonamide | 7.6 | 495 | | | A |
| 48 | 2-methyl-(trifluoromethyl)benzene | 7.6 | 428 | | | A |
| 49 | 3,5-difluorotoluene | 7.5 | 396 | | | A |
| 50 | 5-bromo-2,3-dimethylbenzene | 7.5 | 452 | | | A |
| 51 | methyl 5-bromo-2-methylbenzoate | 7.5 | 496 | | | A |
| 52 | 5-bromo-2-methyl-3-ethylbenzene | 7.5 | 466 | | | A |

TABLE 1-continued
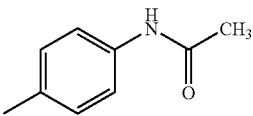
| Comp. No. | R | Activity | MH+ | Melting point | Salt form | Synthesis scheme |
|---|---|---|---|---|---|---|
| 53 | 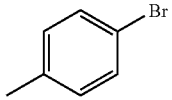 | 7.5 | 417 | | | A |
| 54 | 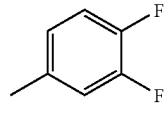 | 7.5 | 438 | | | A |
| 55 | 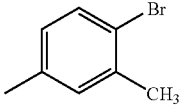 | 7.4 | 396 | | | A |
| 56 | 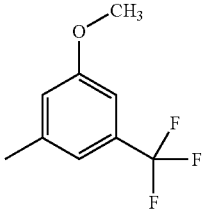 | 7.4 | 452 | | | A |
| 57 | 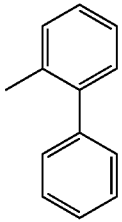 | 7.4 | 458 | | | A |
| 58 | 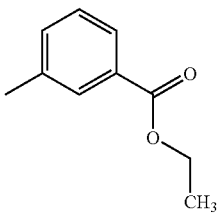 | 7.4 | 436 | 100° C. (gum) | acetate | A |
| 59 |  | 7.3 | 432 | | | A |

TABLE 1-continued
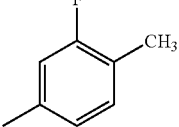
| Comp. No. | R | Activity | MH+ | Melting point | Salt form | Synthesis scheme |
|---|---|---|---|---|---|---|
| 60 | 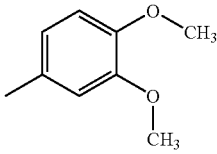 | 7.3 | 392 | | | A |
| 61 | 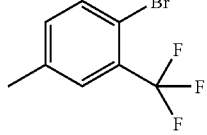 | 7.3 | 420 | | | A |
| 62 | 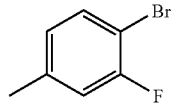 | 7.3 | 506 | | | A |
| 63 | 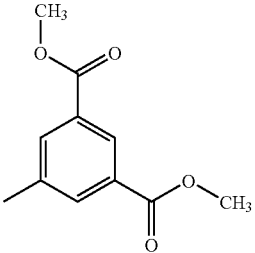 | 7.3 | 456 | | | A |
| 64 | 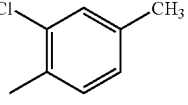 | 7.3 | 476 | | | A |
| 65 | 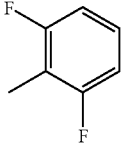 | 7.3 | 408 | | | A |
| 66 | 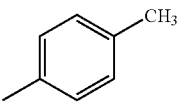 | 7.3 | 396 | | | A |
| 67 |  | 7.3 | 374 | | | A |

TABLE 1-continued

| Comp. No. | R | Activity | MH+ | Melting point | Salt form | Synthesis scheme |
|---|---|---|---|---|---|---|
| 68 | (2-methyl, ethyl ester phenyl) | 7.2 | 432 | | | A |
| 69 | (2-methyl, acetyl phenyl) | 7.2 | 402 | | | A |
| 70 | (2-methyl, tert-butyl phenyl) | 7.2 | 416 | | | A |
| 71 | (3-methyl, phenoxy phenyl) | 7.1 | 452 | | | A |
| 72 | (2,6-dichloro, 4-methyl, hydroxy phenyl) | 7.1 | 444 | | | A |
| 73 | (3-ethyl, methyl phenyl) | 7.1 | 388 | 182° C. | | A |

TABLE 1-continued
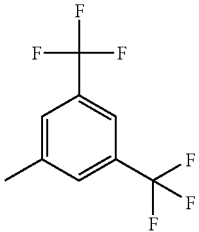
| Comp. No. | R | Activity | MH+ | Melting point | Salt form | Synthesis scheme |
|---|---|---|---|---|---|---|
| 74 | 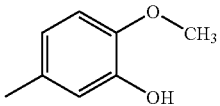 | 7.1 | 496 | | | A |
| 75 | 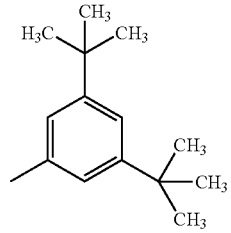 | 7 | 406 | | | A |
| 76 | 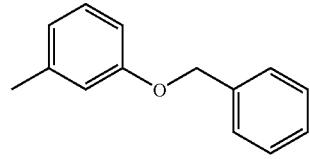 | 6.8 | 472 | | | A |
| 77 | 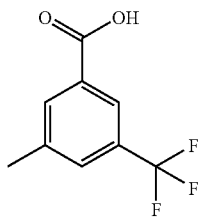 | 6.8 | 466 | | | A |
| 78 | 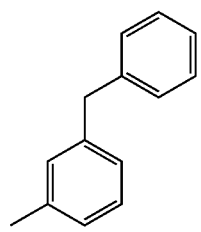 | 6.6 | 472 | | | A |
| 79 |  | 6.4 | 450 | | | A |

TABLE 1-continued
| Comp. No. | R | Activity | MH+ | Melting point | Salt form | Synthesis scheme |
|---|---|---|---|---|---|---|
| 80 | 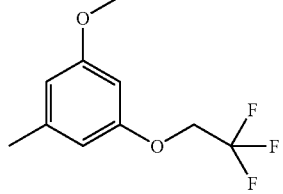 | 6.2 | 556 | | | A |
| 81 | 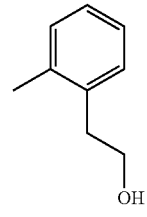 | 9.4 | 404 | 155° C. | | A |
| 82 | 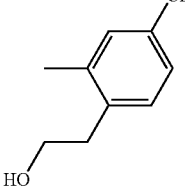 | 10.3 | 418 | 245° C. | | F |
| 83 | 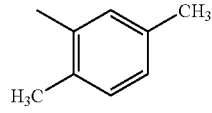 | 9.1 | 388 | 213° C. | | A |
| 84 | 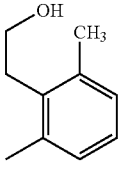 | 9 | 418 | 323° C. | | A |
| 85 | 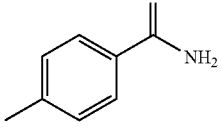 | 8.4 | 403 | 204° C. | | A |

TABLE 1-continued

| Comp. No. | R | Activity | MH+ | Melting point | Salt form | Synthesis scheme |
|---|---|---|---|---|---|---|
| 86 | 2-methyl-5-(hydroxymethyl)phenyl (2,5-substituted, CH₃ and CH₂OH) | 8.4 | 404 | 252° C. | | A |
| 87 | 2,6-dimethyl-hydroxymethylphenyl | 8.2 | 404 | 170° C. | | A |
| 88 | 2,3-dimethyl-hydroxymethylphenyl | 7.8 | 404 | 172° C. | | A |
| 89 | 4-cyano-3-methylphenyl-(CH₂)₂-OH | 10.6 | 429 | 240° C. | | F |
| 90 | 2,4-dimethylphenyl-(CH₂)₃-OH | 10.5 | 432 | 248° C. | | E |
| 91 | 2,4-dimethylphenyl-O-(CH₂)₂-OH | 10.5 | 434 | | | A |

TABLE 1-continued

| Comp. No. | R | Activity | MH+ | Melting point | Salt form | Synthesis scheme |
|---|---|---|---|---|---|---|
| 92 | 4-ethynyl-2-methylphenyl-(CH₂)₂-OH | 10.4 | 428 | 252° C. | | G |
| 93 | 4-bromo-2-methylphenyl-(CH₂)₂-OH | 10 | 482 | | | F |
| 94 | 4-methyl-2-methylphenyl-(CH₂)₂-OH | 10 | 432 | 207° C. | | F |
| 95 | 4-chloro-2-methylphenyl-(CH₂)₃-OH | 10 | 452-454 | 231° C. | | A |
| 96 | 4-methoxy-2-methylphenyl-(CH₂)₃-OH | 9.9 | 448 | 226° C. | | E |
| 97 | 4-methoxy-2-methylphenyl-(CH₂)₂-OH | 9.8 | 434 | | | F |

TABLE 1-continued
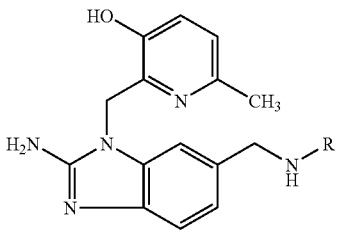
| Comp. No. | R | Activity | MH+ | Melting point | Salt form | Synthesis scheme |
|---|---|---|---|---|---|---|
| 98 | 2-methylphenyl-(CH$_2$)$_3$-OH | 9.6 | 418 | 126° C. | | E |
| 99 | 4-CF$_3$-2-methylphenyl-(CH$_2$)$_3$-OH | 9.6 | 486 | 205° C. | | E |
| 100 | 2,4-dimethylphenyl-SO$_2$-(CH$_2$)$_2$-OH | 9.6 | 482 | >260° C. | | H |
| 101 | 3,4-dimethylphenyl-(CH$_2$)$_4$-OH | 9.5 | 446 | 228° C. | | E |
| 102 | 4-F-2-methylphenyl-(CH$_2$)$_2$-OH | 9.4 | 422 | | | F |
| 103 | 4-isopropyl-2-methylphenyl-(CH$_2$)$_2$-OH | 9.3 | 446 | 198° C. | | F |

TABLE 1-continued
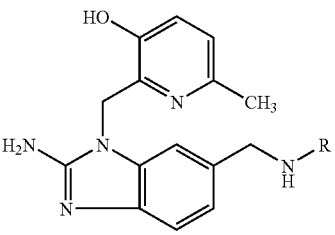
| Comp. No. | R | Activity | MH+ | Melting point | Salt form | Synthesis scheme |
|---|---|---|---|---|---|---|
| 104 | 4-CH3-C6H4-CH=CH-CH2-OH | 9.3 | 430 | 246° C. | | A |
| 105 | 2-CH3-4-CH3-C6H3-NH-(CH2)2-OH | 9.2 | 433 | | | A |
| 106 | 2-CH3-C6H4-(CH2)2-CONH2 | 8.5 | 431 | 220° C. | | A |
| 107 | 3-CH3-4-(CH2)2OH-C6H3-SO2-CH3 | 8.4 | 482 | | | F |
| 108 | 2-CH3-C6H4-(CH2)2-morpholine | 8 | 473 | 148° C. | | A |
| 109 | 3-CH3-4-(CH2)2OH-C6H3-CO-NH2 | 8 | 447 | | | F |

TABLE 1-continued
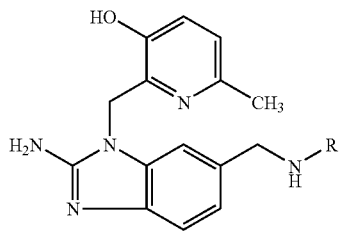
| Comp. No. | R | Activity | MH+ | Melting point | Salt form | Synthesis scheme |
|---|---|---|---|---|---|---|
| 110 | 3-methylphenyl-(CH₂)₂—OH | 7.8 | 404 | >250° C. | HCl | A |
| 111 | 2,4-dimethylphenyl-CH₂CH₂CH(OH)CH₃ | 9.3 | 446 | 241° C. | | A |
| 112 | 2,4-dimethylphenyl-CH₂CH₂C(O)NH₂ | 9.4 | 445 | 236° C. | | A |
| 113 | 4-vinyl-2-methylphenyl-CH₂CH₂OH | >9.6 | 430 | 246° C. | | A |
| 114 | 4-trifluoromethyl-2-methylphenyl-CH₂CH₂C(O)NH₂ | 9.2 | 499 | 205° C. | | A |

TABLE 1-continued

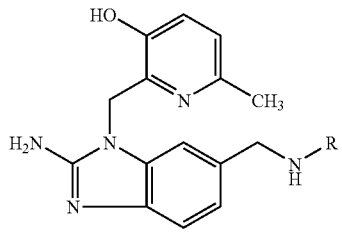

| Comp. No. | R | Activity | MH+ | Melting point | Salt form | Synthesis scheme |
|---|---|---|---|---|---|---|
| 115 | (4-trifluoromethyl-2-methylphenyl ethanol) | >9.6 | 472 | 216° C. | | F |

TABLE 2

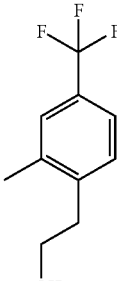

| Comp. No. | R | Activity | MH+ | Melting point (° C.) | sSynthesis scheme |
|---|---|---|---|---|---|
| 116 | phenyl | 7.0 | 360 | | A |
| 117 | 3,5-dimethylphenyl | 6.8 | 388 | | A |
| 118 | 3-acetylphenyl | 6.4 | 402 | | A |
| 119 | 2,3-dimethylphenyl | 6.4 | 388 | | A |

TABLE 2-continued

| Comp. No. | R | Activity | MH+ | Melting point (° C.) | sSynthesis scheme |
|---|---|---|---|---|---|
| 120 | 3-methylphenyl | 6.4 | 374 | 212 | A |
| 121 | 3,5-dichlorophenyl | 5.8 | 428 | | A |
| 122 | 3-chlorophenyl | <4.0 | 394 | | A |

TABLE 2-continued

[Structure: 2-amino-benzimidazole with (3-hydroxy-6-methylpyridin-2-yl)methyl group on N1 and CH₂-NH-R at 5-position]

| Comp. No. | R | Activity | MH+ | Melting point (° C.) | sSynthesis scheme |
|---|---|---|---|---|---|
| 123 | 8-methylquinolin-yl | <4.0 | 411 | | A |
| 124 | 3-fluorophenyl | <4.0 | 378 | | A |
| 125 | 3-methylbenzyl (with CH₃) | <4.0 | 388 | | A |
| 126 | 3-bromo-methylphenyl | <4.0 | 438 | 205 | A |
| 127 | 3-methylphenylacetylene | <4.0 | 384 | 205 | A |

Compound Prepared According to Scheme E

[Structure of compound 128]

| Comp. No. | Activity category | MH+ | Melting point (° C.) |
|---|---|---|---|
| 128 | 6.9 | 522 | 129 |

TABLE 3 compounds prepared according to scheme B

[Structure: 2-amino-benzimidazole with (3-hydroxy-6-methylpyridin-2-yl)methyl on N1 and CH₂-N(R¹)(R²) at 6-position]

| Comp. No. | R¹ | R² | Activity | MH+ | Melting point (° C.) | Salt |
|---|---|---|---|---|---|---|
| 129 | 3-methylbenzyl (CH₃) | propanol (—CH₂CH₂CH₂OH) | 9.3 | 418 | 210 | |

TABLE 3-continued compounds prepared according to scheme B

[Structure: benzimidazole core with 2-amino, N1 substituted with CH2-(3-hydroxy-6-methylpyridin-2-yl), and 6-CH2-NR1R2 group]

| Comp. No. | R¹ | R² | Activity | MH+ | Melting point (° C.) | Salt |
|---|---|---|---|---|---|---|
| 130 | phenyl | propyl-OH | 8.6 | 404 | 175 | |
| 131 | 3-methylphenyl | propyl-NH₂ | 8.4 | 417 | 200 (gum) | HCl |
| 132 | benzyl (CH₂-phenyl) | propyl-N(CH₃)₂ | 7.9 | 445 | 190 | |
| 133 | phenyl | CH₂CH₂-phenyl | 7.5 | 450 | 220 | |
| 134 | 3-methylphenyl | butyl-OH | 9.2 | 432 | 90 (gum) | |
| 135 | benzyl (CH₂-phenyl) | propyl-OH | 7.7 | 418 | 158 | |
| 136 | 3-methylphenyl | propyl-morpholine | 8.6 | 487 | 245 | |
| 137 | 3-bromophenyl | propanamide (CH₂CH₂C(O)NH₂) | 9.6 | 509 | 245 | |
| 138 | 3-methylphenyl | pentanamide (CH₂CH₂CH₂C(O)NH₂) | 9.4 | 459 | 180 (gum) | HCl |
| 139 | 3-bromophenyl | pentyl-OH | 9.4 | 510 | 120 (gum) | |

TABLE 3-continued
compounds prepared according to scheme B
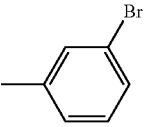
| Comp. No. | R¹ | R² | Activity | MH+ | Melting point (° C.) | Salt |
|---|---|---|---|---|---|---|
| 140 | 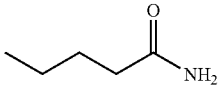 | 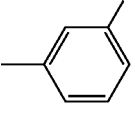 | 9.4 | 523 | 155 | HCl |
| 141 |  | 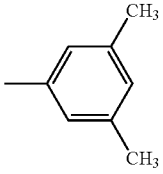 | 9.3 | 482 | 225 | |
| 142 | 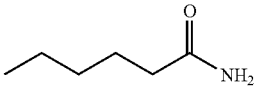 | 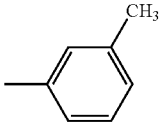 | 9.3 | 487 | 195 | |
| 143 | 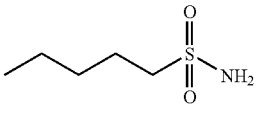 | 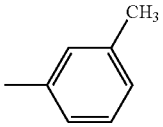 | 9.3 | 509 | 120 (gum) | |
| 144 | 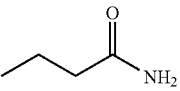 | 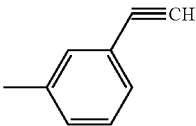 | 9.2 | 445 | 222 | |
| 145 | 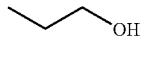 | 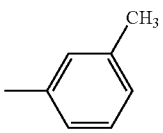 | 9.2 | 428 | 210 | |
| 146 | 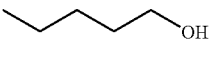 | 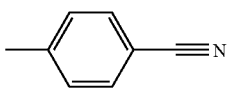 | 9.1 | 446 | 80 (gum) | |
| 147 | 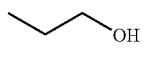 | 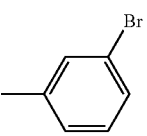 | 9.0 | 429 | >260 | |
| 148 | 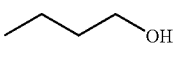 | | 8.7 | 496 | 120 (gum) | |

TABLE 3-continued
compounds prepared according to scheme B
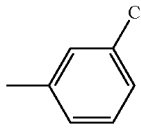
| Comp. No. | R¹ | R² | Activity | MH+ | Melting point (° C.) | Salt |
|---|---|---|---|---|---|---|
| 149 | 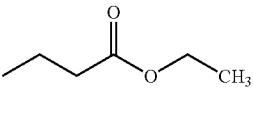 | 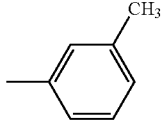 | 8.6 | 474 | 190 | |
| 150 | 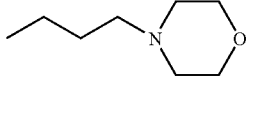 | 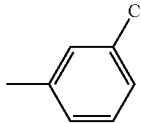 | 8.6 | 501 | 164 | |
| 151 | 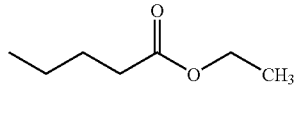 | 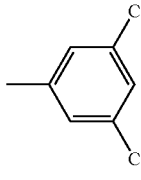 | 8.6 | 488 | 138 | |
| 152 | 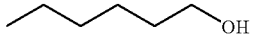 | 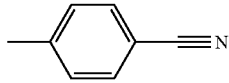 | 8.6 | 474 | 170 | HCl |
| 153 | 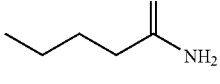 | 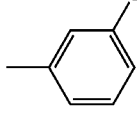 | 8.6 | 470 | 248 | |
| 154 | 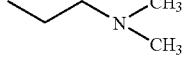 | 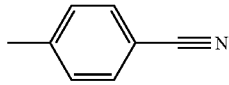 | 8.5 | 445 | 224 | |
| 155 | 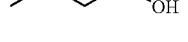 | 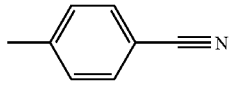 | 8.4 | 443 | 252 | |
| 156 | 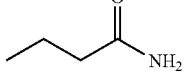 | 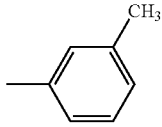 | 8.4 | 456 | >260 | |
| 157 | 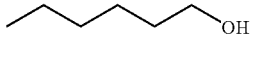 | | 8.3 | 460 | 185 (gum) | HCl |

TABLE 3-continued compounds prepared according to scheme B

| Comp. No. | R¹ | R² | Activity | MH+ | Melting point (° C.) | Salt |
|---|---|---|---|---|---|---|
| 158 | 4-(aminosulfonyl)phenyl-methyl | propanol | 8.3 | 483 | >260 | |
| 159 | 3-fluorophenyl-methyl | propanol | 8.2 | 422 | 165 | |
| 160 | 2-methylphenyl-ethanol | propyl-morpholine | 8.1 | 517 | 184 | |
| 161 | 3-methylphenyl-methyl | butanoic acid | 8.1 | 446 | 165 | |
| 162 | 2-methylphenyl-ethanol | propanol | 8.0 | 448 | 175 | |
| 163 | 4-carbamoylphenyl-methyl | propanol | 7.9 | 447 | 240 | |
| 164 | 2-carbamoylphenyl-methyl | propanol | 7.8 | 447 | 230 | |
| 165 | 2-methylphenyl-methyl | propanol | 7.6 | 418 | 208 | |
| 166 | 2-methylphenyl-ethanol | —CH₃ | 6.8 | 418 | 210 | |

TABLE 3-continued
compounds prepared according to scheme B
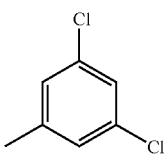
| Comp. No. | R¹ | R² | Activity | MH+ | Melting point (° C.) | Salt |
|---|---|---|---|---|---|---|
| 167 | 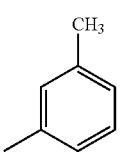 | —(CH₂)₂—CO—NH₂ | 9.4 | 499 | >260 | |
| 168 | 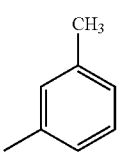 | —(CH₂)₃—SO₂—NH₂ | 9.3 | 495 | 130 (gum) | |
| 169 | 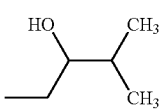 | 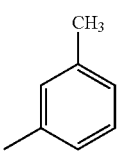 | 9.2 | 460 | 232 | |
| 170 | 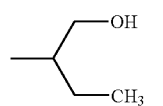 | 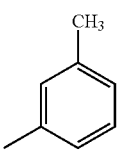 | 9.2 | 446 | 228 | |
| 171 | 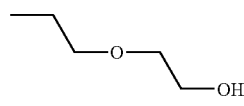 | 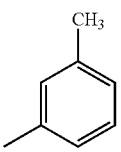 | 8.9 | 462 | 166 | HCl |
| 172 | 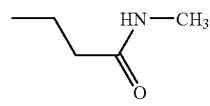 | 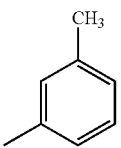 | 8.8 | 459 | 165 (gum) | HCl |
| 173 | 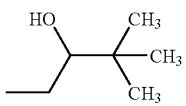 | 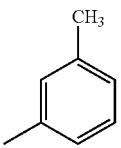 | 8.6 | 474 | 227 | |
| 174 | 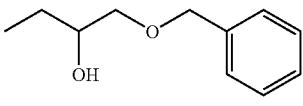 | | 8.6 | 538 | 170 | HCl |

US 8,044,073 B2
TABLE 3-continued
compounds prepared according to scheme B
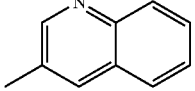
| Comp. No. | R¹ | R² | Activity | MH+ | Melting point (° C.) | Salt |
|---|---|---|---|---|---|---|
| 175 | 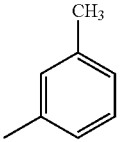 | —(CH₂)₂—OH | 8.5 | 455 | 244 | |
| 176 | 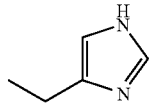 | 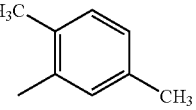 | 8.3 | 454 | 160 (gum) | |
| 177 | 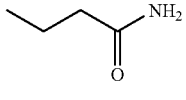 | 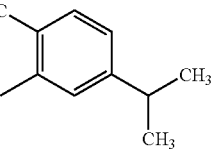 | 8.2 | 459 | 224 | |
| 178 | 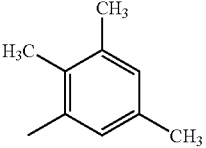 | —(CH₂)₂—OH | 7.8 | 460 | 175 (gum) | HCl |
| 179 | 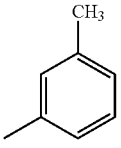 | —(CH₂)₂—OH | 7.6 | 446 | 232 | |
| 180 | 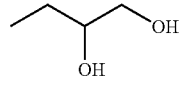 | 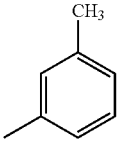 | 9.3 | 448 | 185 | |
| 181 | 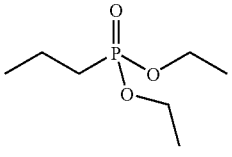 | 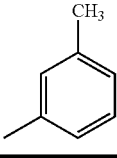 | 8.5 | 538 | 80 (gum) | |
| 182 | 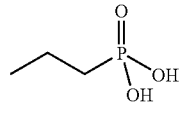 |  | 8.3 | 482 | 205 | HCl |

TABLE 3b

[Structure: 2-amino-benzimidazole with N-substituted (3-hydroxy-6-methylpyridin-2-yl)methyl group and N-linked methylene to 1-cyclopropyl-imidazo[4,5-c]pyridin-2(3H)-one]

| Comp. No. | Activity | MH+ | Melting point (° C.) | Salt |
|---|---|---|---|---|
| 183 | 7.4 | 442 | >250 | |

TABLE 4

[Core structure: 1-[(3-hydroxy-6-methylpyridin-2-yl)methyl]-6-R-benzimidazole]

| Comp. No. | R | Activity | MH+ | Melting point (° C.) | Salt form | Synthesis scheme |
|---|---|---|---|---|---|---|
| 184 | N-ethyl-3,5-dimethylaniline | 6.7 | 373 | | | O |
| 185 | N-ethyl-3,5-dichloroaniline | 6.1 | 413 | | | O |
| 186 | N-ethyl-3-chloroaniline | 5.8 | 379 | | | I |
| 187 | N-ethyl-3-ethylaniline | 5.7 | 373 | | | O |

TABLE 4-continued
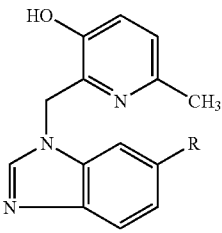
| Comp. No. | R | Activity | MH+ | Melting point (° C.) | Salt form | Synthesis scheme |
|---|---|---|---|---|---|---|
| 188 | propylamine | 5.1 | 297 | 205 | oxalate | N |
| 189 | butenenitrile | 4.8 | 291 | >250 | | N |
| 190 | N-methylbenzamide | <4.0 | 359 | >250 | | M |
| 191 | 2-(ethylamino)-4-methyl-(CH$_2$)$_3$-OH phenyl | 7.9 | 417 | 221 | | O |
| 192 | 2-(ethylamino)-4-methyl-(CH$_2$)$_2$-OH phenyl | 7.8 | 403 | 235 | | O |
| 193 | 3-(N-ethyl-N-(CH$_2$)$_2$-OH amino)-methylphenyl | 6.3 | 403 | 196 | | O |

TABLE 5a
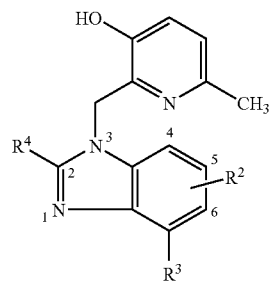
| Comp. No. | R² | R³ | R⁴ | Activity | MH+ | Melting point/salt | Synthesis scheme |
|---|---|---|---|---|---|---|---|
| 194 | 5-[NH-CH₂-C₆H₄-CH₃] (m-tolyl) | —CH₃ | —NH₂ | 7.9 | 388 | 252° C. | I |
| 195 | 5-[N(Et)(CH₂CH₂OH)-C₆H₄-CH₃] | H | —NH—CH₃ | 7.8 | 432 | 204° C. | P |
| 196 | 5-[-(CH₂)₃—NH₂] | H | —NH₂ | 7.7 | 312 | 195° C./HCl | J |
| 197 | 5-[CH(OH)-C₆H₅] | H | —NH₂ | 7.2 | 361 | — | L |
| 198 | 5-[-(CH₂)₂—CN] | H | —NH₂ | 6.8 | 308 | 242° C. | J |
| 199 | 5-[—CH₃] | —CH₃ | —NH₂ | 6.8 | 283 | >260° C. | K |
| 200 | 5-[—CH₂—OH] | H | —NH—CH₃ | 4.9 | 299 | >260° C. | P |
| 201 | 6-[(CH₂)₃-C₆H₅] | H | —NH₂ | <4.0 | 359 | >260° C. | J |
| 202 | 6-[CH₂—OH] | H | —NH—CH₃ | <4.0 | 299 | >260° C. | P |
| 203 | 6-[CH(OH)-C₆H₅] | H | —NH₂ | <4.0 | 361 | 221° C. | L |

TABLE 5a-continued
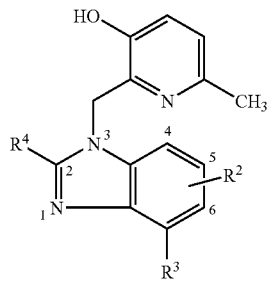
| Comp. No. | R² | R³ | R⁴ | Activity | MH+ | Melting point/salt | Synthesis scheme |
|---|---|---|---|---|---|---|---|
| 204 | 5-[3-(N-ethyl-N-(2-hydroxyethyl)amino)-methylphenyl] | H | —NH—CH₃ | 6.9 | 432 | 188° C. | P |
TABLE 5b
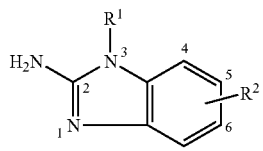
| Comp. No. | R¹ | R² | Activity | MH+ | Melting point/salt | Synthesis scheme |
|---|---|---|---|---|---|---|
| 205 | 8-ethylquinoline | 5-[3-(N-ethyl-N-(3-hydroxypropyl)amino)-methylphenyl] | 7.3 | 452 | 191° C. | Q |
| 206 | 5,6,7,8-tetrahydro-2,3,5-trimethylquinoxaline | 6-[2-(N-ethylamino)-4-methyl-(3-hydroxypropyl)phenyl] | 8.7 | 471 | 165° C. | U |

TABLE 5b-continued

| Comp. No. | R¹ | | R² | Activity | MH+ | Melting point/salt | Synthesis scheme |
|---|---|---|---|---|---|---|---|
| 207 | 5,8-dimethyl-5,6,7,8-tetrahydroquinoxalin-2,3-dimethyl | 5- | [2-(ethylamino)-5-isopropylphenyl]-(CH₂)₂—OH | 8.4 | 485 | 161° C. | U |
| 208 | 8-ethylquinoline | 6- | [2-(ethylamino)-5-methylphenyl]-(CH₂)₃—OH | 7.9 | 452 | 194° C. | X |
| 209 | 2-ethyl-3-methoxy-6-methylpyridine | 6- | [2-(ethylamino)-5-methylphenyl]-(CH₂)₃—OH | 7.8 | 446 | 212° C. | Y |
| 210 | 4-ethyl-1-methyl-1H-benzimidazole | 5- | [2-(ethylamino)-5-ethynylphenyl]-(CH₂)₂—OH | 7.8 | 451 | >260° C. | V |
| 211 | 4-ethyl-1-methyl-1H-benzimidazole | 6- | [2-(ethylamino)-5-methylphenyl]-(CH₂)₃—OH | 7.6 | 455 | 174° C. | V |
| 212 | 6-bromo-2-ethylpyridine | 6- | [2-(ethylamino)-5-methylphenyl]-(CH₂)₃—OH | 7.5 | 480 | 158° C. | Z |

TABLE 5b-continued
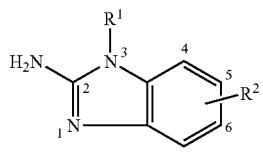
| Comp. No. | R¹ | R² | | Activity | MH+ | Melting point/salt | Synthesis scheme |
|---|---|---|---|---|---|---|---|
| 213 |  | 5- | 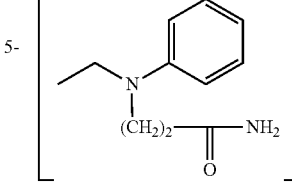 | 7.4 | 529 | 230° C. | Q |
| 214 |  | 6- | 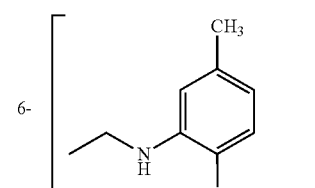 | 7.3 | 452 | 191° C. | X |
| 215 | 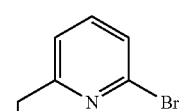 | 5- | 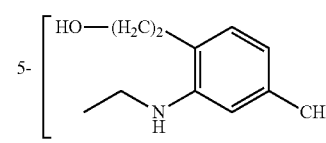 | 6.9 | 466 | | Z |
| 216 | 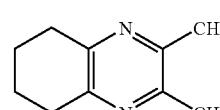 | 5- | 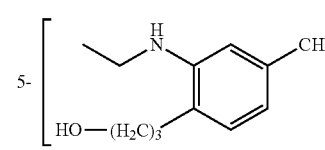 | 6.5 | 471 | 118° C. | U |
| 217 | 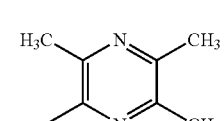 | 5- | 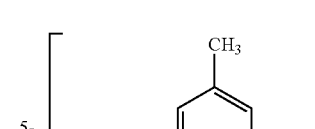 | 6.2 | 431 | 175° C. | AB |
| 218 |  | 6- | 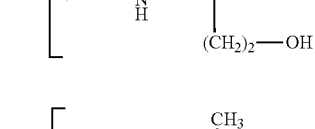 | 6.1 | 445 | 176° C. | AB |

TABLE 5b-continued

| Comp. No. | R¹ | R² | Activity | MH+ | Melting point/salt | Synthesis scheme |
|---|---|---|---|---|---|---|
| 219 | 4-fluorobenzyl | 6-[5-methyl-2-(3-hydroxypropyl)-N-ethylanilino] | 5.3 | 419 | 179° C. | AD |
| 220 | (6-bromopyridin-2-yl)methyl | 5-[2-(N-ethylamino)phenyl]propanamide | 4.8 | 479 | | Z |
| 221 | (3,5,6-trimethyl-pyrazin-2-yl)methyl | 6-[5-methyl-2-(3-hydroxypropyl)-N-ethylanilino] | <4.5 | 445 | 172° C. | AB |
| 222 | (8-quinolinyl)methyl | 5-(CH₂—OH) | 4.4 | 305 | 230° C. | Q |
| 223 | (1-methyl-1H-benzimidazol-4-yl)methyl | 5-(CH₂—OH) | <4 | 308 | 258° C. | V |
| 224 | (8-quinolinyl)methyl | 6-(CH₂—OH) | <4 | 305 | >260° C. | Q |

TABLE 5b-continued

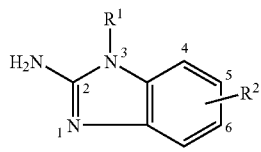

| Comp. No. | R¹ | R² | Activity | MH+ | Melting point/salt | Synthesis scheme |
|---|---|---|---|---|---|---|
| 225 | 8-ethylquinolin-... | 6-[3-methyl-N-ethyl-N-(CH₂)₃-OH-phenyl] | <4 | 452 | | Q |
| 226 | 6-bromo-2-ethylpyridin... | 5-(CH₂—OH) | <4 | 333 | 221° C. | Z |
| 227 | 6-bromo-2-ethylpyridin... | 6-(CH₂—OH) | <4 | 333 | 230° C. | Z |
| 228 | 6-bromo-2-ethylpyridin... | 6-[5-methyl-2-NH-ethyl-(CH₂)₃-OH-phenyl] | <4 | 480 | 140° C. | Z |
| 229 | 6-bromo-2-ethylpyridin... | 5-[2-NH-ethyl-(CH₂)₃-OH-phenyl] | <4 | 466 | | Z |
| 230 | 6-bromo-2-ethylpyridin... | 5-[2-CH₃,5-CH₃-NH-ethyl-phenyl] | <4 | 436 | | Z |
| 231 | 6-bromo-2-ethylpyridin... | 5-[3-CH₃-NH-ethyl-phenyl] | <4 | 422 | | Z |

TABLE 5b-continued
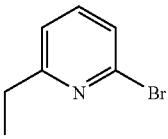
| Comp. No. | R¹ | R² | Activity | MH+ | Melting point/salt | Synthesis scheme |
|---|---|---|---|---|---|---|
| 232 | 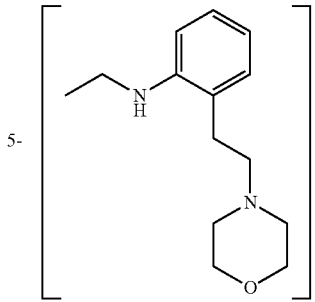 | 5- 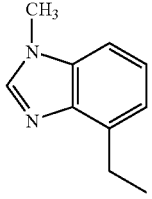 | <4 | 521 | | Z |
| 233 | 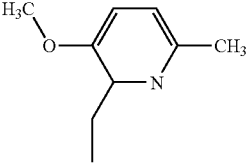 | 6-($CH_2$—OH) | <4 | 308 | 260° C. | V |
| 234 | 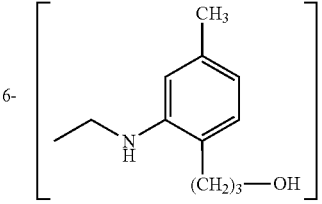 | 6- 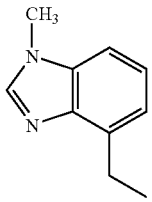 | <4 | 446 | 179° C. | Y |
| 235 | 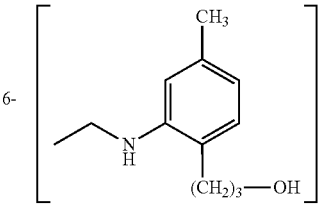 | 6- 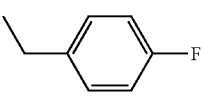 | <4 | 455 | 250° C. | V |
| 236 | 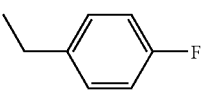 | 5-($CH_2$—OH) | <4 | 272 | 202° C. | AD |
| 237 | 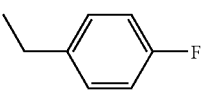 | 6-($CH_2$—OH) | <4 | 272 | >260° C. | AD |

TABLE 5b-continued
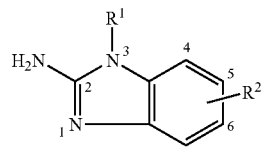
| Comp. No. | R¹ | R² | Activity | MH+ | Melting point/salt | Synthesis scheme |
|---|---|---|---|---|---|---|
| 238 | | 5- | 7.7 | 467 | 144° C. | U |
| 239 | | 5- | 8.2 | 525 | 228° C. | U |
| 240 | | 5- | 6.6 | 504 | | Y |

TABLE 6

[Core structure: 3-hydroxy-6-methylpyridin-2-yl-methyl attached to N1 of benzimidazole with R1 at 6-position and R2 at 5-position]

| Comp. No. | R1 | R2 | Activity | MH+ | Melting point | Synthesis scheme | Salt form |
|---|---|---|---|---|---|---|---|
| 241 | H | [3-(ethylamino)propyl-5-oxopyrrolidin-2-yl] | 4.5 | 394 | | O | |
| 242 | H | [N-methyl-3-methylbenzamide] | 4.2 | 373 | | M | |
| 243 | H | [2-(ethylamino)ethyl-1-methylpyrrole] | 4.2 | 376 | | O | |
| 244 | H | [N-methyl-2-phenylacetamide] | 4.2 | 373 | 215° C. | M | |
| 245 | H | [N-methyl-1-(2-aminoethyl)piperidine-4-carboxamide] | 4.2 | 409 | 144° C. | M | |
| 246 | H | —CH$_2$—OH | <4.0 | 270 | 181° C. | N | |
| 247 | —CH$_2$—OH | H | <4.0 | 270 | 234° C. | N | |
| 248 | [styryl] | H | <4.0 | 342 | >260° C. | N | |
| 249 | H | [styryl (cis)] | <4.0 | 342 | 248° C. | N | |
| 250 | H | [propylphenyl] | <4.0 | 344 | 191° C. | N | |
| 251 | [propylphenyl] | H | <4.0 | 344 | −225° C. | N | |
| 252 | H | —CH=CH—CN | <4.0 | 291 | 241° C. | N | |

TABLE 6-continued
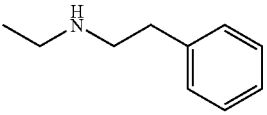
| Comp. No. | R1 | R2 | Activity | MH+ | Melting point | Synthesis scheme | Salt form |
|---|---|---|---|---|---|---|---|
| 253 | H | 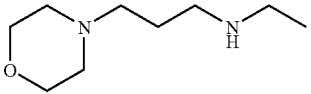 | <4.0 | 373 | 166° C. | O | |
| 254 | 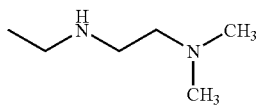 | H | <4.0 | 396 | 240° C. | O | HCl |
| 255 | H | 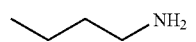 | <4.0 | 340 | >260° C. | O | |
| 256 | H | 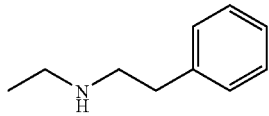 | <4.0 | 297 | 180° C. | N | |
| 257 | 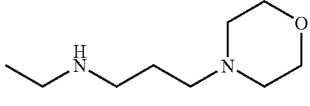 | H | <4.0 | 373 | 96° C. | O | |
| 258 | H | 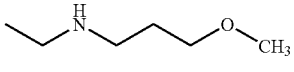 | <4.0 | 396 | >250° C. | O | HCl |
| 259 | H | —NH$_2$ | <4.0 | 255 | 248° C. | M | |
| 260 | H | 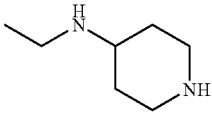 | <4.0 | 341 | 120° C. | O | |
| 261 | —NH$_2$ | H | <4.0 | 255 | >250° C. | M | |
| 262 | H | 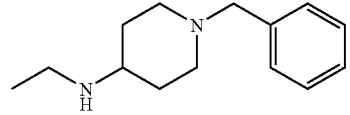 | <4.0 | 352 | 210° C. | O | HCl |
| 263 | 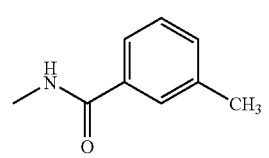 | H | <4.0 | 442 | 182° C. | O | |
| 264 |  | H | <4.0 | 373 | >250° C. | M | |

TABLE 6-continued
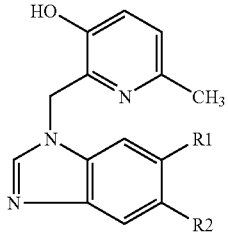
| Comp. No. | R1 | R2 | Activity | MH+ | Melting point | Synthesis scheme | Salt form |
|---|---|---|---|---|---|---|---|
| 265 | H | 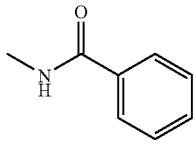 | <4.0 | 359 | 184° C. | O | |
| 266 | H | 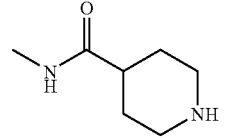 | <4.0 | 359 | 168° C. | O | |
| 267 | H | 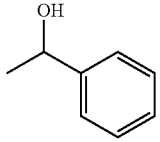 | <4.0 | 366 | >250° C. | M | |
| 268 | 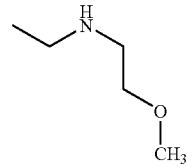 | H | <4.0 | 346 | 150° C. | I | |
| 269 | H | 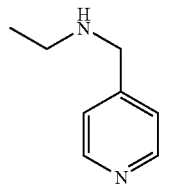 | <4.0 | 327 | | O | |
| 270 | H | 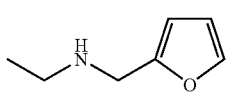 | <4.0 | 360 | | O | |
| 271 | H | 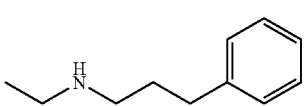 | <4.0 | 349 | | O | |
| 272 | H | 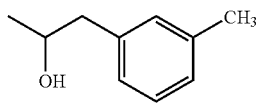 | <4.0 | 387 | | O | |
| 273 | H | <4.0 | 374 | 172° C. | I | oxalate |

TABLE 6-continued

| Comp. No. | R1 | R2 | Activity | MH+ | Melting point | Synthesis scheme | Salt form |
|---|---|---|---|---|---|---|---|
| 274 | H | 1-phenyl-1-hydroxyethyl | <4.0 | 346 | 170° C. | I | oxalate |
| 275 | N-methyl phenylacetamide | H | <4.0 | 373 | 170° C. | M | |
| 276 | N-methyl 2-pyridylacetamide | H | <4.0 | 374 | 175° C. | M | |
| 277 | N-methyl 3-phenylpropanamide | H | <4.0 | 387 | 255° C. | M | |
| 278 | N-methyl nicotinamide | H | <4.0 | 360 | >260° C. | M | |
| 279 | H | N-methyl nicotinamide | <4.0 | 360 | >260° C. | M | |
| 280 | H | N-methyl 3-phenylpropanamide | <4.0 | 387 | 225° C. | M | |
| 281 | H | N-methyl 2-pyridylacetamide | <4.0 | 374 | 190° C. | M | |

TABLE 6-continued
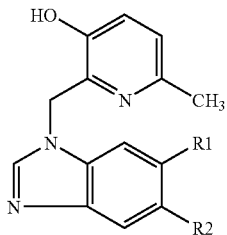
| Comp. No. | R1 | R2 | Activity | MH+ | Melting point | Synthesis scheme | Salt form |
|---|---|---|---|---|---|---|---|
| 282 | ![3-(ethylamino)acetophenone] | H | <4.0 | 387 | | O | |
| 283 | ![8-(ethylamino)quinoline] | H | <4.0 | 296 | | O | |
| 284 | ![N-ethyl-2,3-dimethylaniline] | H | <4.0 | 373 | | O | |
| 285 | ![N-ethylaniline] | H | <4.0 | 345 | | O | |
| 286 | H | ![3-(ethylamino)acetophenone] | <4.0 | 387 | | O | |
| 287 | H | ![3-bromo-N-ethylaniline] | <4.0 | 423 | | O | |
| 288 | H | ![3-chloro-N-ethylaniline] | <4.0 | 379 | | O | |

TABLE 6-continued

| Comp. No. | R1 | R2 | Activity | MH+ | Melting point | Synthesis scheme | Salt form |
|---|---|---|---|---|---|---|---|
| 289 | H | *N-ethyl-3,5-dimethylaniline* | <4.0 | 373 | | O | |
| 290 | H | *N-ethyl-3,5-dichloroaniline* | <4.0 | 413 | | O | |
| 291 | H | *N-ethyl-8-aminoquinoline* | <4.0 | 396 | | O | |
| 292 | H | *N-ethyl-3-cyanoaniline* | <4.0 | 369 | | O | |
| 293 | H | *N-ethyl-3-fluoroaniline* | <4.0 | 363 | | O | |
| 294 | H | *N-ethyl-3-ethylaniline* | <4.0 | 373 | | O | |
| 295 | H | *N-ethyl-2,3-dimethylaniline* | <4.0 | 373 | | O | |

TABLE 6-continued

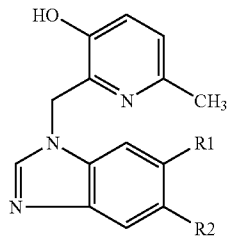

| Comp. No. | R1 | R2 | Activity | MH+ | Melting point | Synthesis scheme | Salt form |
|---|---|---|---|---|---|---|---|
| 296 | H | 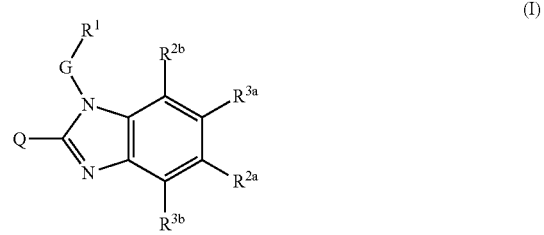 | <4.0 | 345 | | O | |

Example 31

In Vitro Screening of Compounds of Formula (I) for Activity Against RSV

The percent protection against cytopathology caused by viruses (antiviral activity or $EC_{50}$) achieved by tested compounds and their cytotoxicity ($CC_{50}$) are both calculated from dose-response curves. The selectivity of the antiviral effect is represented by the selectivity index (SI), calculated by dividing the $CC_{50}$ (cytotoxic dose for 50% of the cells) by the $EC_{50}$ (antiviral activity for 50% of the cells). The tables in the above experimental part list the category to which each of the prepared compounds belong: Compounds belonging to activity category "A" have a $pEC_{50}$ (–log of $EC_{50}$ when expressed in molar units) equal to or more than 7. Compounds belonging to activity category "B" have a pEC50 value between 6 and 7. Compounds belonging to activity category "C" have a pEC50 value equal to or below 6.

Automated tetrazolium-based colorimetric assays were used for determination of $EC_{50}$ and $CC_{50}$ of test compounds. Flat-bottom, 96-well plastic microtiter trays were filled with 180 μl of Eagle's Basal Medium, supplemented with 5% FCS (0% for FLU) and 20 mM Hepes buffer. Subsequently, stock solutions (7.8× final test concentration) of compounds were added in 45 μl volumes to a series of triplicate wells so as to allow simultaneous evaluation of their effects on virus- and mock-infected cells. Five five-fold dilutions were made directly in the microtiter trays using a robot system. Untreated virus controls, and HeLa cell controls were included in each test. Approximately 100 $TCID_{50}$ of Respiratory Syncytial Virus was added to two of the three rows in a volume of 50 μl. The same volume of medium was added to the third row to measure the cytotoxicity of the compounds at the same concentrations as those used to measure the antiviral activity. After two hours of incubation, a suspension (4×10⁵ cells/ml) of HeLa cells was added to all wells in a volume of 50 μl. The cultures were incubated at 37° C. in a 5% $CO_2$ atmosphere. Seven days after infection the cytotoxicity and the antiviral activity was examined spectrophotometrically. To each well of the microtiter tray, 25 μl of a solution of MTT (3-(4,5-dimethylthiazol-2-yl)-2,5-diphenyltetrazolium bromide) was added. The trays were further incubated at 37° C. for 2 hours, after which the medium was removed from each cup. Solubilization of the formazan crystals was achieved by adding 100 μl 2-propanol. Complete dissolution of the formazan crystals were obtained after the trays have been placed on a plate shaker for 10 min. Finally, the absorbances were read in an eight-channel computer-controlled photometer (Multiskan MCC, Flow Laboratories) at two wavelengths (540 and 690 nm). The absorbance measured at 690 nm was automatically subtracted from the absorbance at 540 nm, so as to eliminate the effects of non-specific absorption.

The percent protection against cytopathology caused by viruses (antiviral activity or $EC_{50}$) achieved by tested compounds and their cytotoxicity ($CC_{50}$) were both calculated from dose-response curves. The selectivity of the antiviral effect is represented by the selectivity index (SI), calculated by dividing the $CC_{50}$ (cytotoxic dose for 50% of the cells) by the $EC_{50}$ (antiviral activity for 50% of the cells).

The invention claimed is:
1. A compound having the formula

(I)

a N-oxide, addition salt, or a stereochemically isomeric form thereof; wherein
G is a direct bond or $C_{1-10}$alkanediyl optionally substituted with one or more substituents independently selected from the group of substituents consisting of hydroxy, $C_{1-6}$alkyloxy, $Ar^1C_{1-6}$alkyloxy, $C_{1-6}$alkylthio, $Ar^1C_{1-6}$alkylthio, HO(—$CH_2$—$CH_2$—O)$_n$—, $C_{1-6}$alkyloxy(—$CH_2$—$CH_2$—O)$_n$— or $Ar^1C_{1-6}$alkyloxy(—$CH_2$—$CH_2$—O)$_n$—;
each n independently is 1, 2, 3 or 4;
$R^1$ is pyridyl;
wherein said pyridyl may optionally be substituted with 1 or where possible more, substituents independently selected from the group of substituents consisting of halo, hydroxy, amino, cyano, carboxyl, $C_{1-6}$alkyl, $C_{1-6}$alkyloxy, $C_{1-6}$alkylthio, $C_{1-6}$alkyloxy$C_{1-6}$alkyl, $Ar^1$, $Ar^1C_{1-6}$alkyl, $Ar^1C_{1-6}$alkyloxy, hydroxy$C_{1-6}$alkyl, mono-or di($C_{1-6}$alkyl)amino, mono-or di($C_{1-6}$alkyl)amino$C_{1-6}$alkyl, polyhalo$C_{1-6}$alkyl, $C_{1-6}$alkylcarbonylamino, $C_{1-6}$alkyl-SO$_2$—NR$^{5c}$—, Ar$^1$—SO$_2$—NR$^{5c}$—, $C_{1-6}$alkyloxycarbonyl, —C(=O)—NR$^{5c}$R$^{5d}$, HO(—CH$_2$—CH$_2$—O)$_n$—, halo(—CH$_2$—CH$_2$—O)$_n$—, $C_{1-6}$alkyloxy(—CH$_2$—CH$_2$—O)$_n$—, Ar$^1C_{1-6}$alkyloxy(—CH$_2$—CH$_2$—O)$_n$— and mono-or di($C_{1-6}$alkyl)amino(—CH$_2$—CH$_2$—O)$_n$—;

each t independently is 0, 1 or 2;

Q is hydrogen, amino or mono- or di($C_{1-4}$alkyl)amino;

$R^{2a}$ and $R^{3a}$ are each independently selected from hydrogen, halo, optionally mono- or polysubstituted $C_{1-6}$alkyl, optionally mono- or polysubstituted $C_{2-6}$alkenyl, nitro, hydroxy, Ar$^2$, N(R$^{4a}$R$^{4b}$), N(R$^{4a}$R$^{4b}$)sulfonyl, N(R$^{4a}$R$^{4b}$)carbonyl, $C_{1-6}$alkyloxy, Ar$^2$oxy, Ar$^2C_{1-6}$alkyloxy, carboxyl, $C_{1-6}$alkyloxycarbonyl, or —C(=Z)Ar$^2$; wherein =Z is =O, =CH—C(=O)—NR$^{5a}$R$^{5b}$, =CH$_2$, =CH—$C_{1-6}$alkyl, =N—OH or =N—O—$C_{1-6}$ alkyl; and wherein the optional substituents on $C_{1-6}$alkyl and $C_{2-6}$alkenyl can be the same or can be different relative to one another, and are each independently selected from the group of substituents consisting of hydroxy, cyano, halo, nitro, N(R$^{4a}$R$^{4b}$), N(R$^{4a}$R$^{4b}$)sulfonyl, Ar$^2$, $C_{1-6}$alkyloxy, $C_{1-6}$alkyl-S(=O)$_t$, Ar$^2$oxy, Ar$^2$—S(=O)$_t$, Ar$^2C_{1-6}$alkyloxy, Ar$^2C_{1-6}$alkyl-S(=O)$_t$, carboxyl, $C_{1-6}$alkyloxycarbonyl and —C(=Z)Ar$^2$;

provided that when $R^{2a}$ is halo, optionally mono- or polysubstituted $C_{1-6}$alkyl, optionally mono- or polysubstituted $C_{2-6}$alkenyl, nitro, hydroxy, Ar$^2$, N(R$^{4a}$R$^{4b}$), N(R$^{4a}$R$^{4b}$)sulfonyl, N(R$^{4a}$R$^{4b}$)carbonyl, $C_{1-6}$alkyloxy, Ar$^2$oxy, Ar$^2C_{1-6}$alkyloxy, carboxyl, $C_{1-6}$alkyloxycarbonyl, or —C(=Z)Ar$^2$; then $R^{3a}$ is hydrogen; and provided that when $R^{3a}$ is halo, optionally mono- or polysubstituted $C_{1-6}$alkyl, optionally mono- or polysubstituted $C_{2-6}$alkenyl, nitro, hydroxy, Ar$^2$, N(R$^{4a}$R$^{4b}$), N(R$^{4a}$R$^{4b}$)sulfonyl, N(R$^{4a}$R$^{4b}$)carbonyl, $C_{1-6}$alkyloxy, Ar$^2$oxy, Ar$^2C_{1-6}$alkyloxy, carboxyl, $C_{1-6}$alkyloxycarbonyl, or —C(=Z)Ar$^2$; then $R^{2a}$ is hydrogen;

$R^{2b}$ and $R^{3b}$ are each independently selected from hydrogen, $C_{1-6}$alkyl or halogen;

provided that when $R^{2a}$ is halo, optionally mono- or polysubstituted $C_{1-6}$alkyl, optionally mono- or polysubstituted $C_{2-6}$alkenyl, nitro, hydroxy, Ar$^2$, N(R$^{4a}$R$^{4b}$)sulfonyl, N(R$^{4a}$R$^{4b}$)sulfonyl, N(R$^{4a}$R$^{4b}$)carbonyl, $C_{1-6}$alkyloxy, Ar$^2$oxy, Ar$^2C_{1-6}$alkyloxy, carboxyl, $C_{1-6}$alkyloxycarbonyl, or —C(=Z)Ar$^2$ then $R^{2b}$ is hydrogen, $C_{1-6}$alkyl or halogen and $R^{3b}$ is hydrogen; and provided that when $R^{3a}$ is halo, optionally mono- or polysubstituted $C_{1-6}$alkyl, optionally mono- or polysubstituted $C_{2-6}$alkenyl, nitro, hydroxy, Ar$^2$, N(R$^{4a}$R$^{4b}$), N(R$^{4a}$R$^{4b}$)sulfonyl, N(R$^{4a}$R$^{4b}$)carbonyl, $C_{1-6}$alkyloxy, Ar$^2$oxy, Ar$^2C_{1-6}$alkyloxy, carboxyl, $C_{1-6}$alkyloxycarbonyl, or —C(=Z)Ar$^2$ then $R^{3b}$ is hydrogen, $C_{1-6}$alkyl or halogen and $R^{2b}$ is hydrogen;

$R^{4a}$ and $R^{4b}$ can be the same or can be different relative to one another, and are each independently selected from the group of substituents consisting of hydrogen, $C_{1-6}$alkyl, Ar$^2C_{1-6}$alkyl, (Ar$^2$)(hydroxy)$C_{1-6}$alkyl, hydroxy$C_{1-6}$alkyl, mono- and di-($C_{1-6}$alkyloxy)$C_{1-6}$alkyl, (hydroxy$C_{1-6}$alkyl)oxy$C_{1-6}$alkyl, Ar$^1C_{1-6}$alkyloxy-$C_{1-6}$alkyl, dihydroxy$C_{1-6}$alkyl, ($C_{1-6}$alkyloxy)(hydroxy)$C_{1-6}$alkyl, (Ar$^1C_{1-6}$alkyloxy)(hydroxy)$C_{1-6}$alkyl, Ar$^1$oxy-$C_{1-6}$alkyl, (Ar$^1$oxy)(hydroxy)-$C_{1-6}$alkyl, amino$C_{1-6}$alkyl, mono- and di($C_{1-6}$alkyl)amino-$C_{1-6}$alkyl, carboxyl-$C_{1-6}$alkyl, $C_{1-6}$alkyloxycarbonyl$C_{1-6}$alkyl, aminocarbonyl$C_{1-6}$alkyl, mono- and di($C_{1-6}$alkyl)aminocarbonyl$C_{1-6}$alkyl, $C_{1-6}$alkylcarbonyl$C_{1-6}$alkyl, ($C_{1-4}$alkyloxy)$_2$-P(=O)—$C_{1-6}$alkyl, ($C_{1-4}$alkyloxy)$_2$P(=O)—O—$C_{1-6}$alkyl, aminosulfonyl-$C_{1-6}$alkyl, mono- and di($C_{1-6}$alkyl)aminosulfonyl-$C_{1-6}$alkyl, $C_{1-6}$alkylcarbonyl, Ar$^2$carbonyl, Ar$^2C_{1-6}$alkylcarbonyl, $C_{1-6}$alkylsulfonyl, aminosulfonyl, mono- and di($C_{1-6}$alkyl)aminosulfonyl, Ar$^2$sulfonyl, Ar$^2C_{1-6}$alkylsulfonyl, Ar$^2$;

$R^{5a}$ and $R^{5b}$ can be the same or can be different relative to one another, and are each independently hydrogen or $C_{1-6}$alkyl; or $R^{5c}$ and $R^{5d}$ taken together may form a bivalent radical of formula —(CH$_2$)$_s$— wherein s is 4 or 5;

$R^{5c}$ and $R^{5d}$ can be the same or can be different relative to one another, and are each independently hydrogen or $C_{1-6}$alkyl; or $R^{5c}$ and $R^{5d}$ taken together may form a bivalent radical of formula —(CH$_2$)$_s$— wherein s is 4 or 5;

$R^{6a}$ is hydrogen, $C_{1-6}$alkyl, Ar$^1$, Ar$^1C_{1-6}$alkyl, $C_{1-6}$alkylcarbonyl, Ar$^1$carbonyl, Ar$^1C_{1-6}$alkylcarbonyl, $C_{1-6}$alkylsulfonyl, Ar$^1$sulfonyl, Ar$^1C_{1-6}$alkylsulfonyl, $C_{1-6}$alkyloxy$C_{1-6}$alkyl, amino$C_{1-6}$alkyl, mono- or di($C_{1-6}$alkyl)amino$C_{1-6}$alkyl, hydroxy$C_{1-6}$alkyl, (carboxyl)-$C_{1-6}$alkyl, ($C_{1-6}$alkyloxycarbonyl)-$C_{1-6}$alkyl, aminocarbonyl$C_{1-6}$alkyl, mono- and di($C_{1-6}$alkyl)aminocarbonyl$C_{1-6}$alkyl, aminosulfonyl-$C_{1-6}$alkyl, mono- and di($C_{1-6}$alkyl)aminosulfonyl-$C_{1-6}$alkyl;

$R^{6b}$ is hydrogen, $C_{1-6}$alkyl, Ar$^1$ or Ar$^1C_{1-6}$alkyl;

$R^{6c}$ is $C_{1-6}$alkyl, Ar$^1$ or Ar$^1C_{1-6}$alkyl;

Ar$^1$ is phenyl or phenyl substituted with 1 or more, substituents selected from halo, hydroxy, $C_{1-6}$alkyl, hydroxy$C_{1-6}$alkyl, polyhalo$C_{1-6}$alkyl, and $C_{1-6}$alkyloxy;

Ar$^2$ is phenyl, phenyl annelated with $C_{5-7}$cycloalkyl, or phenyl substituted with 1 or more, substituents selected from halo, cyano, $C_{1-6}$alkyl, Ar$^1$—$C_{1-6}$alkyl, cyano$C_{1-6}$alkyl, $C_{2-6}$alkenyl, cyano$C_{2-6}$alkenyl, R$^{6b}$—O—$C_{3-6}$alkenyl, $C_{2-6}$alkynyl, cyano$C_{2-6}$alkynyl, R$^{6b}$—O—$C_{3-6}$alkynyl, Ar$^1$, R$^{6b}$—O—, R$^{6b}$—S—, R$^{6c}$—SO—, R$^{6c}$—SO$_2$—, R$^{6b}$—O—$C_{1-6}$alkyl-SO$_2$—, —N(R$^{6a}$R$^{6b}$), polyhalo-$C_{1-6}$alkyl, polyhalo$C_{1-6}$alkyloxy, polyhalo$C_{1-6}$alkylthio, R$^{6c}$—C(=O)—, R$^{6b}$—O—C(=O)—, N(R$^{6a}$R$^{6b}$)—C(=O)—, R$^{6b}$—O—$C_{1-10}$alkyl, R$^{6b}$—S—$C_{1-6}$alkyl, R$^{6c}$—S(=O)$_2$—$C_{1-6}$alkyl, N(R$^{6a}$R$^{6b}$)—$C_{1-6}$alkyl, R$^{6c}$—C(=O)—$C_{1-6}$alkyl, R$^{6b}$—O—C(=O)—$C_{1-6}$alkyl, N(R$^{6a}$R$^{6b}$)—C(=O)—$C_{1-6}$alkyl, R$^{6c}$—C(=O)—NR$^{6b}$—, R$^{6c}$—C(=O)—O—, R$^{6c}$—C(=O)—NR$^{6b}$—$C_{1-6}$alkyl, R$^{6c}$—C(=O)—O—$C_{1-6}$alkyl, N(R$^{6a}$R$^{6b}$)—S(=O)$_2$—, H$_2$N—C(=NH)—.

2. A compound according to claim 1 wherein the compound has the formula:

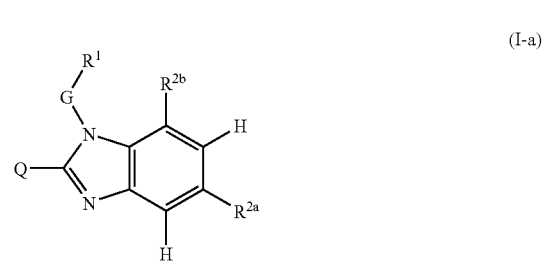

(I-a)

wherein Q, G, R$^1$, R$^{2a}$ and R$^{2b}$ are as claimed in claim 1.

3. A compound according to claim 1 wherein the compound has the formula:

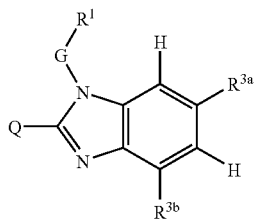

(I-b)

wherein Q, G, $R^1$, $R^{3a}$ and $R^{3b}$ are as claimed in claim 1.

4. A compound according to claim 1 wherein the compound has the formula:

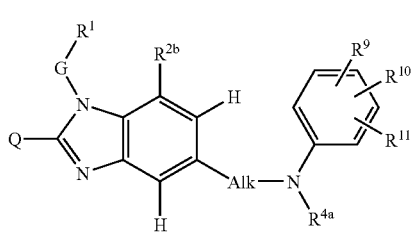

(I-a-1)

wherein Q, G, $R^1$, $R^{4a}$ and $R^{2b}$ are as claimed in claim 1; and Alk is $C_{1-6}$alkanediyl;

$R^9$, $R^{10}$, $R^{11}$ each independently are selected from halo, cyano, $C_{1-6}$alkyl, $Ar^1$—$C_{1-6}$alkyl, cyano$C_{1-6}$alkyl, $C_{2-6}$alkenyl, cyano$C_{2-6}$alkenyl, $R^{6b}$—O—$C_{3-6}$alkenyl, $C_{2-6}$alkynyl, cyano$C_{2-6}$alkynyl, $R^{6b}$—O—$C_{3-6}$alkynyl, $Ar^1$, $R^{6b}$—O—, $R^{6b}$—S—, $R^{6c}$—SO—, $R^{6c}$—SO$_2$—, $R^{6b}$—O—$C_{1-6}$alkyl-SO$_2$—, —N($R^{6a}R^{6b}$), polyhalo$C_{1-6}$alkyl, polyhalo$C_{1-6}$alkyloxy, polyhalo$C_{1-6}$alkylthio, $R^{6c}$—C(=O)—, $R^{6b}$—O—C(=O)—, N($R^{6a}R^{6b}$)—C(=O)—, $R^{6b}$—O—$C_{1-6}$alkyl, $R^{6b}$—S—$C_{1-6}$alkyl, $R^{6c}$—S(=O)$_2$—$C_{1-6}$alkyl, N($R^{6a}R^{6b}$)—$C_{1-6}$alkyl, $R^{6c}$—C(=O)—$C_{1-6}$alkyl, $R^{6b}$—O—C(=O)—$C_{1-6}$alkyl, N($R^{6a}R^{6b}$)—C(=O)—$C_{1-6}$alkyl, $R^{6c}$—C(=O)—NR$^{6b}$—, $R^{6c}$—C(=O)—O—, $R^{6c}$—C(=O)—NR$^{6b}$—$C_{1-6}$alkyl, $R^{6c}$—C(=O)—O—$C_{1-6}$alkyl, N($R^{6a}R^{6b}$)—S(=O)$_2$—, H$_2$N—C(=NH)—.

5. A compound according to claim 1 wherein the compound has the formula:

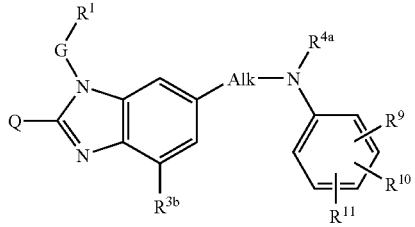

(I-b-1)

wherein Q, G, $R^1$, $R^{4a}$, $R^{3b}$ are as claimed in claim 1; and $R^9$, $R^{10}$, $R^{11}$ each independently are selected from hydrogen, halo, cyano, $C_{1-6}$alkyl, $Ar^1$—$C_{1-6}$alkyl, cyano$C_{1-6}$alkyl, $C_{2-6}$alkenyl, cyano$C_{2-6}$alkenyl, $R^{6b}$—O—$C_{3-6}$alkenyl, $C_{2-6}$alkynyl, cyano$C_{2-6}$alkynyl, $R^{6b}$—O—$C_{3-6}$ alkynyl, $Ar^1$, $R^{6b}$—O—, $R^{6b}$—S—, $R^{6c}$—SO—, $R^{6c}$—SO$_2$—, $R^{6b}$—O—$C_{1-6}$alkyl-SO$_2$—, —N($R^{6a}R^{6b}$), polyhalo$C_{1-6}$alkyl, polyhalo$C_{1-6}$alkyloxy, polyhalo$C_{1-6}$alkylthio, $R^{6c}$—C(=O)—, $R^{6b}$—O—C(=O)—, N($R^{6a}R^{6b}$)—C(=O)—, $R^{6b}$—O—$C_{1-6}$alkyl, $R^{6b}$—S—$C_{1-6}$alkyl, $R^{6c}$—S(=O)$_2$—$C_{1-6}$alkyl, N($R^{6a}R^{6b}$)—$C_{1-6}$ alkyl, $R^{6c}$—C(=O)—$C_{1-6}$alkyl, $R^{6b}$—O—C(=O)—$C_{1-6}$alkyl, N($R^{6a}R^{6b}$)—C(=O)—$C_{1-6}$alkyl, $R^{6c}$—C(=O)—NR$^{6b}$—, $R^{6c}$—C(=O)—O—, $R^{6c}$—C(=O)—NR$^{6b}$—$C_{1-6}$alkyl, $R^{6c}$—C(=O)—O—$C_{1-6}$alkyl, N($R^{6a}R^{6b}$)—S(=O)$_2$—, H$_2$N—C(=NH)—; and Alk is $C_{1-6}$alkanediyl.

6. A compound according to claim 1 wherein the compound has the formula:

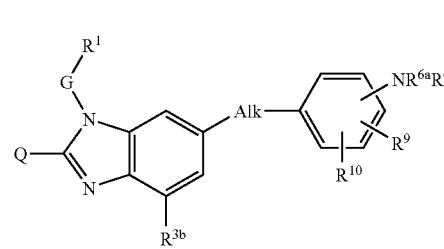

(I-c-1)

wherein Q, G, $R^1$, $R^{3b}$ are as claimed in claim 1;

$R^9$ and $R^{10}$ each independently are selected from halo, cyano, $C_{1-6}$alkyl, $Ar^1$—$C_{1-6}$alkyl, cyano$C_{1-6}$alkyl, $C_{2-6}$alkenyl, cyano$C_{2-6}$alkenyl, $R^{6b}$—O—$C_{3-6}$alkenyl, $C_{2-6}$alkynyl, cyano$C_{2-6}$alkynyl, $R^{6b}$—O—$C_{3-6}$alkynyl, $Ar^1$, $R^{6b}$—O—, $R^{6b}$—S—, $R^{6c}$—SO—, $R^{6c}$—SO$_2$—, $R^{6b}$—O—$C_{1-6}$alkyl-SO$_2$—, —N($R^{6a}R^{6b}$, polyhalo$C_{1-6}$ alkyl, polyhalo$C_{1-6}$alkyloxy, polyhalo$C_{1-6}$alkylthio, $R^{6c}$—C(=O)—, $R^{6b}$—O—C(=O)—, N($R^{6a}R^{6b}$)—C(=O)—, $R^{6b}$—O—$C_{1-6}$alkyl, $R^{6b}$—S—$C_{1-6}$alkyl, $R^{6c}$—S(=O)$_2$—$C_{1-6}$alkyl, N($R^{6a}R^{6b}$)—$C_{1-6}$alkyl, $R^{6c}$—C(=O)—$C_{1-6}$alkyl, $R^{6b}$—O—C(=O)—$C_{1-6}$ alkyl, N($R^{6a}R^{6b}$)—C(=O)—$C_{1-6}$alkyl, $R^{6c}$—C(=O)—NR$^{6b}$—, $R^{6c}$—C(=O)—O—, $R^{6c}$—C(=O)—NR$^{6b}$—$C_{1-6}$alkyl, $R^{6c}$—C(=O)—O—$C_{1-6}$alkyl, N($R^{6a}R^{6b}$)—S(=O)$_2$—, H$_2$N—C(=NH)—;

Alk is $C_{1-6}$alkanediyl;

$R^{6a}$ is hydrogen, $C_{1-6}$alkyl, $Ar^1$, $Ar^1C_{1-6}$alkyl, $C_{1-6}$alkylcarbonyl, $Ar^1$carbonyl, $Ar^1C_{1-6}$alkylcarbonyl, $C_{1-6}$alkylsulfonyl, $Ar^1$sulfonyl, $Ar^1C_{1-6}$alkylsulfonyl, $C_{1-6}$alkyloxy$C_{1-6}$alkyl, amino$C_{1-6}$alkyl, mono- or di($C_{1-6}$alkyl)amino$C_{1-6}$alkyl, hydroxy$C_{1-6}$alkyl, (carboxyl)-$C_{1-6}$alkyl, ($C_{1-6}$alkyloxycarbonyl)-$C_{1-6}$alkyl, aminocarbonyl$C_{1-6}$alkyl, mono- and di($C_{1-6}$alkyl)aminocarbonyl$C_{1-6}$alkyl, aminosulfonyl-$C_{1-6}$alkyl, mono- and di($C_{1-6}$alkyl)aminosulfonyl-$C_{1-6}$alkyl; and $R^{6b}$ is hydrogen, $C_{1-6}$alkyl, $Ar^1$ or $Ar^1C_{1-6}$alkyl.

7. A compound according to claim 1 wherein the compound has the formula:

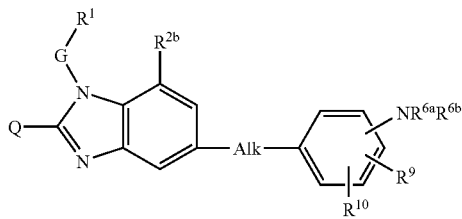

(I-c-2)

wherein Q, G, $R^1$, $R^{2b}$ are as claimed in claim 1;
$R^9$ and $R^{10}$ each independently are selected from halo, cyano, $C_{1-6}$alkyl, $Ar^1$—$C_{1-6}$alkyl, cyano$C_{1-6}$alkyl, $C_{2-6}$alkenyl, cyano$C_{2-6}$alkenyl, $R^{6b}$—O—$C_{3-6}$alkenyl, $C_{2-6}$alkynyl, cyano$C_{2-6}$alkynyl, $R^{6b}$—O—$C_{3-6}$alkynyl, $Ar^1$, $R^{6b}$—O—, $R^{6b}$—S—, $R^{6c}$—SO—, $R^{6c}$—SO$_2$—, $R^{6b}$—O—$C_{1-6}$alkyl-SO$_2$—, —N($R^{6a}R^{6b}$), polyhalo$C_{1-6}$ alkyl, polyhalo$C_{1-6}$alkyloxy, polyhalo$C_{1-6}$alkylthio, $R^{6c}$—C(=O)—, $R^{6b}$—O—C(=O)—, N($R^{6a}R^{6b}$)—C(=O)—, $R^{6b}$—O—$C_{1-6}$alkyl, $R^{6b}$—S—$C_{1-6}$alkyl, $R^{6c}$—S(=O)$_2$—$C_{1-6}$alkyl, N($R^{6a}R^{6b}$)—$C_{1-6}$alkyl, $R^{6c}$—C(=O)—$C_{1-6}$alkyl, $R^{6b}$—O—C(=O)—$C_{1-6}$ alkyl, N($R^{6a}R^{6b}$)—C(=O)—$C_{1-6}$alkyl, $R^{6c}$—C(=O)—NR$^{6b}$—, $R^{6c}$—C(=O)—O—, $R^{6c}$—C(=O)—NR$^{6b}$—$C_{1-6}$alkyl, $R^{6c}$—C(=O)—O—$C_{1-6}$alkyl, N($R^{6a}R^{6b}$)—S(=O)$_2$—, $H_2N$—C(=NH)—;
Alk is $C_{1-6}$alkanediyl;
$R^{6a}$ is hydrogen, $C_{1-6}$alkyl, $Ar^1$, $Ar^1C_{1-6}$alkyl, $C_{1-6}$alkylcarbonyl, $Ar^1$carbonyl, $Ar^1C_{1-6}$alkylcarbonyl, $C_{1-6}$alkylsulfonyl, $Ar^1$sulfonyl, $Ar^1C_{1-6}$alkylsulfonyl, $C_{1-6}$alkyloxy$C_{1-6}$alkyl, amino$C_{1-6}$alkyl, mono- or di($C_{1-6}$alkyl)amino$C_{1-6}$alkyl, hydroxy$C_{1-6}$alkyl, (carboxyl)-$C_{1-6}$alkyl, ($C_{1-6}$alkyloxycarbonyl)-$C_{1-6}$alkyl, aminocarbonyl$C_{1-6}$alkyl, mono- and di($C_{1-6}$alkyl)aminocarbonyl$C_{1-6}$alkyl, aminosulfonyl-$C_{1-6}$alkyl, mono- and di($C_{1-6}$alkyl)aminosulfonyl-$C_{1-6}$alkyl; and
$R^{6b}$ is hydrogen, $C_{1-6}$alkyl, $Ar^1$ or $Ar^1C_{1-6}$alkyl.

8. A compound according to claim 5, wherein Alk is methylene.

9. A compound according to claim 5, wherein $R^9$, $R^{10}$, $R^{11}$ are selected from hydrogen, halo, cyano, $C_{1-6}$alkyl, $Ar^1$—$C_{1-6}$ alkyl, cyano$C_{1-6}$alkyl, $C_{2-6}$alkenyl, cyano$C_{2-6}$alkenyl, $R^{6b}$—O—$C_{3-6}$alkenyl, $C_{2-6}$alkynyl, cyano$C_{2-6}$alkynyl, $R^{6b}$—O—$C_{3-6}$alkynyl, $Ar^1$, $R^{6b}$—O—, $R^{6b}$—S—, $R^{6c}$—SO—, $R^{6c}$—SO$_2$—, $R^{6b}$—O—$C_{1-6}$alkyl-SO$_2$—, —N($R^{6a}R^{6b}$), $CF_3$, $R^{6c}$—C(=O)—, $R^{6b}$—O—C(=O)—, N($R^{6a}R^{6b}$)—C(=O)—, $R^{6b}$—O—$C_{1-6}$alkyl, $R^{6b}$—S—$C_{1-6}$alkyl, $R^{6c}$—S(=O)$_2$—$C_{1-6}$alkyl, N($R^{6a}R^{6b}$)—$C_{1-6}$alkyl, $R^{6c}$—C(=O)—$C_{1-6}$alkyl, $R^{6b}$—O—C(=O)—$C_{1-6}$alkyl, N($R^{6a}R^{6b}$)—C(=O)—$C_{1-6}$alkyl and $R^{6c}$—C(=O)—NR$^{6b}$—, $H_2N$—C(=NH)—.

10. A compound according to claim 4 wherein $R^9$, $R^{10}$, $R^{11}$ are selected from $C_{1-6}$alkyl, $Ar^1$—$C_{1-6}$alkyl, cyano$C_{1-6}$alkyl, $C_{2-6}$alkenyl, cyano$C_{2-6}$alkenyl, $R^{6b}$—O—$C_{3-6}$alkenyl, $C_{2-6}$alkynyl, cyano$C_{2-6}$alkynyl, $R^{6b}$—O—$C_{3-6}$alkynyl, $R^{6b}$—O—$C_{1-6}$alkyl, $R^{6b}$—S—$C_{1-6}$alkyl, $R^{6c}$—S(=O)$_2$—$C_{1-6}$alkyl, N($R^{6a}R^{6b}$)—$C_{1-6}$alkyl, $R^{6b}$—O—C(=O)—$C_{1-6}$ alkyl and N($R^{6a}R^{6b}$)—C(=O)—$C_{1-6}$alkyl.

11. A compound according to claim 5, wherein $R^9$, $R^{10}$, $R^{11}$ are selected from hydrogen, $C_{1-6}$alkyl, $Ar^1$—$C_{1-6}$alkyl, cyano$C_{1-6}$alkyl, $C_{2-6}$alkenyl, cyano$C_{2-6}$alkenyl, $C_{2-6}$alkynyl, cyano$C_{2-6}$alkynyl, $R^{6b}$—O—$C_{1-6}$alkyl, amino-S(=O)$_2$—$C_{1-6}$alkyl, $R^{6b}$—O—C(=O)—$C_{1-6}$alkyl, amino-C(=O)—$C_{1-6}$alkyl, mono- and diamino-C(=O)—$C_{1-6}$alkyl.

12. A compound according to claim 5, wherein $R^9$, $R^{10}$, $R^{11}$ are $C_{1-6}$alkyl or $R^{6b}$—O—$C_{1-6}$alkyl; and $R^{10}$ and/or $R^{11}$ may also be hydrogen.

13. A compound according to claim 1, wherein G is $C_{1-10}$alkanediyl.

14. A compound according to claim 1, wherein G is methylene.

15. A compound according to claim 1, wherein $R^1$ is pyridyl; wherein said pyridyl may be substituted with 1 or where possible with 2 or 3 substituents independently selected from the group consisting of halo, hydroxy, amino, cyano, carboxyl, $C_{1-6}$alkyl, $C_{1-6}$alkyloxy, $C_{1-6}$alkylthio, $C_{1-6}$alkyloxy$C_{1-6}$alkyl, $Ar^1$, $Ar^1C_{1-6}$alkyl, $Ar^1C_{1-6}$alkyloxy, hydroxy$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkylcarbonylamino, $C_{1-6}$alkyl-SO$_2$—NR$^{5c}$—, $Ar^1$—SO$_2$—NR$^{5c}$—, $C_{1-6}$alkyloxycarbonyl, —C(=O)—NR$^{5c}$R$^{5d}$, HO(—CH$_2$—CH$_2$—O)$_n$—, halo(—CH$_2$—CH$_2$—O)$_n$—, $C_{1-6}$alkyloxy(—CH$_2$—CH$_2$—O)$_n$—, $Ar^1C_{1-6}$alkyloxy(—CH$_2$—CH$_2$—O)$_n$— and mono- or di($C_{1-6}$alkyl)amino(—CH$_2$—CH$_2$—O)$_n$—; wherein each n independently is 1, 2, 3 or 4; $Ar^1$, $R^{5c}$, $R^{5d}$ are as claimed in claim 1.

16. A compound according to claim 1, wherein $R^1$ is pyridyl, wherein said pyridyl may optionally be substituted with one, two or three radicals selected from the group consisting of halo, hydroxy, $C_{1-6}$alkyl, $C_{1-6}$alkyloxy, $Ar^1C_{1-6}$alkyloxy, ($C_{1-6}$alkyloxy)$C_{1-6}$alkyloxy.

17. A compound according to claim 1, wherein $R^1$ is pyridyl optionally substituted with one or two radicals selected from the group consisting of halo, hydroxy, $C_{1-6}$alkyl, $C_{1-6}$alkyloxy, $Ar^1C_{1-6}$alkyloxy, ($C_{1-6}$alkyloxy)$C_{1-6}$alkyloxy.

18. A compound according to claim 1, wherein $R^1$ is pyridyl optionally substituted with one or two radicals selected from hydroxy, halo, $C_{1-6}$alkyl, benzyloxy and $C_{1-6}$alkyloxy.

19. A compound according to claim 1, wherein $R^1$ is pyridyl optionally substituted with one or two radicals selected from hydroxyl, $C_{1-6}$alkyl and $C_{1-6}$alkyloxy.

20. A compound according to claim 1, wherein, where applicable, one of $R^{2a}$ and $R^{3a}$ is selected from —N($R^{4a}R^{4b}$), ($R^{4a}R^{4b}$)N—CO—, $C_{1-6}$alkyl substituted with one or two substituents selected from hydroxy, cyano, $Ar^2$, or —N($R^{4a}R^{4b}$) and $C_{2-6}$alkenyl substituted with cyano or $Ar^2$; and the other one of $R^{2a}$ and $R^{3a}$ is hydrogen; and
in case $R^{2a}$ is different from hydrogen then $R^{2b}$ is hydrogen, $C_{1-6}$alkyl or halogen and $R^{3b}$ is hydrogen;
in case $R^{3a}$ is different from hydrogen then $R^{3b}$ is hydrogen, $C_{1-6}$alkyl or halogen and $R^{2b}$ is hydrogen.

21. A compound according to claim 1, wherein, where applicable, one of $R^{2a}$ and $R^{3a}$ is selected from ($R^{4a}R^{4b}$)N—CO—; $C_{1-6}$alkyl optionally substituted with hydroxy, $Ar^2$, or —N($R^{4a}R^{4b}$); and $C_{2-6}$alkenyl substituted with $Ar^1$; and the other one of $R^{2a}$ and $R^{3a}$ is hydrogen; or
in case $R^{2a}$ is different from hydrogen then $R^{2b}$ is hydrogen or $C_{1-6}$alkyl and $R^{3b}$ is hydrogen;
in case $R^{3a}$ is different from hydrogen then $R^{3b}$ is hydrogen or $C_{1-6}$alkyl and $R^{2b}$ is hydrogen;
$Ar^2$, $R^{4a}$ and $R^{4b}$ are as in the definitions of the compounds of formula (I) or as in any subgroup specified herein.

22. A compound according to claim 20, wherein, where applicable, $R^{2b}$ and $R^{3b}$ are both hydrogen.

23. A compound according to claim 1, wherein the compound is 2-(2-amino-6-{[2-(3-hydroxy-propyl)-5-methyl-phenylamino]-methyl}-benzoimidazol-1-ylmethyl)-6-methyl-pyridin-3-ol.

24. A pharmaceutical composition comprising a pharmaceutically acceptable carrier, and as active ingredient a therapeutically effective amount of a compound as claimed in claim 1.

25. A process for preparing a compound as claimed in claim 1, said process comprising (a) reacting an intermediate of formula (II) with a reagent (III) as in the following reaction scheme:

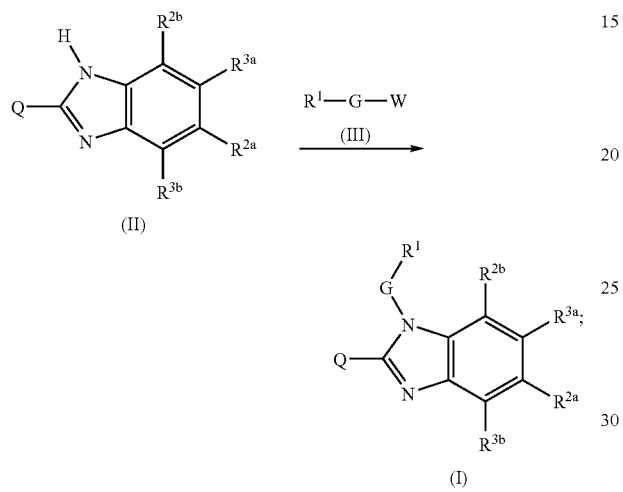

(b) reacting an intermediate of formula (V) with a reagent (I) thus obtaining a compound of formula (I-d); wherein, optionally, intermediate (V) can be prepared by a cyclization reaction of an intermediate (IV); as in the following reaction scheme;

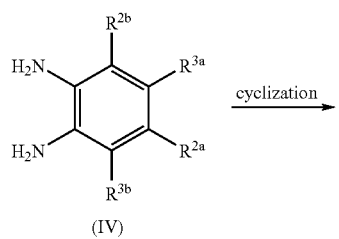

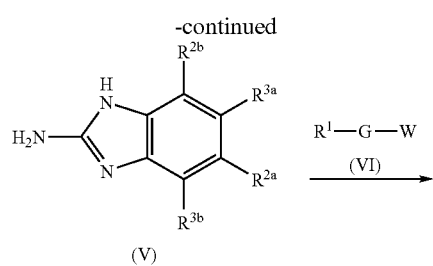

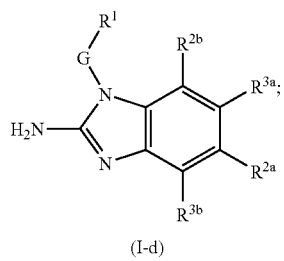

and optionally converting the thus obtained compounds of formula (I) into their pharmaceutically acceptable base-addition or acid addition salt form by treatment with a suitable base or acid and conversely treating the base-addition or acid addition salt form with an acid or a base to obtain the free form of the compound of formula (I).

26. A compound according to claim 5, wherein Alk is methylene.

27. A compound according to claim 6, wherein Alk is methylene.

28. A compound according to claim 7, wherein Alk is methylene.

29. A compound according to claim 21 wherein $R^{2b}$ and $R^{3b}$ are both hydrogen.

* * * * *